US012570955B2

(12) United States Patent
Barney et al.

(10) Patent No.: US 12,570,955 B2
(45) Date of Patent: Mar. 10, 2026

(54) MONOCLONAL CELL LINES EXPRESSING AN EXOGENOUS SUBSTANCE AND USES THEREOF

(71) Applicant: SIGILON THERAPEUTICS, INC., Cambridge, MA (US)

(72) Inventors: Lauren Emily Barney, Cambridge, MA (US); Guillaume Carmona, Cambridge, MA (US); Marianthi Papakosta, Cambridge, MA (US); Jared A Sewell, Somerville, MA (US)

(73) Assignee: SIGILON THERAPEUTICS, INC., Cambridge, MA (US)

( * ) Notice: Subject to any disclaimer, the term of this patent is extended or adjusted under 35 U.S.C. 154(b) by 958 days.

(21) Appl. No.: 17/778,159

(22) PCT Filed: Nov. 20, 2020

(86) PCT No.: PCT/US2020/061524
§ 371 (c)(1),
(2) Date: May 19, 2022

(87) PCT Pub. No.: WO2021/102271
PCT Pub. Date: May 27, 2021

(65) Prior Publication Data

US 2023/0038379 A1 Feb. 9, 2023

Related U.S. Application Data

(60) Provisional application No. 63/004,212, filed on Apr. 2, 2020, provisional application No. 62/938,995, filed on Nov. 22, 2019.

(51) Int. Cl.
*C12N 5/071* (2010.01)
*C12N 5/00* (2006.01)
(Continued)

(52) U.S. Cl.
CPC ......... *C12N 5/0602* (2013.01); *C12N 5/0012* (2013.01); *C12N 15/63* (2013.01); *C12N 15/90* (2013.01); *C12N 2510/02* (2013.01)

(58) Field of Classification Search
None
See application file for complete search history.

(56) References Cited

U.S. PATENT DOCUMENTS 9,422,373 B2 8/2016 Vegas et al.
9,555,007 B2 1/2017 Ma et al.
(Continued)

FOREIGN PATENT DOCUMENTS

WO 2012/167223 A1 12/2012
WO 2014/153126 A1 9/2014
(Continued)

OTHER PUBLICATIONS

GenBank Accession No. CP034498 "Eukaryotic synthetic construct chromosome 2" Apr. 1, 4-5, 12-16, 18, 19-24, 2019 [online]. [Retrieved on Feb. 10, 2021]. Retrieved from the Internet: URL: https://www.ncbi.nlm.nih.gov/nuccore/CP034498.
(Continued)

*Primary Examiner* — Tracy Vivlemore
*Assistant Examiner* — Hanna Marie Thueson
(74) *Attorney, Agent, or Firm* — Quarles & Brady, LLP

(57) ABSTRACT

Described herein are genetically modified cells derived from a human cell and which contain at least one exogenous transcription unit inserted into at least one of four open chromatin regions (OCRs) located on Chromosomes 2, 5, 8 and 12, as well as compositions, pharmaceutical preparations, and implantable devices comprising the genetically modified cells, and methods of using the same for preventing or treating a disease, disorder, or condition.

17 Claims, 29 Drawing Sheets

Specification includes a Sequence Listing.

(SEQ ID NO:1)

| SEQ ID NO:1 | Nucleotide sequence of positions 100817157 to 100818556 in Chr 2 of the human hg19 reference genome |
|---|---|
| TCCAGCACAAAAGACATTTGGAGGAGAACAATTTAATTATAAAAGCATTTTTTTTACATCTACTATTTCATTTATTGT | |
| CAGATTAGGGGATAGACCTTAATTATAGTTTTTAATAAGTATTCTTAACCTGTTGCATATCTATGGTGTTTTTCAAAG | |
| TTACTACAATACAGTAAATAATTCTCAACAGATTAAGAAGGTAATAACATATTC**C**TTTTAA**A**GAAAGATATTGAGAAA | |
| TATGTAAGAAATGATAGTCTCCTATTCTCATGTCTGTGTTCACTACCCACGTGTTTTCTGGGAAGAAATATGAAATAA | |
| AATGATTTTCAAAAGAGAGTCCTTCTCAAACAAATACTGACGGTTAACTGCTTTTACATATAATGGCAAGTTGAGTCA | |
| GCCACCATTTTTAATAAAACTGATTAATGACTAAGTGTGGACAAAACAGGGAAGTGAGTAATCAGGTGGAATTTATGC | |
| TATCCTAAAGCCGGAATAAAAGTCTATGAGATGGAAAAAAAGTCTTTAGGGGCTTGGCCAAGTTCTTAAATAATTGGG | |
| AGGCTGAGCAGAGGGGCCGCTCTCAGGAATCAGCATCCAGTTGCACAGACAGAGCCTATTAAAAATTAAGAAAATAGT | |
| TTGAGATGACTATTTTAAGCGTTATGAATTGCCAAATGGCAAATGCCTAGCTGAACAGATGACTGGTTTGGATTCTTA | |
| ATAGCCAATTGTAAAGGAAATGGACCACAACAGGCTTTCAGACACAGAAGTGGCCGTCCGTGCTGAGACCGAGGTGTG | |
| GGGTACATCTAAATGTAAGGATCAGCAGTTCCCCAGAGAGCAAACGTGAAAAGCTCAAGTCTAATTTCCCATCATTGT | |
| TGAGCATTTTCCAGAAAATTAAGGGCCAATCTGGAGCTGGAGATAGGAGTGTAGGGAGCATCTGCATTGGACTGAGTC | |
| TTAGAGTTGGGGAAGCCCAGGGACGGGGTGAGACTATTTTAGGCGTTATTTAACAGTCTAATAATTCGAGGGGTTTTT | |
| AAGACCATTGTATTAATCATGCTTTTTCTTGTCCATATTTCCTGGTGCTTTGACATCTTGGGGCCCTGCTTGACTCTG | |
| AAGAGACTGCCCCTTCCAGGGCTGGCCAAATCCTAGAGATAGTAAGTGACTTGCCTTTACTACGCCAGTAAGCTATAA | |
| TCACCCAAGGCCAAGTACCAGACAACCCAGGAAGGCATCTACACCCCAGAGCCTGCTGAAATTATTCAGACCAGCCAA | |
| TCCTAAGCCTGCCTACACTGCCTTGTCCTTTCCTTCCTGCAGAAACCACAATAAAGGCTGTCACCCATGTTTCCCCCT | |
| CAATCTCTCTACCTCCTGACAGCCCCTGGTACTTCCCATGTGGCCCTGCATGGCATGGCCTGTCCTCACTTCTC | |

(SEQ ID NO:2)

| SEQ ID NO:2 | Nucleotide sequence of positions 53853682 to 53854987 on chromosome 5 of the human hg19 reference genome |
|---|---|
| ACTGTGTTGGACGCTCCCATGTATTGTCTTTTTTTTTAAATGTATTTTTATTTGTTTTT**TA**AAATAGAGACAGAACCTC | |
| ACCATGTTGCCCGGGCTGGTCTCAAACTCCCTGGGCTCAGGCAATCCTCCTGCCTTGGCCTCCCAAAGTGCTGGGATT | |
| ATAGGTGTGAGCCACAGTGCTGTGCCCTGGGTATTGTTTAGTCCTCCCAACAACTCTATGAGGCAGATATAATTGACC | |
| TATTTTGCAGGTAAAAAAGACTCTGTAACTTGCCCAGAGTCACACAAACTGGGATTTGAGCCCAACTTGTCTTTCTCC | |
| TGTGTCCTGGTACATAAGTAAGATCCATGGGATTTTCACTGTAAACATCACCCTAAATATTTTTTAAAGTAGAAATAC | |
| CCATATTAGAAATGACTCAAGGGCACAATTACTTAGCTAGAATATAAAATTCCTGGAAACATTTACTGGCTTCTCCAG | |
| ATAAAGTTTATCTTACTAAATAATTAGGACTTTTATTTTTTCCTCCTTCCCTCCCTCTCTCCATTCCATCATTCTTTT | |
| CTCATTCTTTCTTTCAAGATTAGAGTAATATCTAAATCACAGTCACGTAGAGCAGTACAACCCATGTTGAGGTAACTT | |
| ATTAAATTAGCCCCTGACCATACATTACTATTCAGAGGGCTGGGAAAGATCTGTAAGGGATTGGACAAAGGAAATGCT | |
| CCACCTGTTCCTCCTCTGACTTGGGCCCTTGATGATATCATATAAAAAGTCATTTCCTGCTTGGTCCTTATCTCTAAT | |
| GCTGACTAAATTAATAGTCTTACTTCCTTTACTTGTGTGTATGGAATTTGGGAATAAAAGTAAAATCACTTCCTACTG | |
| GGTTTTATACTTAGGCTCCTTAAATTTCATGTACTTGGGCAATTTTTCCTTATTTGGGGACTACAGGTTGTTCGATGT | |
| AAAAAAGGAACAAATTATAACACATGCCATGCCGAAATTCAGTGAGAGTCATGGTTTACCTGGTACCCATGTTCTAAT | |
| GAATGTATTTCCAACCTGTAAACTTGCTGAAGATTTGGAATAAGTAAAACCAAAATCATACTAGTATGGAGGTTTTAA | |
| AACTAACTTAAAAGAGTGACTGTATATTCACAATTGCTACCAAAAAAAAAAATACCTAGGAATACAGCTAACTAGGGA | |
| GGTGAAAGAGCTCTACAAGGAGAACTGTTAAACACTGAAAAGAAATCAGAGATGATGCAAACAAATGGAAAAACATTC | |
| CATGCTCATGGATAGGAGGAATCAACATCATTAAAATGGCCATAGTGCCCAAAGCAAT | |

(51) Int. Cl.

| | |
|---|---|
| ***C12N 15/63*** | (2006.01) |
| ***C12N 15/90*** | (2006.01) |

(56) References Cited

U.S. PATENT DOCUMENTS

| | | | |
|---|---|---|---|
| 10,172,791 B2 | 1/2019 | Ma et al. | |
| 10,285,949 B2 | 5/2019 | Vegas et al. | |
| 10,292,936 B2 | 5/2019 | Vegas et al. | |
| 10,426,735 B2 | 10/2019 | Vegas et al. | |
| 10,709,818 B2 | 7/2020 | Vegas et al. | |
| 10,729,818 B2 | 8/2020 | Vegas et al. | |
| 10,786,446 B2 | 9/2020 | Ma et al. | |
| 10,835,486 B2 | 11/2020 | Ma et al. | |
| 10,842,753 B2 | 11/2020 | Vegas et al. | |
| 10,898,443 B2 | 1/2021 | Vegas et al. | |
| 11,090,413 B2 | 8/2021 | Vegas et al. | |
| 11,266,606 B2 | 3/2022 | Vegas et al. | |
| 2006/0166874 A1 | 7/2006 | Haaning et al. | |
| 2012/0141573 A1 | 6/2012 | Ling et al. | |
| 2013/0195806 A1 | 8/2013 | Gay et al. | |
| 2018/0119138 A1* | 5/2018 | Bauer | C12N 15/1082 |
| 2021/0186886 A1 | 6/2021 | Vegas et al. | |

FOREIGN PATENT DOCUMENTS

| | | |
|---|---|---|
| WO | 2016/019391 A1 | 2/2016 |
| WO | 2016/187225 A1 | 11/2016 |
| WO | 2017/075631 A1 | 5/2017 |
| WO | 2018/204764 A1 | 11/2018 |
| WO | 2019/067766 A1 | 4/2019 |
| WO | 2019/195055 A1 | 10/2019 |
| WO | 2019/195056 A1 | 10/2019 |
| WO | 2020/069429 A1 | 4/2020 |

OTHER PUBLICATIONS

International Search Report and Written Opinion for Application No. PCT/US2020/061524 mailed Apr. 26, 2021.

Fjord-Larsen et al., "Increased encapsulated cell biodelivery of nerve growth factor in the brain by transposon-mediated gene transfer" Gene Therapy, 2012, vol. 19, No. 10, pp. 1010-1017.

Johnen et al., "Sleeping Beauty Transposon-Mediated transfection of retinal and iris pigment epithelial cells" Investigative Opthalmology & Visual Science, 2012, vol. 53, No. 8, pp. 4787-4796.

Hernandez et al., "Preclinical evaluation of a cell-based gene therapy using the sleeping beauty transposon system in choroidal neovascularization" Molecular Therapy-Methods & Clinical Development, 2019, vol. 15, No. 9, pp. 403-417.

Galvan et al., "Genome-wide mapping of PiggyBac transposon integrations in primary human T cells" Journal of Immunotherapy, 2010, vol. 32, No. 8, pp. 837-844.

Nair et al., "Effect of different UCOE-promoter combinations in creation of engineered cell lines for the production of Factor VIII" Bmc Research Notes, Biomed Central LTD, 2011, vol. 4, No. 1, p. 178.

* cited by examiner

FIG. 1A (SEQ ID NO:1)

<table>
<tr><td>SEQ ID NO:1</td><td>Nucleotide sequence of positions 100817157 to 100818556 in Chr 2 of the human hg19 reference genome</td></tr>
<tr><td colspan="2">TCCAGCACAAAAGACATTTGGAGGAGAACAATTTAATTATAAAAGCATTTTTTTTACATCTACTATTTCATTTATTGT<br>CAGATTAGGGGATAGACCTTAATTATAGTTTTTAATAAGTATTCTTAACCTGTTGCATATCTATGGTGTTTTTCAAAG<br>TTACTACAATACAGTAAATAATTCTCAACAGATTAAGAAGGTAATAACATATTC<u>C</u>TTTTAA<u>A</u>GAAAGATATTGAGAAA<br>TATGTAAGAAATGATAGTCTCCTATTCTCATGTCTGTGTTCACTACCCACGTGTTTTCTGGGAAGAAATATGAAATAA<br>AATGATTTTCAAAAGAGAGTCCTTCTCAAACAAATACTGACGGTTAACTGCTTTTACATATAATGGCAAGTTGAGTCA<br>GCCACCATTTTTAATAAAACTGATTAATGACTAAGTGTGGACAAAACAGGGAAGTGAGTAATCAGGTGGAATTTATGC<br>TATCCTAAAGCCGGAATAAAAGTCTATGAGATGGAAAAAAAGTCTTTAGGGGCTTGGCCAAGTTCTTAAATAATTGGG<br>AGGCTGAGCAGAGGGGCCGCTCTCAGGAATCAGCATCCAGTTGCACAGACAGAGCCTATTAAAAATTAAGAAAATAGT<br>TTGAGATGACTATTTTAAGCGTTATGAATTGCCAAATGGCAAATGCCTAGCTGAACAGATGACTGGTTTGGATTCTTA<br>ATAGCCAATTGTAAAGGAAATGGACCACAACAGGCTTTCAGACACAGAAGTGGCCGTCCGTGCTGAGACCGAGGTGTG<br>GGGTACATCTAAATGTAAGGATCAGCAGTTCCCCAGAGAGCAAACGTGAAAAGCTCAAGTCTAATTTCCCATCATTGT<br>TGAGCATTTTCCAGAAAATTAAGGGCCAATCTGGAGCTGGAGATAGGAGTGTAGGGAGCATCTGCATTGGACTGAGTC<br>TTAGAGTTGGGGAAGCCCAGGGACGGGGTGAGACTATTTTAGGCGTTATTTAACAGTCTAATAATTCGAGGGGTTTTT<br>AAGACCATTGTATTAATCATGCTTTTTCTTGTCCATATTTCCTGGTGCTTTGACATCTTGGGGCCCTGCTTGACTCTG<br>AAGAGACTGCCCCTTCCAGGGCTGGCCAAATCCTAGAGATAGTAAGTGACTTGCCTTTACTACGCCAGTAAGCTATAA<br>TCACCCAAGGCCAAGTACCAGACAACCCAGGAAGGCATCTACACCCCAGAGCCTGCTGAAATTATTCAGACCAGCCAA<br>TCCTAAGCCTGCCTACACTGCCTTGTCCTTTCCTTCCTGCAGAAACCACAATAAAGGCTGTCACCCATGTTTCCCCCT<br>CAATCTCTCTACCTCCTGACAGCCCCTGGTACTTCCCATGTGGCCCTGCATGGCATGGCCTGTCCTCACTTCTC</td></tr>
</table>

FIG. 1B (SEQ ID NO:2)

<table>
<tr><td>SEQ ID NO:2</td><td>Nucleotide sequence of positions 53853682 to 53854987 on chromosome 5 of the human hg19 reference genome</td></tr>
<tr><td colspan="2">ACTGTGTTGGACGCTCCCATGTATTGTCTTTTTTTTTAAATGTATTTTTATTTGTTTTT<u>TA</u>AAATAGAGACAGAACCTC<br>ACCATGTTGCCCGGGCTGGTCTCAAACTCCCTGGGCTCAGGCAATCCTCCTGCCTTGGCCTCCCAAAGTGCTGGGATT<br>ATAGGTGTGAGCCACAGTGCTGTGCCCTGGGTATTGTTTAGTCCTCCCAACAACTCTATGAGGCAGATATAATTGACC<br>TATTTTGCAGGTAAAAAAGACTCTGTAACTTGCCCAGAGTCACACAAACTGGGATTTGAGCCCAACTTGTCTTTCTCC<br>TGTGTCCTGGTACATAAGTAAGATCCATGGGATTTTCACTGTAAACATCACCCTAAATATTTTTTAAAGTAGAAATAC<br>CCATATTAGAAATGACTCAAGGGCACAATTACTTAGCTAGAATATAAAATTCCTGGAAACATTTACTGGCTTCTCCAG<br>ATAAAGTTTATCTTACTAAATAATTAGGACTTTTATTTTTTCCTCCTTCCCTCCCTCTCTCCATTCCATCATTCTTTT<br>CTCATTCTTTCTTTCAAGATTAGAGTAATATCTAAATCACAGTCACGTAGAGCAGTACAACCCATGTTGAGGTAACTT<br>ATTAAATTAGCCCCTGACCATACATTACTATTCAGAGGGCTGGGAAAGATCTGTAAGGGATTGGACAAAGGAAATGCT<br>CCACCTGTTCCTCCTCTGACTTGGGCCCTTGATGATATCATATAAAAAGTCATTTCCTGCTTGGTCCTTATCTCTAAT<br>GCTGACTAAATTAATAGTCTTACTTCCTTTACTTGTGTGTATGGAATTTGGGAATAAAAGTAAAATCACTTCCTACTG<br>GGTTTTATACTTAGGCTCCTTAAATTTCATGTACTTGGGCAATTTTTCCTTATTTGGGGACTACAGGTTGTTCGATGT<br>AAAAAAGGAACAAATTATAACACATGCCATGCCGAAATTCAGTGAGAGTCATGGTTTACCTGGTACCCATGTTCTAAT<br>GAATGTATTTCCAACCTGTAAACTTGCTGAAGATTTGGAATAAGTAAAACCAAAATCATACTAGTATGGAGGTTTTAA<br>AACTAACTTAAAAGAGTGACTGTATATTCACAATTGCTACCAAAAAAAAAAAATACCTAGGAATACAGCTAACTAGGGA<br>GGTGAAAGAGCTCTACAAGGAGAACTGTTAAACACTGAAAAGAAATCAGAGATGATGCAAACAAATGGAAAAACATTC<br>CATGCTCATGGATAGGAGGAATCAACATCATTAAAATGGCCATAGTGCCCAAAGCAAT</td></tr>
</table>

FIG. 1C (SEQ ID NO:3)

<table>
<tr><td>SEQ ID NO:3</td><td>Nucleotide sequence of positions 122186354 to 122187572 on chromosome 12 of the human hg19 reference genome</td></tr>
<tr><td colspan="2">AGCTGGCAACCTCCCCACCCCTAGCACAGGCCCATGCCCAGGCCTAGCACAGCTGGTCCATATAACTCTCGCCTTCCT<br>GCTGGTGCTCAGATTGAAGGGGAAAGAGGGAAACAAGGGCAGGAGAGATAAGGAGCCTTCCTTACACATTCCTCCATG<br>AGCCCAGGAGGGGACCTTAGCCACACCGTGTGACAGCAGCATTCCTGGGAGGTCCGTTGCAAGGAACCAGCACTCACT<br>GCATGCCTGCTGACACCTGGGGTTAAGAGGGAAACTGTCCTCTCCCAGGAGAACAAACATGCATTGCGTGCCTCCTGC<br>ACGCTCAGAGCTGTGCCGGGACCTCCTGTGATGTCACCTGGTTTATCCTCAACAATCTGTGCGTCAGACCAAGAGATG<br>CCCATTTTTACAAGATTCAGAGACATCAGCGAATGTTTGGCCACACCAGGATGTGAACAGCAGACATTCTGACTCCAA<br>AGCCCACGTTCTTTGTATTTTCCCCCTTCAGAGAAGTCCCCGTTCCCTCCCTTAAGTGATGTCATTGCCACCTTGTTC<br>TGGAGAGAGAGAGCTGCTTACAGCCTCATATCATCATGACCTGACTTAACGCTGCTGAGCACAGTCAGTTCACCCTGA<br>CCCTGTTTTCCGGATCAGCCTCGCGCTGAGTCAGAGCCGTGCATTAGGAGGAGGGGCTCCTTTCAGGCCTGTAGCGGG<br>TGGGAGGGAGCTGGCTAGCCCTGTTATATTTTAACCCATTCCTCCGAGCTTCTCCTTTTTGACTGTGTTCGAATAGAC<br>CCCATGAGTTAAGTGATGATCATTTTCTGCAGAATGAGCAGCAGCCTAGCATTCGTGACCCTCTTACAGTGTCATGCG<br>TGTCTGCCTTCCTGCCCCTCTGTCCCTAGGCCTCTGTGCCTCTTAACCTCAGTTGGGAATCTTTGGATTGCAAACGAT<br>AGAAAACCCAACTCAAGGCCGGGCGCGGTGGCTTGTGCCTGTCATCCCAGCACTTCGGGAGGCCGAGGTGGGAGGATC<br>ACTTGAGCCCAGGAATTCAAGACCAGCCTGGACAACATTGTGAGACCACATCTCTACAAAACTTTAACAAAATTGGTG<br>TGCTGGTGTGTACCCATAATCCCAGCTACTTTGGCGACTGAGGTGGGAGGACTACTTGAGCCTAGAGGTTCAAGACTG<br>CAGTGACGCTGGGCACAGTGGCTCATGCCTGTAATCCCAGCACTTTGGG</td></tr>
</table>

FIG. 1D (SEQ ID NO:26)

| | |
|---|---|
| SEQ ID NO:26 | Nucleotide sequence of position 30,105,499 to 30,106,497 on chromosome 8 of the human hg38 reference genome |

AGTACCACTTTTATACTATAAATATATTTATACTGTATATATTTATATATATTTATACTA
TATATTTTTTTACTATATATATTTATACTATATATATTTATAAGTATGTGTTCAGCACTG
TGACAATTATTGTTACAAGGCATGCTTCTTTTAGATCATAATTGGGATACAACTAGAGCC
TTGATTTTTTTTTTTATTTTCCTTTCGTTTTTCATGCCTGTTGACTGAGTGTATCTTATT
TCCATAGATTGAGTGGGGAGCTTGTGCACTTGTTCTCACAGGAAACACAGTCATCTTTGC
AACTATACTAGGCTTTTTCTTGGTCTTTGGAAGCAATGACGACTTCAGCTGGCAGCAGTG
GTGAAAAGAAATTACTGAACTATTGTCAAATGGACTTCCTGTCATTTGTTGGCCATTCAC
GCACACAGGAGATGGGGCA*G*TTAA*T*GCTGAATGGTATAGCAAGCCTCTTGGGGGTATTTT
AGGTGCTCCCTTCTCACTTTTATTGTAAGCATACTATTTTCACAGAGACTTGCTGAAGGA
TTAAAAGGATTTTCTCTTTTGGAAAAGCTTGACTGATTTCACACTTATCTATAGTATGCT
TTTTGTGGTGTCCTGCTGAATTTAAATATTTATGTGTTTTTCCTGTTAGGTTGATTTTTT
TTGGAATCAATATGCAATGTTAAACACTTTTTTAATGTAATCATTTGCATTGGTTAGGAA
TTCAGAATTCCGCCGGCTCTATTACTGGTCAAGTACATCTTTTCTCTTAAAATTATTTAG
CCTCCATTATTACAAAAAATTATAAAAATAAGTTTTCAGTCAGTCAGGATGACATCACTC
CCAATGTTATGCAGACATACAGACGGTTGGCATACGTTATAGACTGTATACTCAGTGCAA
ATATAGCTGCATTTATACCTCAGAGGGGCCAAGTGTTAATGCCCATGCCCTCCGTTAAGG
GTTGTTGGTTTTACTGGTAGACAGATGTTTTGTGGATTG

FIG. 2A (SEQ ID NO:4)

| SEQ ID NO:4 | pCAG Promoter |
| --- | --- |
| CTCGACATTGATTATTGACTAGTTATTAATAGTAATCAATTACGGGGTCATTAGTTCATAGCCCATATATGGAGTTCC<br>GCGTTACATAACTTACGGTAAATGGCCCGCCTGGCTGACCGCCCAACGACCCCCGCCCATTGACGTCAATAATGACGT<br>ATGTTCCCATAGTAACGCCAATAGGGACTTTCCATTGACGTCAATGGGTGGAGTATTTACGGTAAACTGCCCACTTGG<br>CAGTACATCAAGTGTATCATATGCCAAGTACGCCCCCTATTGACGTCAATGACGGTAAATGGCCCGCCTGGCATTATG<br>CCCAGTACATGACCTTATGGGACTTTCCTACTTGGCAGTACATCTACGTATTAGTCATCGCTATTACCATGGTCGAGG<br>TGAGCCCCACGTTCTGCTTCACTCTCCCCATCTCCCCCCCCTCCCCACCCCCAATTTTGTATTTATTTATTTTTTAAT<br>TATTTTGTGCAGCGATGGGGGCGGGGGGGGGGGGGGGGCGCGCGCCAGGCGGGGCGGGGCGGGGCGAGGGGCGGGGCG<br>GGGCGAGGCGGAGAGGTGCGGCGGCAGCCAATCAGAGCGGCGCGCTCCGAAAGTTTCCTTTTATGGCGAGGCGGCGGC<br>GGCGGCGGCCCTATAAAAAGCGAAGCGCGCGGCGGGCGGGAGTCGCTGCGCGCTGCCTTCGCCCCGTGCCCCGCTCCG<br>CCGCCGCCTCGCGCCGCCCGCCCCGGCTCTGACTGACCGCGTTACTCCCACAGGTGAGCGGGCGGGACGGCCCTTCTC<br>CTCCGGGCTGTAATTAGCGCTTGGTTTAATGACGGCTTGTTTCTTTTCTGTGGCTGCGTGAAAGCCTTGAGGGGCTCC<br>GGGAGGGCCCTTTGTGCGGGGGGAGCGGCTCGGGGGGTGCGTGCGTGTGTGTGTGCGTGGGGAGCGCCGCGTGCGGCT<br>CCGCGCTGCCCGGCGGCTGTGAGCGCTGCGGGCGCGGCGCGGGGCTTTGTGCGCTCCGCAGTGTGCGCGAGGGGAGCG<br>CGGCCGGGGGCGGTGCCCCGCGGTGCGGGGGGGGCTGCGAGGGGAACAAAGGCTGCGTGCGGGGTGTGTGCGTGGGGG<br>GGTGAGCAGGGGGTGTGGGCGCGTCGGTCGGGCTGCAACCCCCCCTGCACCCCCCTCCCCGAGTTGCTGAGCACGGCC<br>CGGCTTCGGGTGCGGGGCTCCGTACGGGGCGTGGCGCGGGGCTCGCCGTGCCGGGCGGGGGGTGGCGGCAGGTGGGGG<br>TGCCGGGCGGGGCGGGGCCGCCTCGGGCCGGGGAGGGCTCGGGGGAGGGGCGCGGCGGCCCCCGGAGCGCCGGCGGCT<br>GTCGAGGCGCGGCGAGCCGCAGCCATTGCCTTTTATGGTAATCGTGCGAGAGGGCGCAGGGACTTCCTTTGTCCCAAA<br>TCTGTGCGGAGCCGAAATCTGGGAGGCGCCGCCGCACCCCCTCTAGCGGGCGCGGGGCGAAGCGGTGCGGCGCCGGCA<br>GGAAGGAAATGGGCGGGGAGGGCCTTCGTGCGTCGCCGCGCCGCCGTCCCCTTCTCCCTCTCCAGCCTCGGGGCTGTC<br>CGCGGGGGGACGGCTGCCTTCGGGGGGGACGGGGCAGGGCGGGGTTCGGCTTCTGGCGTGTGACCGGCGGCTCTAGAG<br>CCTCTGCTAACCATGTTCATGCCTTCTTCTTTTTCCTACAGCTCCTGGGCAACGTGCTGGTTATTGTGCTGTCTCATC<br>ATTTTGGCAAAGAATTG | |

FIG. 2B (SEQ ID NO:5)

| SEQ ID NO:5 | Cbh Promoter |
| --- | --- |

```
CGTTACATAACTTACGGTAAATGGCCCGCCTGGCTGACCGCCCAACGACCCCCGCCCATTGACGTCAATAGTAACGCC
AATAGGGACTTTCCATTGACGTCAATGGGTGGAGTATTTACGGTAAACTGCCCACTTGGCAGTACATCAAGTGTATCA
TATGCCAAGTACGCCCCCTATTGACGTCAATGACGGTAAATGGCCCGCCTGGCATTGTGCCCAGTACATGACCTTATG
GGACTTTCCTACTTGGCAGTACATCTACGTATTAGTCATCGCTATTACCATGGTCGAGGTGAGCCCCACGTTCTGCTT
CACTCTCCCCATCTCCCCCCCCTCCCCACCCCCAATTTTGTATTTATTTATTTTTTAATTATTTTGTGCAGCGATGGG
GGCGGGGGGGGGGGGGGGGCGCGCGCCAGGCGGGGCGGGGCGGGGCGAGGGGCGGGGCGGGGCGAGGCGGAGAGGTGC
GGCGGCAGCCAATCAGAGCGGCGCGCTCCGAAAGTTTCCTTTTATGGCGAGGCGGCGGCGGCGGCGGCCCTATAAAAA
GCGAAGCGCGCGGCGGGCGGGAGTCGCTGCGCGCTGCCTTCGCCCCGTGCCCCGCTCCGCCGCCGCCTCGCGCCGCCC
GCCCCGGCTCTGACTGACCGCGTTACTCCCACAGGTGAGCGGGCGGGACGGCCCTTCTCCTCCGGGCTGTAATTAGCT
GAGCAAGAGGTAAGGGTTTAAGGGATGGTTGGTTGGTGGGGTATTAATGTTTAATTACCTGGAGCACCTGCCTGAAAT
CACTTTTTTTCAGGTTGG
```

FIG. 2C (SEQ ID NO:6)

| SEQ ID NO:6 | Poly A Signal |
|---|---|
| TCCTCAGGTGCAGGCTGCCTATCAGAAGGTGGTGGCTGGTGTGGCCAATGCCCTGGCTCACAAATACCACTGAGATCT<br>TTTTCCCTCTGCCAAAAATTATGGGGACATCATGAAGCCCCTTGAGCATCTGACTTCTGGCTAATAAAGGAAATTTAT<br>TTTCATTGCAATAGTGTGTTGGAATTTTTTGTGTCTCTCACTCGGAAGGACATATGGGAGGGCAAATCATTTAAAACA<br>TCAGAATGAGTATTTGGTTTAGAGTTTGGCAACATATGCCCATATGCTGGCTGCCATGAACAAAGGTTGGCTATAAAG<br>AGGTCATCAGTATATGAAACAGCCCCCTGCTGTCCATTCCTTATTCCATAGAAAAGCCTTGACTTGAGGTTAGATTTT<br>TTTTATATTTTGTTTTGTGTTATTTTTTTCTTTAACATCCCTAAAATTTTCCTTACATGTTTTACTAGCCAGATTTTT<br>CCTCCTCTCCTGACTACTCCCAGTCATAGCTGTCCCTCTTCTCTTATGGAGATC | |

FIG. 2D (SEQ ID NO:7)

| SEQ ID NO:7 | Nucleotide sequence of transcription unit without coding sequence |
|---|---|

CTCGACATTGATTATTGACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTGACGTCAATAATGACGT
ATGTTCCCATAGTAACGCCAATAGGGACTTTCCATTGACGTCAATGGGTGGAGTATTTACGGTAAACTGCCCACTTGG
CAGTACATCAAGTGTATCATATGCCAAGTACGCCCCCTATTGACGTCAATGACGGTAAATGGCCCGCCTGGCATTATG
CCCAGTACATGACCTTATGGGACTTTCCTACTTGGCAGTACATCTACGTATTAGTCATCGCTATTACCATGGTCGAGG
TGAGCCCCACGTTCTGCTTCACTCTCCCCATCTCCCCCCCCTCCCCACCCCCAATTTTGTATTTATTTATTTTTTAAT
TATTTTGTGCAGCGATGGGGGCGGGGGGGGGGGGGGGGCGCGCGCCAGGCGGGGCGGGGCGGGGCGAGGGGCGGGGCG
GGGCGAGGCGGAGAGGTGCGGCGGCAGCCAATCAGAGCGGCGCGCTCCGAAAGTTTCCTTTTATGGCGAGGCGGCGGC
GGCGGCGGCCCTATAAAAAGCGAAGCGCGCGGCGGGCGGGAGTCGCTGCGCGCTGCCTTCGCCCCGTGCCCCGCTCCG
CCGCCGCCTCGCGCCGCCCGCCCCGGCTCTGACTGACCGCGTTACTCCCACAGGTGAGCGGGCGGGACGGCCCTTCTC
CTCCGGGCTGTAATTAGCGCTTGGTTTAATGACGGCTTGTTTCTTTTCTGTGGCTGCGTGAAAGCCTTGAGGGGCTCC
GGGAGGGCCCTTTGTGCGGGGGGAGCGGCTCGGGGGGTGCGTGCGTGTGTGTGTGCGTGGGGAGCGCCGCGTGCGGCT
CCGCGCTGCCCGGCGGCTGTGAGCGCTGCGGGCGCGGCGCGGGGCTTTGTGCGCTCCGCAGTGTGCGCGAGGGGAGCG
CGGCCGGGGGCGGTGCCCCGCGGTGCGGGGGGGGCTGCGAGGGGAACAAAGGCTGCGTGCGGGGTGTGTGCGTGGGGG
GGTGAGCAGGGGGTGTGGGCGCGTCGGTCGGGCTGCAACCCCCCCTGCACCCCCCTCCCCGAGTTGCTGAGCACGGCC
CGGCTTCGGGTGCGGGGCTCCGTACGGGGCGTGGCGCGGGGCTCGCCGTGCCGGGCGGGGGGTGGCGGCAGGTGGGGG
TGCCGGGCGGGGCGGGGCCGCCTCGGGCCGGGGAGGGCTCGGGGGAGGGGCGCGGCGGCCCCCGGAGCGCCGGCGGCT
GTCGAGGCGCGGCGAGCCGCAGCCATTGCCTTTTATGGTAATCGTGCGAGAGGGCGCAGGGACTTCCTTTGTCCCAAA
TCTGTGCGGAGCCGAAATCTGGGAGGCGCCGCCGCACCCCCTCTAGCGGGCGCGGGGCGAAGCGGTGCGGCGCCGGCA
GGAAGGAAATGGGCGGGGAGGGCCTTCGTGCGTCGCCGCGCCGCCGTCCCCTTCTCCCTCTCCAGCCTCGGGGCTGTC
CGCGGGGGGACGGCTGCCTTCGGGGGGGACGGGGCAGGGCGGGGTTCGGCTTCTGGCGTGTGACCGGCGGCTCTAGAG
CCTCTGCTAACCATGTTCATGCCTTCTTCTTTTTCCTACAGCTCCTGGGCAACGTGCTGGTTATTGTGCTGTCTCATC
ATTTTGGCAAAGAATTGCAAGTTTGTACAAAAAAGCAGGCTGCCACC[ORF]GAATTCGCGGCCGCTAAACCCAGCTT
TCTTGTACAAAGTGGCAACTTTATTATACATAGTTGA*TCCTCAGGTGCAGGCTGCCTATCAGAAGGTGGTGGCTGGTG*
*TGGCCAATGCCCTGGCTCACAAATACCACTGAGATCTTTTTCCCTCTGCCAAAAATTATGGGGACATCATGAAGCCCC*
*TTGAGCATCTGACTTCTGGCTAATAAAGGAAATTTATTTTCATTGCAATAGTGTGTTGGAATTTTTTGTGTCTCTCAC*
*TCGGAAGGACATATGGGAGGGCAAATCATTTAAAACATCAGAATGAGTATTTGGTTTAGAGTTTGGCAACATATGCCC*
*ATATGCTGGCTGCCATGAACAAAGGTTGGCTATAAAGAGGTCATCAGTATATGAAACAGCCCCCTGCTGTCCATTCCT*
*TATTCCATAGAAAAGCCTTGACTTGAGGTTAGATTTTTTTTATATTTTGTTTTGTGTTATTTTTTTCTTTAACATCCC*
*TAAAATTTTCCTTACATGTTTTACTAGCCAGATTTTTCCTCCTCTCCTGACTACTCCCAGTCATAGCTGTCCCTCTTC*
*TCTTATGGAGATC*

FIG. 3A (SEQ ID NO:8)

| SEQ ID NO:8 | rhFVIII-BDD Protein |
|---|---|

MQIELSTCFF LCLLRFCFSA TRRYYLGAVE LSWDYMQSDL GELPVDARFP PRVPKSFPFN TSVVYKKTLF
VEFTDHLFNI AKPRPPWMGL LGPTIQAEVY DTVVITLKNM ASHPVSLHAV GVSYWKASEG AEYDDQTSQR
EKEDDKVFPG GSHTYVWQVL KENGPMASDP LCLTYSYLSH VDLVKDLNSG LIGALLVCRE GSLAKEKTQT
LHKFILLFAV FDEGKSWHSE TKNSLMQDRD AASARAWPKM HTVNGYVNRS LPGLIGCHRK SVYWHVIGMG
TTPEVHSIFL EGHTFLVRNH RQASLEISPI TFLTAQTLLM DLGQFLLFCH ISSHQHDGME AYVKVDSCPE
EPQLRMKNNE EAEDYDDDLT DSEMDVVRFD DDNSPSFIQI RSVAKKHPKT WVHYIAAEEE DWDYAPLVLA
PDDRSYKSQY LNNGPQRIGR KYKKVRFMAY TDETFKTREA IQHESGILGP LLYGEVGDTL LIIFKNQASR
PYNIYPHGIT DVRPLYSRRL PKGVKHLKDF PILPGEIFKY KWTVTVEDGP TKSDPRCLTR YYSSFVNMER
DLASGLIGPL LICYKESVDQ RGNQIMSDKR NVILFSVFDE NRSWYLTENI QRFLPNPAGV QLEDPEFQAS
NIMHSINGYV FDSLQLSVCL HEVAYWYILS IGAQTDFLSV FFSGYTFKHK MVYEDTLTLF PFSGETVFMS
MENPGLWILG CHNSDFRNRG MTALLKVSSC DKNTGDYYED SYEDISAYLL SKNNAIEPRS FSQNPPVLKR
HQREITRTTL QSDQEEIDYD DTISVEMKKE DFDIYDEDEN QSPRSFQKKT RHYFIAAVER LWDYGMSSSP
HVLRNRAQSG SVPQFKKVVF QEFTDGSFTQ PLYRGELNEH LGLLGPYIRA EVEDNIMVTF RNQASRPYSF
YSSLISYEED QRQGAEPRKN FVKPNETKTY FWKVQHHMAP TKDEFDCKAW AYFSDVDLEK DVHSGLIGPL
LVCHTNTLNP AHGRQVTVQE FALFFTIFDE TKSWYFTENM ERNCRAPCNI QMEDPTFKEN YRFHAINGYI
MDTLPGLVMA QDQRIRWYLL SMGSNENIHS IHFSGHVFTV RKKEEYKMAL YNLYPGVFET VEMLPSKAGI
WRVECLIGEH LHAGMSTLFL VYSNKCQTPL GMASGHIRDF QITASGQYGQ WAPKLARLHY SGSINAWSTK
EPFSWIKVDL LAPMIIHGIK TQGARQKFSS LYISQFIIMY SLDGKKWQTY RGNSTGTLMV FFGNVDSSGI
KHNIFNPPII ARYIRLHPTH YSIRSTLRME LMGCDLNSCS MPLGMESKAI SDAQITASSY FTNMFATWSP
SKARLHLQGR SNAWRPQVNN PKEWLQVDFQ KTMKVTGVTT QGVKSLLTSM YVKEFLISSS QDGHQWTLFF
QNGKVKVFQG NQDSFTPVVN SLDPPLLTRY LRIHPQSWVH QIALRMEVLG CEAQDLY

FIG. 3B (SEQ ID NO:9)

| SEQ ID NO:9 | Codon Optimized Nucleotide Sequence Encoding rhFVIII-BDD Protein of SEQ ID NO:8 |
|---|---|

ATGCAGATTG AGCTGAGCAC CTGTTTCTTC CTGTGCCTGC TGAGATTTTG CTTCTCAGCT ACCCGCAGGT
ACTACCTGGG AGCCGTTGAG CTGTCCTGGG ATTACATGCA GTCAGATCTG GGGGAGCTGC CTGTGGACGC
TCGGTTTCCC CCCAGAGTGC CAAAGTCCTT TCCCTTCAAC ACCAGCGTGG TGTACAAAAA GACACTTTTT
GTTGAATTTA CTGACCACTT GTTCAACATC GCCAAGCCAC GACCCCCATG GATGGGCCTG CTGGGGCCAA
CCATTCAGGC AGAGGTTTAC GACACAGTCG TGATCACACT GAAGAACATG GCCTCCCATC CAGTGTCTCT
GCACGCCGTC GGTGTGTCCT ACTGGAAAGC ATCCGAGGGC GCCGAGTATG ACGACCAGAC CAGCCAGAGA
GAGAAAGAGG ACGACAAAGT GTTCCCTGGA GGCAGCCACA CCTACGTGTG GCAGGTGTTG AAGGAAAATG
GGCCCATGGC CAGTGACCCT TTGTGTCTGA CTTACTCATA CCTGTCTCAT GTGGATCTAG TCAAGGACCT
GAATTCTGGA CTGATTGGGG CACTGCTTGT GTGCCGCGAA GGCAGCCTGG CCAAAGAAAA GACACAGACC
CTTCACAAGT TCATCCTGCT GTTCGCCGTG TTCGACGAAG GCAAATCCTG GCACTCAGAA ACCAAAAACT
CACTGATGCA GGACCGGGAT GCCGCCTCTG CCCGCGCATG GCCAAAAATG CACACCGTCA ACGGCTATGT
CAATAGAAGT TTGCCCGGCC TCATTGGATG TCACAGGAAA AGCGTCTATT GGCATGTAAT CGGGATGGGA
ACCACACCTG AGGTCCACAG CATATTTCTG GAAGGCCACA CATTTCTGGT GAGAAATCAT CGCCAGGCTT
CCCTGGAAAT TTCCCCCATC ACCTTCTTGA CCGCCCAGAC ACTGCTCATG GATCTTGGGC AGTTTCTGCT
GTTTTGTCAT ATTTCTTCTC ACCAACACGA CGGAATGGAG GCCTACGTTA AGGTCGATAG TTGCCCTGAA
GAACCTCAGC TGAGGATGAA GAACAACGAG GAAGCCGAGG ACTACGATGA CGATTTGACC GATTCCGAAA
TGGACGTGGT GCGCTTTGAT GATGACAATT CTCCATCCTT CATTCAGATT AGATCCGTCG CCAAGAAGCA
CCCCAAGACC TGGGTGCACT ACATTGCAGC CGAGGAGGAG GATTGGGACT ACGCCCCCCT GGTGCTGGCA
CCCGACGACC GAAGCTACAA ATCTCAGTAC CTGAACAATG GTCCACAACG GATCGGCAGG AAGTACAAGA
AAGTGCGGTT CATGGCCTAT ACAGACGAAA CCTTCAAAAC CAGGGAGGCT ATCCAGCACG AGTCTGGGAT
TCTGGGACCA CTCCTGTACG GCGAAGTGGG CGACACCTTG TTAATTATCT TCAAGAACCA GGCTAGTAGA
CCTTATAACA TTTATCCCCA CGGCATTACC GATGTGCGGC CTCTCTACTC TAGGCGGCTT CCAAAGGGGG
TGAAACACCT GAAGGACTTT CCCATCCTCC CTGGCGAAAT CTTTAAGTAT AAGTGGACAG TGACCGTGGA
GGATGGACCA ACCAAGAGCG ACCCCAGGTG CCTGACACGC TATTATTCAA GCTTCGTGAA TATGGAAAGG
GACCTCGCAT CTGGCTTGAT CGGCCCTCTG CTGATATGTT ACAAGGAAAG CGTCGATCAG AGAGGAAATC
AGATCATGTC AGACAAAAGG AATGTGATCC TGTTCTCCGT CTTCGATGAA AACAGGAGCT GGTATCTGAC
AGAGAACATC CAGAGATTCC TGCCAAATCC CGCCGGCGTC CAGCTGGAGG ACCCGGAGTT TCAGGCATCT
AACATCATGC ATTCCATTAA TGGTTACGTG TTCGACTCCC TGCAGCTGAG CGTGTGCCTC CACGAGGTGG
CCTACTGGTA CATCTTGAGC ATCGGCGCCC AGACCGACTT TCTGAGCGTC TTTTTCTCCG GGTATACTTT
CAAACATAAG ATGGTGTACG AAGATACTCT GACGCTGTTC CCTTTCTCTG GGGAGACTGT GTTTATGTCT
ATGGAGAACC CTGGACTGTG GATTCTCGGA TGCCACAACA GTGACTTTCG TAATAGAGGG ATGACTGCAC
TGCTGAAGGT GTCCAGCTGT GATAAAAATA CTGGCGACTA CTACGAAGAT AGCTATGAGG ATATCTCAGC
ATACCTGCTG AGCAAGAATA ACGCCATCGA GCCCCGAAGC TTCTCACAGA ATCCCCCTGT CCTCAAGAGG
CACCAGCGAG AGATCACAAG GACCACACTC CAGTCCGACC AGGAGGAGAT TGACTACGAT GACACGATTT
CTGTGGAGAT GAAAAAAGAG GACTTTGACA TCTACGATGA GGATGAAAAC CAGAGCCCTA GGTCGTTCCA

FIG. 3B continued

```
GAAGAAAACA AGGCACTACT TCATTGCCGC CGTGGAGAGA CTGTGGGACT ACGGAATGAG TAGTTCCCCA
CACGTGTTGC GGAACAGAGC CCAGAGTGGG TCCGTCCCAC AGTTCAAGAA GGTTGTTTTC CAGGAGTTCA
CAGATGGCTC CTTCACTCAG CCACTGTATC GCGGCGAGCT GAATGAGCAC TTGGGCTTAT TGGGCCCCTA
CATTCGCGCA GAAGTCGAAG ATAATATTAT GGTGACCTTC CGCAACCAGG CCAGCCGGCC TTACTCATTC
TACTCCTCTC TCATCTCTTA TGAGGAGGAT CAGCGCCAGG GCGCCGAACC CCGGAAGAAC TTTGTGAAGC
CCAATGAAAC CAAAACTTAC TTTTGGAAGG TGCAGCACCA TATGGCGCCG ACGAAAGACG AATTTGACTG
CAAAGCCTGG GCCTACTTCA GCGACGTCGA CTTGGAGAAG GACGTCCACA GCGGCCTGAT TGGCCCTTTG
TTGGTCTGCC ATACCAATAC ACTCAACCCT GCCCACGGGA GGCAGGTGAC CGTGCAGGAG TTTGCCTTGT
TCTTCACCAT CTTCGACGAA ACCAAGAGCT GGTACTTCAC AGAGAACATG GAGAGGAACT GCAGAGCACC
CTGTAACATC CAGATGGAGG ACCCTACTTT CAAGGAAAAT TACAGGTTCC ATGCCATTAA TGGCTACATC
ATGGATACCC TCCCCGGGCT TGTGATGGCT CAGGACCAGC GCATCCGCTG GTACCTGCTC TCAATGGGCT
CCAACGAGAA CATTCATAGC ATCCACTTTA GTGGCCACGT GTTTACCGTG CGCAAGAAGG AGGAGTACAA
GATGGCACTG TACAACCTGT ACCCTGGCGT GTTTGAGACA GTGGAGATGC TGCCATCCAA GGCCGGCATC
TGGCGCGTGG AGTGCCTCAT TGGGGAGCAC CTCCATGCTG GCATGTCTAC ACTGTTCCTG GTGTACAGCA
ACAAGTGTCA GACTCCACTC GGAATGGCCT CCGGGCATAT CCGCGATTTT CAGATCACGG CCTCTGGCCA
GTATGGCCAA TGGGCTCCCA AGCTGGCCAG GCTGCACTAC AGTGGGAGTA TCAACGCTTG GAGCACCAAG
GAGCCTTTCT CCTGGATCAA GGTGGACCTG CTTGCCCCCA TGATTATTCA CGGCATTAAG ACACAGGGGG
CCAGGCAGAA ATTCTCCTCC CTGTACATCT CCCAGTTCAT CATCATGTAC AGTCTGGACG GCAAAAAGTG
GCAGACCTAC CGCGGGAACA GTACCGGGAC ATTGATGGTG TTCTTCGGGA ACGTGGACTC TAGCGGCATT
AAACACAACA TTTTCAACCC CCCCATCATT GCTAGGTATA TCAGGCTCCA TCCCACCCAC TATAGCATCA
GGTCCACTCT GCGGATGGAG CTGATGGGCT GCGACCTTAA TTCATGCAGC ATGCCGCTGG GCATGGAGTC
AAAGGCCATC TCCGACGCCC AAATCACCGC CTCCAGCTAC TTCACCAATA TGTTCGCCAC CTGGAGCCCC
AGCAAGGCCC GGCTGCACCT GCAGGGCCGC AGCAACGCCT GGCGGCCTCA GGTGAACAAC CCCAAGGAGT
GGCTGCAGGT GGACTTCCAG AAAACCATGA AGGTGACTGG GGTCACCACC CAGGGAGTCA AGAGCCTGCT
GACCAGCATG TATGTGAAGG AGTTCTTGAT CAGCTCGTCA CAGGATGGCC ACCAGTGGAC TTTGTTCTTT
CAGAACGGTA AGGTGAAAGT GTTCCAGGGA AACCAAGATT CCTTTACACC AGTGGTCAAC TCTCTGGATC
CTCCCCTGCT GACACGGTAC CTGCGGATCC ATCCCCAGTC ATGGGTGCAC CAGATTGCTC TGCGCATGGA
GGTGCTTGGC TGCGAGGCCC AGGACCTGTA CTGA
```

FIG. 3C (SEQ ID NO:10)

| SEQ ID NO:10 | rhScFVIII-BDD 1 |
|---|---|

MQIELSTCFF LCLLRFCFSA TRRYYLGAVE LSWDYMQSDL GELPVDARFP PRVPKSFPFN TSVVYKKTLF
VEFTDHLFNI AKPRPPWMGL LGPTIQAEVY DTVVITLKNM ASHPVSLHAV GVSYWKASEG AEYDDQTSQR
EKEDDKVFPG GSHTYVWQVL KENGPMASDP LCLTYSYLSH VDLVKDLNSG LIGALLVCRE GSLAKEKTQT
LHKFILLFAV FDEGKSWHSE TKNSLMQDRD AASARAWPKM HTVNGYVNRS LPGLIGCHRK SVYWHVIGMG
TTPEVHSIFL EGHTFLVRNH RQASLEISPI TFLTAQTLLM DLGQFLLFCH ISSHQHDGME AYVKVDSCPE
EPQLRMKNNE EAEDYDDDLT DSEMDVVRFD DDNSPSFIQI RSVAKKHPKT WVHYIAAEEE DWDYAPLVLA
PDDRSYKSQY LNNGPQRIGR KYKKVRFMAY TDETFKTREA IQHESGILGP LLYGEVGDTL LIIFKNQASR
PYNIYPHGIT DVRPLYSRRL PKGVKHLKDF PILPGEIFKY KWTVTVEDGP TKSDPRCLTR YYSSFVNMER
DLASGLIGPL LICYKESVDQ RGNQIMSDKR NVILFSVFDE NRSWYLTENI QRFLPNPAGV QLEDPEFQAS
NIMHSINGYV FDSLQLSVCL HEVAYWYILS IGAQTDFLSV FFSGYTFKHK MVYEDTLTLF PFSGETVFMS
MENPGLWILG CHNSDFRNRG MTALLKVSSC DKNTGDYYED SYEDISAYLL SKNNAIEPRS FSQNPPVLKA
HQAEITRTTL QSDQEEIDYD DTISVEMKKE DFDIYDEDEN QSPRSFQKKT RHYFIAAVER LWDYGMSSSP
HVLRNRAQSG SVPQFKKVVF QEFTDGSFTQ PLYRGELNEH LGLLGPYIRA EVEDNIMVTF RNQASRPYSF
YSSLISYEED QRQGAEPRKN FVKPNETKTY FWKVQHHMAP TKDEFDCKAW AYFSDVDLEK DVHSGLIGPL
LVCHTNTLNP AHGRQVTVQE FALFFTIFDE TKSWYFTENM ERNCRAPCNI QMEDPTFKEN YRFHAINGYI
MDTLPGLVMA QDQRIRWYLL SMGSNENIHS IHFSGHVFTV RKKEEYKMAL YNLYPGVFET VEMLPSKAGI
WRVECLIGEH LHAGMSTLFL VYSNKCQTPL GMASGHIRDF QITASGQYGQ WAPKLARLHY SGSINAWSTK
EPFSWIKVDL LAPMIIHGIK TQGARQKFSS LYISQFIIMY SLDGKKWQTY RGNSTGTLMV FFGNVDSSGI
KHNIFNPPII ARYIRLHPTH YSIRSTLRME LMGCDLNSCS MPLGMESKAI SDAQITASSY FTNMFATWSP
SKARLHLQGR SNAWRPQVNN PKEWLQVDFQ KTMKVTGVTT QGVKSLLTSM YVKEFLISSS QDGHQWTLFF
QNGKVKVFQG NQDSFTPVVN SLDPPLLTRY LRIHPQSWVH QIALRMEVLG CEAQDLY

FIG. 3D (SEQ ID NO:11)

| SEQ ID NO:11 | Codon-Optimized Nucleotide Sequence Encoding rhScFVIII-BDD Protein of SEQ ID NO:10 |
|---|---|

ATGCAGATTG AGCTGAGCAC CTGTTTCTTC CTGTGCCTGC TGAGATTTTG CTTCTCAGCT ACCCGCAGGT
ACTACCTGGG AGCCGTTGAG CTGTCCTGGG ATTACATGCA GTCAGATCTG GGGGAGCTGC CTGTGGACGC
TCGGTTTCCC CCCAGAGTGC CAAAGTCCTT TCCCTTCAAC ACCAGCGTGG TGTACAAAAA GACACTTTTT
GTTGAATTTA CTGACCACTT GTTCAACATC GCCAAGCCAC GACCCCCATG GATGGGCCTG CTGGGGCCAA
CCATTCAGGC AGAGGTTTAC GACACAGTCG TGATCACACT GAAGAACATG GCCTCCCATC CAGTGTCTCT
GCACGCCGTC GGTGTGTCCT ACTGGAAAGC ATCCGAGGGC GCCGAGTATG ACGACCAGAC CAGCCAGAGA
GAGAAAGAGG ACGACAAAGT GTTCCCTGGA GGCAGCCACA CCTACGTGTG GCAGGTGTTG AAGGAAAATG
GGCCCATGGC CAGTGACCCT TTGTGTCTGA CTTACTCATA CCTGTCTCAT GTGGATCTAG TCAAGGACCT
GAATTCTGGA CTGATTGGGG CACTGCTTGT GTGCCGCGAA GGCAGCCTGG CCAAAGAAAA GACACAGACC
CTTCACAAGT TCATCCTGCT GTTCGCCGTG TTCGACGAAG GCAAATCCTG GCACTCAGAA ACCAAAAACT
CACTGATGCA GGACCGGGAT GCCGCCTCTG CCCGCGCATG GCCAAAAATG CACACCGTCA ACGGCTATGT
CAATAGAAGT TTGCCCGGCC TCATTGGATG TCACAGGAAA AGCGTCTATT GGCATGTAAT CGGGATGGGA
ACCACACCTG AGGTCCACAG CATATTTCTG GAAGGCCACA CATTTCTGGT GAGAAATCAT CGCCAGGCTT
CCCTGGAAAT TTCCCCCATC ACCTTCTTGA CCGCCCAGAC ACTGCTCATG GATCTTGGGC AGTTTCTGCT
GTTTTGTCAT ATTTCTTCTC ACCAACACGA CGGAATGGAG GCCTACGTTA AGGTCGATAG TTGCCCTGAA
GAACCTCAGC TGAGGATGAA GAACAACGAG GAAGCCGAGG ACTACGATGA CGATTTGACC GATTCCGAAA
TGGACGTGGT GCGCTTTGAT GATGACAATT CTCCATCCTT CATTCAGATT AGATCCGTCG CCAAGAAGCA
CCCCAAGACC TGGGTGCACT ACATTGCAGC CGAGGAGGAG GATTGGGACT ACGCCCCCCT GGTGCTGGCA
CCCGACGACC GAAGCTACAA ATCTCAGTAC CTGAACAATG GTCCACAACG GATCGGCAGG AAGTACAAGA
AAGTGCGGTT CATGGCCTAT ACAGACGAAA CCTTCAAAAC CAGGGAGGCT ATCCAGCACG AGTCTGGGAT
TCTGGGACCA CTCCTGTACG GCGAAGTGGG CGACACCTTG TTAATTATCT TCAAGAACCA GGCTAGTAGA
CCTTATAACA TTTATCCCCA CGGCATTACC GATGTGCGGC CTCTCTACTC TAGGCGGCTT CCAAAGGGGG
TGAAACACCT GAAGGACTTT CCCATCCTCC CTGGCGAAAT CTTTAAGTAT AAGTGGACAG TGACCGTGGA
GGATGGACCA ACCAAGAGCG ACCCCAGGTG CCTGACACGC TATTATTCAA GCTTCGTGAA TATGGAAAGG
GACCTCGCAT CTGGCTTGAT CGGCCCTCTG CTGATATGTT ACAAGGAAAG CGTCGATCAG AGAGGAAATC
AGATCATGTC AGACAAAAGG AATGTGATCC TGTTCTCCGT CTTCGATGAA AACAGGAGCT GGTATCTGAC
AGAGAACATC CAGAGATTCC TGCCAAATCC CGCCGGCGTC CAGCTGGAGG ACCCGGAGTT TCAGGCATCT
AACATCATGC ATTCCATTAA TGGTTACGTG TTCGACTCCC TGCAGCTGAG CGTGTGCCTC CACGAGGTGG
CCTACTGGTA CATCTTGAGC ATCGGCGCCC AGACCGACTT TCTGAGCGTC TTTTTCTCCG GGTATACTTT
CAAACATAAG ATGGTGTACG AAGATACTCT GACGCTGTTC CCTTTCTCTG GGGAGACTGT GTTTATGTCT
ATGGAGAACC CTGGACTGTG GATTCTCGGA TGCCACAACA GTGACTTTCG TAATAGAGGG ATGACTGCAC
TGCTGAAGGT GTCCAGCTGT GATAAAAATA CTGGCGACTA CTACGAAGAT AGCTATGAGG ATATCTCAGC
ATACCTGCTG AGCAAGAATA ACGCCATCGA GCCCCGAAGC TTCTCACAGA ATCCCCCTGT CCTCAAGGCC
CACCAGGCGG AGATCACAAG GACCACACTC CAGTCCGACC AGGAGGAGAT TGACTACGAT GACACGATTT
CTGTGGAGAT GAAAAAAGAG GACTTTGACA TCTACGATGA GGATGAAAAC CAGAGCCCTA GGTCGTTCCA

FIG. 3D continued

GAAGAAAACA AGGCACTACT TCATTGCCGC CGTGGAGAGA CTGTGGGACT ACGGAATGAG TAGTTCCCCA
CACGTGTTGC GGAACAGAGC CCAGAGTGGG TCCGTCCCAC AGTTCAAGAA GGTTGTTTTC CAGGAGTTCA
CAGATGGCTC CTTCACTCAG CCACTGTATC GCGGCGAGCT GAATGAGCAC TTGGGCTTAT TGGGCCCCTA
CATTCGCGCA GAAGTCGAAG ATAATATTAT GGTGACCTTC CGCAACCAGG CCAGCCGGCC TTACTCATTC
TACTCCTCTC TCATCTCTTA TGAGGAGGAT CAGCGCCAGG GCGCCGAACC CCGGAAGAAC TTTGTGAAGC
CCAATGAAAC CAAAACTTAC TTTTGGAAGG TGCAGCACCA TATGGCGCCG ACGAAAGACG AATTTGACTG
CAAAGCCTGG GCCTACTTCA GCGACGTCGA CTTGGAGAAG GACGTCCACA GCGGCCTGAT TGGCCCTTTG
TTGGTCTGCC ATACCAATAC ACTCAACCCT GCCCACGGGA GGCAGGTGAC CGTGCAGGAG TTTGCCTTGT
TCTTCACCAT CTTCGACGAA ACCAAGAGCT GGTACTTCAC AGAGAACATG GAGAGGAACT GCAGAGCACC
CTGTAACATC CAGATGGAGG ACCCTACTTT CAAGGAAAAT TACAGGTTCC ATGCCATTAA TGGCTACATC
ATGGATACCC TCCCCGGGCT TGTGATGGCT CAGGACCAGC GCATCCGCTG GTACCTGCTC TCAATGGGCT
CCAACGAGAA CATTCATAGC ATCCACTTTA GTGGCCACGT GTTTACCGTG CGCAAGAAGG AGGAGTACAA
GATGGCACTG TACAACCTGT ACCCTGGCGT GTTTGAGACA GTGGAGATGC TGCCATCCAA GGCCGGCATC
TGGCGCGTGG AGTGCCTCAT TGGGGAGCAC CTCCATGCTG GCATGTCTAC ACTGTTCCTG GTGTACAGCA
ACAAGTGTCA GACTCCACTC GGAATGGCCT CCGGGCATAT CCGCGATTTT CAGATCACGG CCTCTGGCCA
GTATGGCCAA TGGGCTCCCA AGCTGGCCAG GCTGCACTAC AGTGGGAGTA TCAACGCTTG GAGCACCAAG
GAGCCTTTCT CCTGGATCAA GGTGGACCTG CTTGCCCCCA TGATTATTCA CGGCATTAAG ACACAGGGGG
CCAGGCAGAA ATTCTCCTCC CTGTACATCT CCCAGTTCAT CATCATGTAC AGTCTGGACG GCAAAAAGTG
GCAGACCTAC CGCGGGAACA GTACCGGGAC ATTGATGGTG TTCTTCGGGA ACGTGGACTC TAGCGGCATT
AAACACAACA TTTTCAACCC CCCCATCATT GCTAGGTATA TCAGGCTCCA TCCCACCCAC TATAGCATCA
GGTCCACTCT GCGGATGGAG CTGATGGGCT GCGACCTTAA TTCATGCAGC ATGCCGCTGG GCATGGAGTC
AAAGGCCATC TCCGACGCCC AAATCACCGC CTCCAGCTAC TTCACCAATA TGTTCGCCAC CTGGAGCCCC
AGCAAGGCCC GGCTGCACCT GCAGGGCCGC AGCAACGCCT GGCGGCCTCA GGTGAACAAC CCCAAGGAGT
GGCTGCAGGT GGACTTCCAG AAAACCATGA AGGTGACTGG GGTCACCACC CAGGGAGTCA AGAGCCTGCT
GACCAGCATG TATGTGAAGG AGTTCTTGAT CAGCTCGTCA CAGGATGGCC ACCAGTGGAC TTTGTTCTTT
CAGAACGGTA AGGTGAAAGT GTTCCAGGGA AACCAAGATT CCTTTACACC AGTGGTCAAC TCTCTGGATC
CTCCCCTGCT GACACGGTAC CTGCGGATCC ATCCCCAGTC ATGGGTGCAC CAGATTGCTC TGCGCATGGA
GGTGCTTGGC TGCGAGGCCC AGGACCTGTA CTGA

FIG. 3E (SEQ ID NO:12)

| SEQ ID NO:12 | rhScFVIII-BDD 2 |
|---|---|

MQIELSTCFF LCLLRFCFSA TRRYYLGAVE LSWDYMQSDL GELPVDARFP PRVPKSFPFN TSVVYKKTLF
VEFTDHLFNI AKPRPPWMGL LGPTIQAEVY DTVVITLKNM ASHPVSLHAV GVSYWKASEG AEYDDQTSQR
EKEDDKVFPG GSHTYVWQVL KENGPMASDP LCLTYSYLSH VDLVKDLNSG LIGALLVCRE GSLAKEKTQT
LHKFILLFAV FDEGKSWHSE TKNSLMQDRD AASARAWPKM HTVNGYVNRS LPGLIGCHRK SVYWHVIGMG
TTPEVHSIFL EGHTFLVRNH RQASLEISPI TFLTAQTLLM DLGQFLLFCH ISSHQHDGME AYVKVDSCPE
EPQLRMKNNE EAEDYDDDLT DSEMDVVRFD DDNSPSFIQI RSVAKKHPKT WVHYIAAEEE DWDYAPLVLA
PDDRSYKSQY LNNGPQRIGR KYKKVRFMAY TDETFKTREA IQHESGILGP LLYGEVGDTL LIIFKNQASR
PYNIYPHGIT DVRPLYSRRL PKGVKHLKDF PILPGEIFKY KWTVTVEDGP TKSDPRCLTR YYSSFVNMER
DLASGLIGPL LICYKESVDQ RGNQIMSDKR NVILFSVFDE NRSWYLTENI QRFLPNPAGV QLEDPEFQAS
NIMHSINGYV FDSLQLSVCL HEVAYWYILS IGAQTDFLSV FFSGYTFKHK MVYEDTLTLF PFSGETVFMS
MENPGLWILG CHNSDFRNRG MTALLKVSSC DKNTGDYYED SYEDISAYLL SKNNAIEPRS FSQNPPVLKH
HQREITRTTL QSDQEEIDYD DTISVEMKKE DFDIYDEDEN QSPRSFQKKT RHYFIAAVER LWDYGMSSSP
HVLRNRAQSG SVPQFKKVVF QEFTDGSFTQ PLYRGELNEH LGLLGPYIRA EVEDNIMVTF RNQASRPYSF
YSSLISYEED QRQGAEPRKN FVKPNETKTY FWKVQHHMAP TKDEFDCKAW AYFSDVDLEK DVHSGLIGPL
LVCHTNTLNP AHGRQVTVQE FALFFTIFDE TKSWYFTENM ERNCRAPCNI QMEDPTFKEN YRFHAINGYI
MDTLPGLVMA QDQRIRWYLL SMGSNENIHS IHFSGHVFTV RKKEEYKMAL YNLYPGVFET VEMLPSKAGI
WRVECLIGEH LHAGMSTLFL VYSNKCQTPL GMASGHIRDF QITASGQYGQ WAPKLARLHY SGSINAWSTK
EPFSWIKVDL LAPMIIHGIK TQGARQKFSS LYISQFIIMY SLDGKKWQTY RGNSTGTLMV FFGNVDSSGI
KHNIFNPPII ARYIRLHPTH YSIRSTLRME LMGCDLNSCS MPLGMESKAI SDAQITASSY FTNMFATWSP
SKARLHLQGR SNAWRPQVNN PKEWLQVDFQ KTMKVTGVTT QGVKSLLTSM YVKEFLISSS QDGHQWTLFF
QNGKVKVFQG NQDSFTPVVN SLDPPLLTRY LRIHPQSWVH QIALRMEVLG CEAQDLY

FIG. 3F (SEQ ID NO:13)

| SEQ ID NO:13 | rhScFVIII-BDD 3 (ΔF) |
|---|---|
| MQIELSTCFF LCLLRFCFSA TRRYYLGAVE LSWDYMQSDL GELPVDARFP PRVPKSFPFN TSVVYKKTLF VEFTDHLFNI AKPRPPWMGL LGPTIQAEVY DTVVITLKNM ASHPVSLHAV GVSYWKASEG AEYDDQTSQR EKEDDKVFPG GSHTYVWQVL KENGPMASDP LCLTYSYLSH VDLVKDLNSG LIGALLVCRE GSLAKEKTQT LHKFILLFAV FDEGKSWHSE TKNSLMQDRD AASARAWPKM HTVNGYVNRS LPGLIGCHRK SVYWHVIGMG TTPEVHSIFL EGHTFLVRNH RQASLEISPI TFLTAQTLLM DLGQFLLFCH ISSHQHDGME AYVKVDSCPE EPQLRMKNNE EAEDYDDDLT DSEMDVVRFD DDNSPSFIQI RSVAKKHPKT WVHYIAAEEE DWDYAPLVLA PDDRSYKSQY LNNGPQRIGR KYKKVRFMAY TDETFKTREA IQHESGILGP LLYGEVGDTL LIIFKNQASR PYNIYPHGIT DVRPLYSRRL PKGVKHLKDF PILPGEIFKY KWTVTVEDGP TKSDPRCLTR YYSSFVNMER DLASGLIGPL LICYKESVDQ RGNQIMSDKR NVILFSVFDE NRSWYLTENI QRFLPNPAGV QLEDPEFQAS NIMHSINGYV FDSLQLSVCL HEVAYWYILS IGAQTDFLSV FFSGYTFKHK MVYEDTLTLF PFSGETVFMS MENPGLWILG CHNSDFRNRG MTALLKVSSC DKNTGDYYED SYEDISAYLL SKNNAIEPRS FSQNPPVLKE ITRTTLQSDQ EEIDYDDTIS VEMKKEDFDI YDEDENQSPR SFQKKTRHYF IAAVERLWDY GMSSSPHVLR NRAQSGSVPQ FKKVVFQEFT DGSFTQPLYR GELNEHLGLL GPYIRAEVED NIMVTFRNQA SRPYSFYSSL ISYEEDQRQG AEPRKNFVKP NETKTYFWKV QHHMAPTKDE FDCKAWAYFS DVDLEKDVHS GLIGPLLVCH TNTLNPAHGR QVTVQEFALF FTIFDETKSW YFTENMERNC RAPCNIQMED PTFKENYRFH AINGYIMDTL PGLVMAQDQR IRWYLLSMGS NENIHSIHFS GHVFTVRKKE EYKMALYNLY PGVFETVEML PSKAGIWRVE CLIGEHLHAG MSTLFLVYSN KCQTPLGMAS GHIRDFQITA SGQYGQWAPK LARLHYSGSI NAWSTKEPFS WIKVDLLAPM IIHGIKTQGA RQKFSSLYIS QFIIMYSLDG KKWQTYRGNS TGTLMVFFGN VDSSGIKHNI FNPPIIARYI RLHPTHYSIR STLRMELMGC DLNSCSMPLG MESKAISDAQ ITASSYFTNM FATWSPSKAR LHLQGRSNAW RPQVNNPKEW LQVDFQKTMK VTGVTTQGVK SLLTSMYVKE FLISSSQDGH QWTLFFQNGK VKVFQGNQDS FTPVVNSLDP PLLTRYLRIH PQSWVHQIAL RMEVLGCEAQ DLY | |

FIG. 3G (SEQ ID NO:14)

| SEQ ID NO:14 | rhScFVIII-BDD 4 |
|---|---|

MQIELSTCFF LCLLRFCFSA TRRYYLGAVE LSWDYMQSDL GELPVDARFP PRVPKSFPFN TSVVYKKTLF
VEFTDHLFNI AKPRPPWMGL LGPTIQAEVY DTVVITLKNM ASHPVSLHAV GVSYWKASEG AEYDDQTSQR
EKEDDKVFPG GSHTYVWQVL KENGPMASDP LCLTYSYLSH VDLVKDLNSG LIGALLVCRE GSLAKEKTQT
LHKFILLFAV FDEGKSWHSE TKNSLMQDRD AASARAWPKM HTVNGYVNRS LPGLIGCHRK SVYWHVIGMG
TTPEVHSIFL EGHTFLVRNH RQASLEISPI TFLTAQTLLM DLGQFLLFCH ISSHQHDGME AYVKVDSCPE
EPQLRMKNNE EAEDYDDDLT DSEMDVVRFD DDNSPSFIQI RSVAKKHPKT WVHYIAAEEE DWDYAPLVLA
PDDRSYKSQY LNNGPQRIGR KYKKVRFMAY TDETFKTREA IQHESGILGP LLYGEVGDTL LIIFKNQASR
PYNIYPHGIT DVRPLYSRRL PKGVKHLKDF PILPGEIFKY KWTVTVEDGP TKSDPRCLTR YYSSFVNMER
DLASGLIGPL LICYKESVDQ RGNQIMSDKR NVILFSVFDE NRSWYLTENI QRFLPNPAGV QLEDPEFQAS
NIMHSINGYV FDSLQLSVCL HEVAYWYILS IGAQTDFLSV FFSGYTFKHK MVYEDTLTLF PFSGETVFMS
MENPGLWILG CHNSDFRNRG MTALLKVSSC DKNTGDYYED SYEDISAYLL SKNNAIEPRS FSQNPPVLKR
EITRTTLQSD QEEIDYDDTI SVEMKKEDFD IYDEDENQSP RSFQKKTRHY FIAAVERLWD YGMSSSPHVL
RNRAQSGSVP QFKKVVFQEF TDGSFTQPLY RGELNEHLGL LGPYIRAEVE DNIMVTFRNQ ASRPYSFYSS
LISYEEDQRQ GAEPRKNFVK PNETKTYFWK VQHHMAPTKD EFDCKAWAYF SDVDLEKDVH SGLIGPLLVC
HTNTLNPAHG RQVTVQEFAL FFTIFDETKS WYFTENMERN CRAPCNIQME DPTFKENYRF HAINGYIMDT
LPGLVMAQDQ RIRWYLLSMG SNENIHSIHF SGHVFTVRKK EEYKMALYNL YPGVFETVEM LPSKAGIWRV
ECLIGEHLHA GMSTLFLVYS NKCQTPLGMA SGHIRDFQIT ASGQYGQWAP KLARLHYSGS INAWSTKEPF
SWIKVDLLAP MIIHGIKTQG ARQKFSSLYI SQFIIMYSLD GKKWQTYRGN STGTLMVFFG NVDSSGIKHN
IFNPPIIARY IRLHPTHYSI RSTLRMELMG CDLNSCSMPL GMESKAISDA QITASSYFTN MFATWSPSKA
RLHLQGRSNA WRPQVNNPKE WLQVDFQKTM KVTGVTTQGV KSLLTSMYVK EFLISSSQDG HQWTLFFQNG
KVKVFQGNQD SFTPVVNSLD PPLLTRYLRI HPQSWVHQIA LRMEVLGCEA QDLY

FIG. 3H (SEQ ID NO:15)

| SEQ ID NO:15 | rhFVIII-BDD-addback Protein |
|---|---|

MQIELSTCFF LCLLRFCFSA TRRYYLGAVE LSWDYMQSDL GELPVDARFP PRVPKSFPFN TSVVYKKTLF
VEFTDHLFNI AKPRPPWMGL LGPTIQAEVY DTVVITLKNM ASHPVSLHAV GVSYWKASEG AEYDDQTSQR
EKEDDKVFPG GSHTYVWQVL KENGPMASDP LCLTYSYLSH VDLVKDLNSG LIGALLVCRE GSLAKEKTQT
LHKFILLFAV FDEGKSWHSE TKNSLMQDRD AASARAWPKM HTVNGYVNRS LPGLIGCHRK SVYWHVIGMG
TTPEVHSIFL EGHTFLVRNH RQASLEISPI TFLTAQTLLM DLGQFLLFCH ISSHQHDGME AYVKVDSCPE
EPQLRMKNNE EAEDYDDDLT DSEMDVVRFD DDNSPSFIQI RSVAKKHPKT WVHYIAAEEE DWDYAPLVLA
PDDRSYKSQY LNNGPQRIGR KYKKVRFMAY TDETFKTREA IQHESGILGP LLYGEVGDTL LIIFKNQASR
PYNIYPHGIT DVRPLYSRRL PKGVKHLKDF PILPGEIFKY KWTVTVEDGP TKSDPRCLTR YYSSFVNMER
DLASGLIGPL LICYKESVDQ RGNQIMSDKR NVILFSVFDE NRSWYLTENI QRFLPNPAGV QLEDPEFQAS
NIMHSINGYV FDSLQLSVCL HEVAYWYILS IGAQTDFLSV FFSGYTFKHK MVYEDTLTLF PFSGETVFMS
MENPGLWILG CHNSDFRNRG MTALLKVSSC DKNTGDYYED SYEDISAYLL SKNNAIEPRS FSQNATNVSN
NSNTSNDSNV SPPVLKRHQR EITRTTLQSD QEEIDYDDTI SVEMKKEDFD IYDEDENQSP RSFQKKTRHY
FIAAVERLWD YGMSSSPHVL RNRAQSGSVP QFKKVVFQEF TDGSFTQPLY RGELNEHLGL LGPYIRAEVE
DNIMVTFRNQ ASRPYSFYSS LISYEEDQRQ GAEPRKNFVK PNETKTYFWK VQHHMAPTKD EFDCKAWAYF
SDVDLEKDVH SGLIGPLLVC HTNTLNPAHG RQVTVQEFAL FFTIFDETKS WYFTENMERN CRAPCNIQME
DPTFKENYRF HAINGYIMDT LPGLVMAQDQ RIRWYLLSMG SNENIHSIHF SGHVFTVRKK EEYKMALYNL
YPGVFETVEM LPSKAGIWRV ECLIGEHLHA GMSTLFLVYS NKCQTPLGMA SGHIRDFQIT ASGQYGQWAP
KLARLHYSGS INAWSTKEPF SWIKVDLLAP MIIHGIKTQG ARQKFSSLYI SQFIIMYSLD GKKWQTYRGN
STGTLMVFFG NVDSSGIKHN IFNPPIIARY IRLHPTHYSI RSTLRMELMG CDLNSCSMPL GMESKAISDA
QITASSYFTN MFATWSPSKA RLHLQGRSNA WRPQVNNPKE WLQVDFQKTM KVTGVTTQGV KSLLTSMYVK
EFLISSSQDG HQWTLFFQNG KVKVFQGNQD SFTPVVNSLD PPLLTRYLRI HPQSWVHQIA LRMEVLGCEA
QDLY

FIG. 4A (SEQ ID NO:16)

| SEQ ID NO:16 | FIX-Padua Protein |
|---|---|
| MQRVNMIMAE SPGLITICLL GYLLSAECTV FLDHENANKI LNRPKRYNSG KLEEFVQGNL ERECMEEKCS<br>FEEAREVFEN TERTTEFWKQ YVDGDQCESN PCLNGGSCKD DINSYECWCP FGFEGKNCEL DVTCNIKNGR<br>CEQFCKNSAD NKVVCSCTEG YRLAENQKSC EPAVPFPCGR VSVSQTSKLT RAETVFPDVD YVNSTEAETI<br>LDNITQSTQS FNDFTRVVGG EDAKPGQFPW QVVLNGKVDA FCGGSIVNEK WIVTAAHCVE TGVKITVVAG<br>EHNIEETEHT EQKRNVIRII PHHNYNAAIN KYNHDIALLE LDEPLVLNSY VTPICIADKE YTNIFLKFGS<br>GYVSGWGRVF HKGRSALVLQ YLRVPLVDRA TCLLSTKFTI YNNMFCAGFH EGGRDSCQGD SGGPHVTEVE<br>GTSFLTGIIS WGEECAMKGK YGIYTKVSRY VNWIKEKTKL T | |

FIG. 4B (SEQ ID NO:17)

| SEQ ID NO:17 | Codon-optimized Nucleotide Sequence Encoding FIX-Padua Protein of SEQ ID NO:16 |
|---|---|

ATGCAGCGCG TGAACATGAT TATGGCCGAG TCTCCCGGCC TGATCACCAT CTGTCTGCTG GGCTATCTGC
TGAGCGCCGA GTGCACCGTG TTTCTGGATC ACGAGAACGC CAACAAGATC CTGAACAGAC CCAAGCGGTA
CAACAGCGGC AAGCTGGAAG AGTTCGTGCA GGGCAACCTG GAACGCGAGT GCATGGAAGA GAAGTGCAGC
TTCGAAGAGG CCAGAGAGGT GTTCGAGAAC ACCGAGAGAA CCACCGAGTT CTGGAAGCAG TACGTGGACG
GCGATCAGTG CGAGAGCAAC CCTTGTCTGA ATGGCGGCAG CTGCAAGGAC GACATCAACA GCTACGAGTG
CTGGTGCCCC TTCGGCTTCG AGGGCAAGAA TTGCGAGCTG GACGTGACCT GCAACATCAA GAACGGCAGA
TGCGAGCAGT TCTGCAAGAA CAGCGCCGAC AACAAGGTCG TGTGCTCCTG CACAGAGGGC TACAGACTGG
CCGAGAACCA GAAGTCTTGC GAGCCCGCTG TGCCCTTTCC ATGTGGCAGA GTGTCTGTGT CCCAGACCAG
CAAGCTGACC AGAGCCGAGA CAGTGTTCCC CGACGTGGAC TACGTGAACA GCACCGAGGC CGAGACAATC
CTGGACAACA TCACCCAGAG CACCCAGTCC TTCAACGACT TCACCAGAGT CGTCGGCGGC GAGGATGCTA
AGCCTGGACA GTTTCCTTGG CAAGTGGTGC TGAACGGCAA GGTGGACGCT TTTTGTGGCG GCTCCATCGT
GAACGAGAAG TGGATCGTGA CCGCCGCTCA CTGTGTGGAA ACCGGCGTGA AGATTACAGT GGTGGCCGGC
GAGCACAACA TCGAGGAAAC AGAGCACACC GAGCAGAAAC GGAACGTGAT CAGAATCATC CCTCACCACA
ACTACAACGC CGCCATCAAC AAGTACAACC ACGATATCGC CCTGCTGGAA CTGGACGAGC CCCTGGTCCT
GAACTCTTAC GTGACCCCTA TCTGTATCGC CGACAAAGAG TACACCAACA TCTTTCTGAA GTTCGGCAGC
GGCTACGTGT CCGGCTGGGG AAGAGTTTTC CACAAGGGCA GATCAGCCCT GGTGCTGCAG TACCTGAGAG
TGCCCCTGGT GGATAGAGCC ACATGCCTGC TGAGCACCAA GTTCACCATC TACAACAACA TGTTCTGCGC
CGGCTTCCAC GAAGGCGGCA GAGATTCTTG TCAAGGCGAT TCTGGCGGCC CTCACGTGAC AGAGGTTGAG
GGCACAAGCT TTCTGACCGG CATCATCAGC TGGGGCGAAG AGTGTGCCAT GAAGGGGAAG TACGGCATCT
ACACCAAGGT GTCCAGATAC GTGAACTGGA TCAAAGAAAA GACCAAGCTC ACCTGA

FIG. 5A (SEQ ID NO:18)

| SEQ ID NO:18 | Wild-type human precursor FVII Protein |
|---|---|
| MVSQALRLLC LLLGLQGCLA AGGVAKASGG ETRDMPWKPG PHRVFVTQEE AHGVLHRRRR ANAFLEELRP GSLERECKEE QCSFEEAREI FKDAERTKLF WISYSDGDQC ASSPCQNGGS CKDQLQSYIC FCLPAFEGRN CETHKDDQLI CVNENGGCEQ YCSDHTGTKR SCRCHEGYSL LADGVSCTPT VEYPCGKIPI LEKRNASKPQ GRIVGGKVCP KGECPWQVLL LVNGAQLCGG TLINTIWVVS AAHCFDKIKN WRNLIAVLGE HDLSEHDGDE QSRRVAQVII PSTYVPGTTN HDIALLRLHQ PVVLTDHVVP LCLPERTFSE RTLAFVRFSL VSGWGQLLDR GATALELMVL NVPRLMTQDC LQQSRKVGDS PNITEYMFCA GYSDGSKDSC KGDSGGPHAT HYRGTWYLTG IVSWGQGCAT VGHFGVYTRV SQYIEWLQKL MRSEPRPGVL LRAPFP | |

FIG. 5B (SEQ ID NO:19)

| SEQ ID NO:19 | Codon-optimized Nucleotide Sequence Encoding FVII Protein of SEQ ID NO:18 |
|---|---|

ATGGTGTCAC AGGCCCTGAG ACTGCTGTGT CTGCTGCTGG GACTGCAGGG ATGTTTGGCT GCTGGCGGAG
TGGCTAAAGC CTCTGGCGGA GAGACAAGAG ACATGCCCTG GAAGCCTGGA CCTCACAGAG TGTTCGTGAC
CCAAGAGGAA GCCCACGGCG TTCTGCACAG AAGAAGAAGG GCCAACGCCT TCCTGGAAGA ACTGAGGCCT
GGCTCTCTGG AACGCGAGTG CAAAGAGGAA CAGTGCAGCT TCGAGGAAGC CAGAGAGATC TTCAAGGACG
CCGAGCGGAC CAAGCTGTTC TGGATCAGCT ACAGCGACGG CGACCAGTGT GCCAGCTCTC CTTGTCAGAA
TGGCGGCAGC TGCAAGGACC AGCTGCAGAG CTACATCTGC TTTTGCCTGC CTGCCTTCGA GGGCAGAAAC
TGCGAGACAC ACAAGGACGA CCAGCTGATC TGCGTGAACG AGAACGGCGG CTGCGAGCAG TACTGTAGCG
ATCACACAGG CACCAAGCGG AGCTGCAGAT GTCACGAGGG CTATTCCCTG CTGGCCGATG GCGTTAGCTG
TACCCCTACC GTGGAATACC CCTGCGGCAA GATCCCCATC CTGGAAAAGA GAAACGCCAG CAAGCCCCAG
GGCAGAATCG TTGGCGGCAA AGTGTGCCCT AAGGGCGAGT GTCCTTGGCA GGTTCTGCTG CTTGTGAATG
GCGCTCAGCT GTGTGGCGGC ACCCTGATCA ATACCATCTG GGTCGTGTCC GCCGCTCACT GCTTCGACAA
GATCAAGAAC TGGCGGAACC TGATCGCCGT GCTGGGAGAG CACGATCTGT CTGAACACGA TGGCGACGAG
CAGTCTCGGA GAGTGGCCCA AGTGATCATC CCCAGCACCT ATGTGCCCGG CACCACCAAT CACGATATCG
CCCTGCTCAG ACTGCACCAG CCTGTGGTGC TGACAGATCA CGTGGTGCCT CTGTGCCTGC CAGAGAGGAC
CTTTAGCGAG AGAACCCTGG CCTTCGTGCG GTTCTCTCTG GTGTCTGGAT GGGGCCAGCT GCTGGATAGA
GGCGCTACAG CTCTGGAACT GATGGTGCTG AACGTGCCCA GACTGATGAC CCAGGATTGC CTGCAGCAGA
GCAGAAAAGT GGGCGACAGC CCCAACATCA CCGAGTACAT GTTCTGCGCC GGCTACTCCG ACGGCAGCAA
GGATAGCTGT AAAGGCGATT CTGGCGGCCC TCACGCCACA CACTATAGAG GCACCTGGTA TCTGACCGGC
ATCGTGTCTT GGGGACAGGG CTGTGCTACA GTGGGCCACT TTGGCGTGTA CACCAGAGTG TCCCAGTACA
TCGAGTGGCT GCAGAAACTC ATGCGGAGCG AGCCTAGACC TGGCGTGTTG CTGAGAGCCC CTTTTCCTTA
A

FIG. 5C (SEQ ID NO:20)

| SEQ ID NO:20 | Codon-optimized Nucleotide Sequence Encoding FVII Protein of SEQ ID NO:18 |
|---|---|
| ATGGTGAGCC AGGCCCTGCG CCTGCTGTGC CTGCTGCTGG GCCTGCAGGG CTGCCTGGCC GCCGGCGGCG<br>TGGCCAAGGC CAGCGGCGGC GAGACCCGCG ACATGCCCTG GAAGCCCGGC CCCCACCGCG TGTTCGTGAC<br>CCAGGAGGAG GCCCACGGCG TGCTGCACCG CCGCCGCCGC GCCAACGCCT TCCTGGAGGA GCTGCGCCCC<br>GGCAGCCTGG AGCGCGAGTG CAAGGAGGAG CAGTGCAGCT TCGAGGAGGC CCGCGAGATC TTCAAGGACG<br>CCGAGCGCAC CAAGCTGTTC TGGATCAGCT ACAGCGACGG CGACCAGTGC GCCAGCAGCC CCTGCCAGAA<br>CGGCGGCAGC TGCAAGGACC AGCTGCAGAG CTACATCTGC TTCTGCCTGC CCGCCTTCGA GGGCCGCAAC<br>TGCGAGACCC ACAAGGACGA CCAGCTGATC TGCGTGAACG AGAACGGCGG CTGCGAGCAG TACTGCAGCG<br>ACCACACCGG CACCAAGCGC AGCTGCCGCT GCCACGAGGG CTACAGCCTG CTGGCCGACG GCGTGAGCTG<br>CACCCCCACC GTGGAGTACC CCTGCGGCAA GATCCCCATC CTGGAGAAGC GCAACGCCAG CAAGCCCCAG<br>GGCCGCATCG TGGGCGGCAA GGTGTGCCCC AAGGGCGAGT GCCCCTGGCA GGTGCTGCTG CTGGTGAACG<br>GCGCCCAGCT GTGCGGCGGC ACCCTGATCA ACACCATCTG GGTGGTGAGC GCCGCCCACT GCTTCGACAA<br>GATCAAGAAC TGGCGCAACC TGATCGCCGT GCTGGGCGAG CACGACCTGA GCGAGCACGA CGGCGACGAG<br>CAGAGCCGCC GCGTGGCCCA GGTGATCATC CCCAGCACCT ACGTGCCCGG CACCACCAAC CACGACATCG<br>CCCTGCTGCG CCTGCACCAG CCCGTGGTGC TGACCGACCA CGTGGTGCCC CTGTGCCTGC CCGAGCGCAC<br>CTTCAGCGAG CGCACCCTGG CCTTCGTGCG CTTCAGCCTG GTGAGCGGCT GGGGCCAGCT GCTGGACCGC<br>GGCGCCACCG CCCTGGAGCT GATGGTGCTG AACGTGCCCC GCCTGATGAC CCAGGACTGC CTGCAGCAGA<br>GCCGCAAGGT GGGCGACAGC CCCAACATCA CCGAGTACAT GTTCTGCGCC GGCTACAGCG ACGGCAGCAA<br>GGACAGCTGC AAGGGCGACA GCGGCGGCCC CCACGCCACC CACTACCGCG GCACCTGGTA CCTGACCGGC<br>ATCGTGAGCT GGGGCCAGGG CTGCGCCACC GTGGGCCACT TCGGCGTGTA CACCCGCGTG AGCCAGTACA<br>TCGAGTGGCT GCAGAAGCTG ATGCGCAGCG AGCCCCGCCC CGGCGTGCTG CTGCGCGCCC CCTTCCCCTA<br>A | |

Figure 6A:
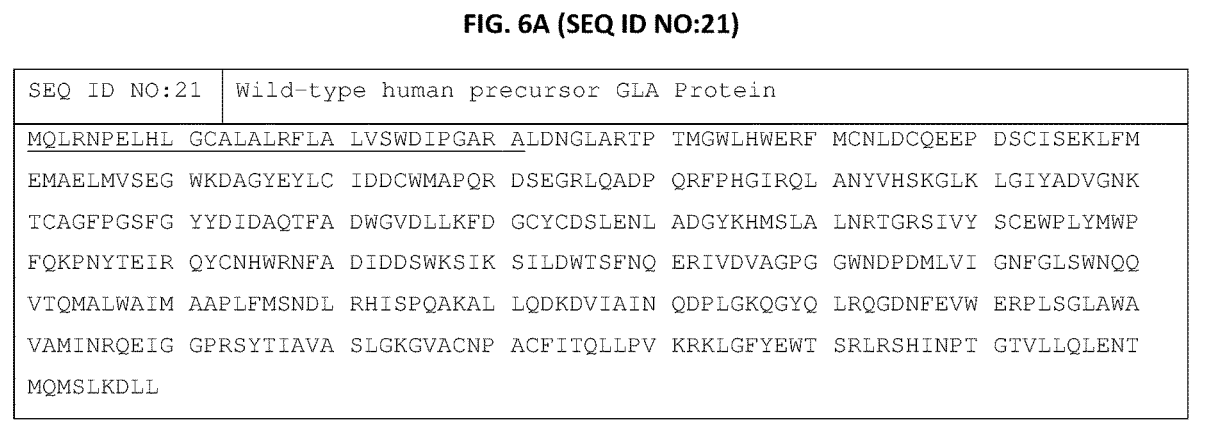

FIG. 6A (SEQ ID NO:21)

| SEQ ID NO:21 | Wild-type human precursor GLA Protein |
| --- | --- |
| MQLRNPELHL GCALALRFLA LVSWDIPGAR ALDNGLARTP TMGWLHWERF MCNLDCQEEP DSCISEKLFM<br>EMAELMVSEG WKDAGYEYLC IDDCWMAPQR DSEGRLQADP QRFPHGIRQL ANYVHSKGLK LGIYADVGNK<br>TCAGFPGSFG YYDIDAQTFA DWGVDLLKFD GCYCDSLENL ADGYKHMSLA LNRTGRSIVY SCEWPLYMWP<br>FQKPNYTEIR QYCNHWRNFA DIDDSWKSIK SILDWTSFNQ ERIVDVAGPG GWNDPDMLVI GNFGLSWNQQ<br>VTQMALWAIM AAPLFMSNDL RHISPQAKAL LQDKDVIAIN QDPLGKQGYQ LRQGDNFEVW ERPLSGLAWA<br>VAMINRQEIG GPRSYTIAVA SLGKGVACNP ACFITQLLPV KRKLGFYEWT SRLRSHINPT GTVLLQLENT<br>MQMSLKDLL | |

FIG. 6B (SEQ ID NO:22)

| SEQ ID NO:22 | Codon-optimized Nucleotide Sequence Encoding GLA Protein of SEQ ID NO:21 |
|---|---|

```
ATGCAGCTGA GAAACCCCGA ACTGCACCTG GGATGTGCCC TGGCTCTGAG ATTTCTGGCC CTGGTGTCTT
GGGACATCCC TGGCGCTAGA GCCCTGGATA ATGGCCTGGC CAGAACACCT ACAATGGGCT GGCTGCACTG
GGAGAGATTC ATGTGCAACC TGGACTGCCA AGAGGAACCC GACAGCTGCA TCAGCGAGAA GCTGTTCATG
GAAATGGCCG AGCTGATGGT GTCCGAAGGC TGGAAGGATG CCGGCTACGA GTACCTGTGC ATCGACGACT
GTTGGATGGC CCCTCAGAGA GACTCTGAGG GCAGACTGCA GGCCGATCCT CAGAGATTTC CCCACGGCAT
TAGACAGCTG GCCAACTACG TGCACAGCAA GGGCCTGAAG CTGGGCATCT ATGCCGACGT GGGCAACAAG
ACCTGTGCCG GCTTTCCTGG CAGCTTCGGC TACTACGATA TCGACGCCCA GACCTTCGCC GATTGGGGAG
TCGATCTGCT GAAGTTCGAC GGCTGCTACT GCGACAGCCT GGAAAATCTG GCCGACGGCT ACAAGCACAT
GTCACTGGCC CTGAATCGGA CCGGCAGATC CATCGTGTAC AGCTGCGAGT GGCCCCTGTA CATGTGGCCC
TTCCAGAAGC CTAACTACAC CGAGATCAGA CAGTACTGCA ACCACTGGCG GAACTTCGCC GACATCGACG
ATAGCTGGAA GTCCATCAAG AGCATCCTGG ACTGGACCAG CTTCAATCAA GAGCGGATCG TGGACGTGGC
AGGACCTGGC GGATGGAACG ATCCTGACAT GCTGGTCATC GGCAACTTCG GCCTGAGCTG GAACCAGCAA
GTGACCCAGA TGGCCCTGTG GGCCATTATG GCCGCTCCTC TGTTCATGAG CAACGACCTG AGACACATCA
GCCCTCAGGC CAAGGCTCTG CTGCAGGACA AGGATGTGAT CGCTATCAAC CAGGATCCTC TGGGCAAGCA
GGGCTACCAG CTGAGACAGG GCGACAATTT CGAAGTGTGG GAAAGACCCC TGAGCGGACT GGCTTGGGCC
GTCGCCATGA TCAACAGACA AGAGATCGGC GGACCCCGGT CCTACACAAT TGCCGTGGCT TCTCTCGGCA
AAGGCGTGGC CTGTAATCCC GCCTGCTTTA TCACACAGCT GCTGCCCGTG AAGAGAAAGC TGGGCTTTTA
CGAGTGGACC AGCAGACTGC GGAGCCACAT CAATCCTACC GGCACAGTGC TGCTGCAGCT GGAAAACACC
ATGCAGATGA GCCTGAAGGA CCTGCTGTAA
```

FIG. 6C (SEQ ID NO:23)

| SEQ ID NO:23 | Codon-optimized Nucleotide Sequence Encoding GLA Protein of SEQ ID NO:21 |
|---|---|
| ATGCAGCTGC GCAACCCCGA GCTGCACCTG GGCTGCGCCC TGGCCCTGCG CTTCCTGGCC CTGGTGAGCT<br>GGGACATCCC CGGCGCCCGC GCCCTGGACA ACGGCCTGGC CCGCACCCCC ACCATGGGCT GGCTGCACTG<br>GGAGCGCTTC ATGTGCAACC TGGACTGCCA GGAGGAGCCC GACAGCTGCA TCAGCGAGAA GCTGTTCATG<br>GAGATGGCCG AGCTGATGGT GAGCGAGGGC TGGAAGGACG CCGGCTACGA GTACCTGTGC ATCGACGACT<br>GCTGGATGGC CCCCCAGCGC GACAGCGAGG GCCGCCTGCA GGCCGACCCC CAGCGCTTCC CCCACGGCAT<br>CCGCCAGCTG GCCAACTACG TGCACAGCAA GGGCCTGAAG CTGGGCATCT ACGCCGACGT GGGCAACAAG<br>ACCTGCGCCG GCTTCCCCGG CAGCTTCGGC TACTACGACA TCGACGCCCA GACCTTCGCC GACTGGGGCG<br>TGGACCTGCT GAAGTTCGAC GGCTGCTACT GCGACAGCCT GGAGAACCTG GCCGACGGCT ACAAGCACAT<br>GAGCCTGGCC CTGAACCGCA CCGGCCGCAG CATCGTGTAC AGCTGCGAGT GGCCCCTGTA CATGTGGCCC<br>TTCCAGAAGC CCAACTACAC CGAGATCCGC CAGTACTGCA ACCACTGGCG CAACTTCGCC GACATCGACG<br>ACAGCTGGAA GAGCATCAAG AGCATCCTGG ACTGGACCAG CTTCAACCAG GAGCGCATCG TGGACGTGGC<br>CGGCCCCGGC GGCTGGAACG ACCCCGACAT GCTGGTGATC GGCAACTTCG GCCTGAGCTG GAACCAGCAG<br>GTGACCCAGA TGGCCCTGTG GGCCATCATG GCCGCCCCCC TGTTCATGAG CAACGACCTG CGCCACATCA<br>GCCCCCAGGC CAAGGCCCTG CTGCAGGACA AGGACGTGAT CGCCATCAAC CAGGACCCCC TGGGCAAGCA<br>GGGCTACCAG CTGCGCCAGG GCGACAACTT CGAGGTGTGG GAGCGCCCCC TGAGCGGCCT GGCCTGGGCC<br>GTGGCCATGA TCAACCGCCA GGAGATCGGC GGCCCCCGCA GCTACACCAT CGCCGTGGCC AGCCTGGGCA<br>AGGGCGTGGC CTGCAACCCC GCCTGCTTCA TCACCCAGCT GCTGCCCGTG AAGCGCAAGC TGGGCTTCTA<br>CGAGTGGACC AGCCGCCTGC GCAGCCACAT CAACCCCACC GGCACCGTGC TGCTGCAGCT GGAGAACACC<br>ATGCAGATGA GCCTGAAGGA CCTGCTGTAA | |

FIG. 6D (SEQ ID NO:24)

| SEQ ID NO:24 | GLA Fusion Protein (HSPG2 signal peptide - mature GLA) |
|---|---|
| MGWRAAGALL LALLLHGRLL ALDNGLARTP TMGWLHWERF MCNLDCQEEP DSCISEKLFM EMAELMVSEG WKDAGYEYLC IDDCWMAPQR DSEGRLQADP QRFPHGIRQL ANYVHSKGLK LGIYADVGNK TCAGFPGSFG YYDIDAQTFA DWGVDLLKFD GCYCDSLENL ADGYKHMSLA LNRTGRSIVY SCEWPLYMWP FQKPNYTEIR QYCNHWRNFA DIDDSWKSIK SILDWTSFNQ ERIVDVAGPG GWNDPDMLVI GNFGLSWNQQ VTQMALWAIM AAPLFMSNDL RHISPQAKAL LQDKDVIAIN QDPLGKQGYQ LRQGDNFEVW ERPLSGLAWA VAMINRQEIG GPRSYTIAVA SLGKGVACNP ACFITQLLPV KRKLGFYEWT SRLRSHINPT GTVLLQLENT MQMSLKDLL | |

FIG. 6E (SEQ ID NO:25)

| SEQ ID NO:25 | Codon-optimized Nucleotide Sequence Encoding the GLA Fusion Protein of SEQ ID NO:24 |
|---|---|

ATGGGCTGGC GAGCTGCTGG TGCACTTCTG CTGGCTCTGC TGCTTCATGG CAGACTGCTT GCTCTGGACA
ACGGCCTGGC CCGCACCCCC ACCATGGGCT GGCTGCACTG GGAGCGCTTC ATGTGCAACC TGGACTGCCA
GGAGGAGCCC GACAGCTGCA TCAGCGAGAA GCTGTTCATG GAGATGGCCG AGCTGATGGT GAGCGAGGGC
TGGAAGGACG CCGGCTACGA GTACCTGTGC ATCGACGACT GCTGGATGGC CCCCCAGCGC GACAGCGAGG
GCCGCCTGCA GGCCGACCCC CAGCGCTTCC CCCACGGCAT CCGCCAGCTG GCCAACTACG TGCACAGCAA
GGGCCTGAAG CTGGGCATCT ACGCCGACGT GGGCAACAAG ACCTGCGCCG GCTTCCCCGG CAGCTTCGGC
TACTACGACA TCGACGCCCA GACCTTCGCC GACTGGGGCG TGGACCTGCT GAAGTTCGAC GGCTGCTACT
GCGACAGCCT GGAGAACCTG GCCGACGGCT ACAAGCACAT GAGCCTGGCC CTGAACCGCA CCGGCCGCAG
CATCGTGTAC AGCTGCGAGT GGCCCCTGTA CATGTGGCCC TTCCAGAAGC CCAACTACAC CGAGATCCGC
CAGTACTGCA ACCACTGGCG CAACTTCGCC GACATCGACG ACAGCTGGAA GAGCATCAAG AGCATCCTGG
ACTGGACCAG CTTCAACCAG GAGCGCATCG TGGACGTGGC CGGCCCCGGC GGCTGGAACG ACCCCGACAT
GCTGGTGATC GGCAACTTCG GCCTGAGCTG GAACCAGCAG GTGACCCAGA TGGCCCTGTG GGCCATCATG
GCCGCCCCCC TGTTCATGAG CAACGACCTG CGCCACATCA GCCCCCAGGC CAAGGCCCTG CTGCAGGACA
AGGACGTGAT CGCCATCAAC CAGGACCCCC TGGGCAAGCA GGGCTACCAG CTGCGCCAGG GCGACAACTT
CGAGGTGTGG GAGCGCCCCC TGAGCGGCCT GGCCTGGGCC GTGGCCATGA TCAACCGCCA GGAGATCGGC
GGCCCCCGCA GCTACACCAT CGCCGTGGCC AGCCTGGGCA AGGGCGTGGC CTGCAACCCC GCCTGCTTCA
TCACCCAGCT GCTGCCCGTG AAGCGCAAGC TGGGCTTCTA CGAGTGGACC AGCCGCCTGC GCAGCCACAT
CAACCCCACC GGCACCGTGC TGCTGCAGCT GGAGAACACC ATGCAGATGA GCCTGAAGGA CCTGCTGTAA

SEQUENCE LISTING

```
<160> NUMBER OF SEQ ID NOS: 51

<210> SEQ ID NO 1
<211> LENGTH: 1400
<212> TYPE: DNA
<213> ORGANISM: Homo sapiens

<400> SEQUENCE: 1

tccagcacaa aagacatttg gaggagaaca atttaattat aaaagcattt tttttacatc      60

tactatttca tttattgtca gattagggga tagaccttaa ttatagtttt taataagtat     120

tcttaacctg ttgcatatct atggtgtttt tcaaagttac tacaatacag taaataattc     180

tcaacagatt aagaaggtaa taacatattc cttttaaaga aagatattga gaaatatgta     240

agaaatgata gtctcctatt ctcatgtctg tgttcactac ccacgtgttt tctgggaaga     300

aatatgaaat aaaatgattt tcaaaagaga gtccttctca aacaaatact gacggttaac     360

tgcttttaca tataatggca agttgagtca gccaccattt ttaataaaac tgattaatga     420

ctaagtgtgg acaaaaacagg gaagtgagta atcaggtgga atttatgcta tcctaaagcc     480

ggaataaaag tctatgagat ggaaaaaaag tctttagggg cttggccaag ttcttaaata     540

attgggaggc tgagcagagg ggccgctctc aggaatcagc atccagttgc acagacagag     600

cctattaaaa attaagaaaa tagtttgaga tgactatttt aagcgttatg aattgccaaa     660

tggcaaatgc ctagctgaac agatgactgg tttggattct taatagccaa ttgtaaagga     720

aatggaccac aacaggcttt cagacacaga agtggccgtc cgtgctgaga ccgaggtgtg     780

gggtacatct aaatgtaagg atcagcagtt ccccagagag caaacgtgaa aagctcaagt     840

ctaatttccc atcattgttg agcattttcc agaaaattaa gggccaatct ggagctggag     900

ataggagtgt agggagcatc tgcattggac tgagtcttag agttggggaa gcccagggac     960

ggggtgagac tattttaggc gttatttaac agtctaataa ttcgaggggt ttttaagacc    1020

attgtattaa tcatgctttt tcttgtccat atttcctggt gctttgacat cttggggccc    1080

tgcttgactc tgaagagact gccccttcca gggctggcca aatcctagag atagtaagtg    1140

acttgccttt actacgccag taagctataa tcacccaagg ccaagtacca gacaacccag    1200

gaaggcatct acaccccaga gcctgctgaa attattcaga ccagccaatc ctaagcctgc    1260

ctacactgcc ttgtcctttc cttcctgcag aaaccacaat aaaggctgtc acccatgttt    1320

ccccctcaat ctctctacct cctgacagcc cctggtactt cccatgtggc cctgcatggc    1380

atggcctgtc ctcacttctc                                                1400
```

-continued

<210> SEQ ID NO 2
<211> LENGTH: 1306
<212> TYPE: DNA
<213> ORGANISM: Homo sapiens

<400> SEQUENCE: 2
actgtgttgg acgctcccat gtattgtctt ttttttaaat gtatttttat ttgtttttta 60
aaatagagac agaacctcac catgttgccc gggctggtct caaactccct gggctcaggc 120
aatcctcctg ccttggcctc ccaaagtgct gggattatag gtgtgagcca cagtgctgtg 180
ccctgggtat tgtttagtcc tcccaacaac tctatgaggc agatataatt gacctatttt 240
gcaggtaaaa aagactctgt aacttgccca gagtcacaca aactgggatt tgagcccaac 300
ttgtctttct cctgtgtcct ggtacataag taagatccat gggattttca ctgtaaacat 360
caccctaaat attttttaaa gtagaaatac ccatattaga aatgactcaa gggcacaatt 420
acttagctag aatataaaat tcctggaaac atttactggc ttctccagat aaagtttatc 480
ttactaaata attaggactt ttattttttc ctccttccct ccctctctcc attccatcat 540
tcttttctca ttctttcttt caagattaga gtaatatcta aatcacagtc acgtagagca 600
gtacaaccca tgttgaggta acttattaaa ttagcccctg accatacatt actattcaga 660
gggctgggaa agatctgtaa gggattggac aaaggaaatg ctccacctgt tcctcctctg 720
acttgggccc ttgatgatat catataaaaa gtcatttcct gcttggtcct tatctctaat 780
gctgactaaa ttaatagtct tacttccttt acttgtgtgt atggaatttg ggaataaaag 840
taaaatcact tcctactggg ttttatactt aggctcctta aatttcatgt acttgggcaa 900
tttttcctta tttggggact acaggttgtt cgatgtaaaa aaggaacaaa ttataacaca 960
tgccatgccg aaattcagtg agagtcatgg tttacctggt acccatgttc taatgaatgt 1020
atttccaacc tgtaaacttg ctgaagattt ggaataagta aaaccaaaat catactagta 1080
tggaggtttt aaaactaact taaaagagtg actgtatatt cacaattgct accaaaaaaa 1140
aaaataccta ggaatacagc taactaggga ggtgaaagag ctctacaagg agaactgtta 1200
aacactgaaa agaaatcaga gatgatgcaa acaaatggaa aaacattcca tgctcatgga 1260
taggaggaat caacatcatt aaaatggcca tagtgcccaa agcaat 1306

<210> SEQ ID NO 3
<211> LENGTH: 1219
<212> TYPE: DNA
<213> ORGANISM: Homo sapiens

<400> SEQUENCE: 3
agctggcaac ctccccaccc ctagcacagg cccatgccca ggcctagcac agctggtcca 60
tataactctc gccttcctgc tggtgctcag attgaagggg aaagagggaa acaagggcag 120
gagagataag gagccttcct tacacattcc tccatgagcc caggagggga ccttagccac 180
accgtgtgac agcagcattc ctgggaggtc cgttgcaagg aaccagcact cactgcatgc 240
ctgctgacac ctggggttaa gagggaaact gtcctctccc aggagaacaa acatgcattg 300
cgtgcctcct gcacgctcag agctgtgccg ggacctcctg tgatgtcacc tggtttatcc 360
tcaacaatct gtgcgtcaga ccaagagatg cccattttta caagattcag agacatcagc 420
gaatgtttgg ccacaccagg atgtgaacag cagacattct gactccaaag cccacgttct 480
ttgtattttc ccccttcaga gaagtccccg ttccctccct taagtgatgt cattgccacc 540
ttgttctgga gagagagagc tgcttacagc ctcatatcat catgacctga cttaacgctg 600
ctgagcacag tcagttcacc ctgaccctgt tttccggatc agcctcgcgc tgagtcagag 660
ccgtgcatta ggaggagggg ctcctttcag gcctgtagcg ggtgggaggg agctggctag 720
ccctgttata ttttaaccca ttcctccgag cttctccttt ttgactgtgt tcgaatagac 780
cccatgagtt aagtgatgat cattttctgc agaatgagca gcagcctagc attcgtgacc 840
ctcttacagt gtcatgcgtg tctgccttcc tgcccctctg tccctaggcc tctgtgcctc 900
ttaacctcag ttgggaatct ttggattgca aacgatagaa aacccaactc aaggccgggc 960
gcggtggctt gtgcctgtca tcccagcact tcgggaggcc gaggtgggag gatcacttga 1020
gcccaggaat tcaagaccag cctggacaac attgtgagac cacatctcta caaaacttta 1080
acaaaattgg tgtgctggtg tgtacccata atcccagcta ctttggcgac tgaggtggga 1140
ggactacttg agcctagagg ttcaagactg cagtgacgct gggcacagtg gctcatgcct 1200
gtaatcccag cactttggg 1219

<210> SEQ ID NO 4
<211> LENGTH: 1733
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
ctcgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtcgagg tgagccccac gttctgcttc actctcccca 420
tctccccccc ctccccaccc ccaattttgt atttatttat tttttaatta ttttgtgcag 480
cgatgggggc gggggggggg gggggcgcg cgccaggcgg ggcggggcgg ggcgaggggc 540
ggggcggggc gaggcggaga ggtgcggcgg cagccaatca gagcggcgcg ctccgaaagt 600
ttccttttat ggcgaggcgg cggcggcggc ggccctataa aaagcgaagc gcgcggcggg 660
cgggagtcgc tgcgcgctgc cttcgccccg tgccccgctc cgccgccgcc tcgcgccgcc 720
cgccccggct ctgactgacc gcgttactcc cacaggtgag cgggcgggac ggcccttctc 780
ctccgggctg taattagcgc ttggtttaat gacggcttgt ttcttttctg tggctgcgtg 840
aaagccttga ggggctccgg gagggccctt tgtgcggggg gagcggctcg gggggtgcgt 900
gcgtgtgtgt gtgcgtgggg agcgccgcgt gcggctccgc gctgcccggc ggctgtgagc 960
gctgcgggcg cggcgcgggg ctttgtgcgc tccgcagtgt gcgcgagggg agcgcggccg 1020
ggggcggtgc cccgcggtgc gggggggct gcgaggggaa caaaggctgc gtgcggggtg 1080
tgtgcgtggg ggggtgagca gggggtgtgg gcgcgtcggt cgggctgcaa cccccccctgc 1140 acccccctcc ccgagttgct gagcacggcc cggcttcggg tgcggggctc cgtacggggc 1200
gtggcgcggg gctcgccgtg ccgggcgggg ggtggcggca ggtgggggtg ccgggcgggg 1260
cggggccgcc tcgggccggg gagggctcgg gggaggggcg cggcggcccc cggagcgccg 1320
gcggctgtcg aggcgcggcg agccgcagcc attgcctttt atggtaatcg tgcgagaggg 1380

```
cgcagggact tcctttgtcc caaatctgtg cggagccgaa atctgggagg cgccgccgca   1440

cccccctctag cgggcgcggg gcgaagcggt gcggcgccgg caggaaggaa atgggcgggg   1500

agggccttcg tgcgtcgccg cgccgccgtc cccttctccc tctccagcct cggggctgtc   1560

cgcgggggga cggctgcctt cgggggggac ggggcagggc ggggttcggc ttctggcgtg   1620

tgaccggcgg ctctagagcc tctgctaacc atgttcatgc cttcttcttt ttcctacagc   1680

tcctgggcaa cgtgctggtt attgtgctgt ctcatcattt tggcaaagaa ttg          1733
```

<210> SEQ ID NO 5
<211> LENGTH: 798
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
cgttacataa cttacggtaa atggcccgcc tggctgaccg cccaacgacc cccgcccatt     60

gacgtcaata gtaacgccaa tagggacttt ccattgacgt caatgggtgg agtatttacg    120

gtaaactgcc cacttggcag tacatcaagt gtatcatatg ccaagtacgc cccctattga    180

cgtcaatgac ggtaaatggc ccgcctggca ttgtgcccag tacatgacct tatgggactt    240

tcctacttgg cagtacatct acgtattagt catcgctatt accatggtcg aggtgagccc    300

cacgttctgc ttcactctcc ccatctcccc cccctcccca cccccaattt tgtatttatt    360

tatttttttaa ttattttgtg cagcgatggg ggcggggggg ggggggggggc gcgcgccagg    420

cggggcgggg cggggcgagg ggcggggcgg ggcgaggcgg agaggtgcgg cggcagccaa    480

tcagagcggc gcgctccgaa agtttccttt tatggcgagg cggcggcggc ggcggcccta    540

taaaaagcga agcgcgcggc gggcgggagt cgctgcgcgc tgccttcgcc ccgtgccccg    600

ctccgccgcc gcctcgcgcc gcccgccccg gctctgactg accgcgttac tcccacaggt    660

gagcgggcgg gacggccctt ctcctccggg ctgtaattag ctgagcaaga ggtaagggtt    720

taagggatgg ttggttggtg gggtattaat gtttaattac ctggagcacc tgcctgaaat    780

cactttttttt caggttgg                                                  798
```

<210> SEQ ID NO 6
<211> LENGTH: 522
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
tcctcaggtg caggctgcct atcagaaggt ggtggctggt gtggccaatg ccctggctca     60

caaataccac tgagatcttt ttccctctgc caaaaattat ggggacatca tgaagcccct    120

tgagcatctg acttctggct aataaaggaa atttattttc attgcaatag tgtgttggaa    180

ttttttgtgt ctctcactcg gaaggacata tgggagggca aatcatttaa aacatcagaa    240

tgagtatttg gtttagagtt tggcaacata tgcccatatg ctggctgcca tgaacaaagg    300

ttggctataa agaggtcatc agtatatgaa acagccccct gctgtccatt ccttattcca    360

tagaaaagcc ttgacttgag gttagatttt ttttatattt tgttttgtgt tatttttttc    420

tttaacatcc ctaaaatttt ccttacatgt tttactagcc agatttttcc tcctctcctg    480
```

-continued actactccca gtcatagctg tccctcttct cttatggaga tc 522

<210> SEQ ID NO 7
<211> LENGTH: 2348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7
ctcgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtcgagg tgagccccac gttctgcttc actctcccca 420
tctccccccc ctccccaccc ccaattttgt atttatttat tttttaatta ttttgtgcag 480
cgatgggggc gggggggggg ggggggcgcg cgccaggcgg ggcggggcgg ggcgaggggc 540
ggggcggggc gaggcggaga ggtgcggcgg cagccaatca gagcggcgcg ctccgaaagt 600
ttccttttat ggcgaggcgg cggcggcggc ggccctataa aaagcgaagc gcgcggcggg 660
cgggagtcgc tgcgcgctgc cttcgccccg tgccccgctc cgccgccgcc tcgcgccgcc 720
cgccccggct ctgactgacc gcgttactcc cacaggtgag cgggcgggac ggcccttctc 780
ctccgggctg taattagcgc ttggtttaat gacggcttgt ttcttttctg tggctgcgtg 840
aaagccttga ggggctccgg gagggccctt tgtgcggggg gagcggctcg gggggtgcgt 900
gcgtgtgtgt gtgcgtgggg agcgccgcgt gcggctccgc gctgcccggc ggctgtgagc 960
gctgcgggcg cggcgcgggg ctttgtgcgc tccgcagtgt gcgcgagggg agcgcggccg 1020
ggggcggtgc cccgcggtgc ggggggggct gcgaggggaa caaaggctgc gtgcggggtg 1080
tgtgcgtggg ggggtgagca gggggtgtgg gcgcgtcggt cgggctgcaa ccccccctgc 1140
acccccctcc ccgagttgct gagcacggcc cggcttcggg tgcggggctc cgtacggggc 1200
gtggcgcggg gctcgccgtg ccgggcgggg ggtggcggca ggtgggggtg ccgggcgggg 1260
cggggccgcc tcgggccggg gagggctcgg gggaggggcg cggcggcccc cggagcgccg 1320
gcggctgtcg aggcgcggcg agccgcagcc attgcctttt atggtaatcg tgcgagaggg 1380
cgcagggact tcctttgtcc caaatctgtg cggagccgaa atctgggagg cgccgccgca 1440
ccccctctag cgggcgcggg gcgaagcggt gcggcgccgg caggaaggaa atgggcgggg 1500
agggccttcg tgcgtcgccg cgccgccgtc cccttctccc tctccagcct cggggctgtc 1560
cgcgggggga cggctgcctt cgggggggac ggggcagggc ggggttcggc ttctggcgtg 1620
tgaccggcgg ctctagagcc tctgctaacc atgttcatgc cttcttcttt ttcctacagc 1680
tcctgggcaa cgtgctggtt attgtgctgt ctcatcattt tggcaaagaa ttgcaagttt 1740
gtacaaaaaa gcaggctgcc accgaattcg cggccgctaa acccagcttt cttgtacaaa 1800
gtggcaactt tattatacat agttgatcct caggtgcagg ctgcctatca gaaggtggtg 1860
gctggtgtgg ccaatgccct ggctcacaaa taccactgag atctttttcc ctctgccaaa 1920
aattatgggg acatcatgaa gccccttgag catctgactt ctggctaata aaggaaattt 1980

```
attttcattg caatagtgtg ttggaatttt ttgtgtctct cactcggaag gacatatggg   2040

agggcaaatc atttaaaaca tcagaatgag tatttggttt agagtttggc aacatatgcc   2100

catatgctgg ctgccatgaa caaaggttgg ctataaagag gtcatcagta tatgaaacag   2160

ccccctgctg tccattcctt attccataga aaagccttga cttgaggtta gattttttt    2220

atattttgtt ttgtgttatt tttttcttta acatccctaa aattttcctt acatgtttta   2280

ctagccagat ttttcctcct ctcctgacta ctcccagtca tagctgtccc tcttctctta   2340

tggagatc                                                            2348


<210> SEQ ID NO 8
<211> LENGTH: 1457
<212> TYPE: PRT
<213> ORGANISM: Homo sapiens

<400> SEQUENCE: 8

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300
```

-continued

```
Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
```

-continued

```
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Arg His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140
```

Asn Lys Cys Gln Thr Pro Leu Gly Met Ala Ser Gly His Ile Arg
1145 1150 1155

Asp Phe Gln Ile Thr Ala Ser Gly Gln Tyr Gly Gln Trp Ala Pro
1160 1165 1170

Lys Leu Ala Arg Leu His Tyr Ser Gly Ser Ile Asn Ala Trp Ser
1175 1180 1185

Thr Lys Glu Pro Phe Ser Trp Ile Lys Val Asp Leu Leu Ala Pro
1190 1195 1200

Met Ile Ile His Gly Ile Lys Thr Gln Gly Ala Arg Gln Lys Phe
1205 1210 1215

Ser Ser Leu Tyr Ile Ser Gln Phe Ile Ile Met Tyr Ser Leu Asp
1220 1225 1230

Gly Lys Lys Trp Gln Thr Tyr Arg Gly Asn Ser Thr Gly Thr Leu
1235 1240 1245

Met Val Phe Phe Gly Asn Val Asp Ser Ser Gly Ile Lys His Asn
1250 1255 1260

Ile Phe Asn Pro Pro Ile Ile Ala Arg Tyr Ile Arg Leu His Pro
1265 1270 1275

Thr His Tyr Ser Ile Arg Ser Thr Leu Arg Met Glu Leu Met Gly
1280 1285 1290

Cys Asp Leu Asn Ser Cys Ser Met Pro Leu Gly Met Glu Ser Lys
1295 1300 1305

Ala Ile Ser Asp Ala Gln Ile Thr Ala Ser Ser Tyr Phe Thr Asn
1310 1315 1320

Met Phe Ala Thr Trp Ser Pro Ser Lys Ala Arg Leu His Leu Gln
1325 1330 1335

Gly Arg Ser Asn Ala Trp Arg Pro Gln Val Asn Asn Pro Lys Glu
1340 1345 1350

Trp Leu Gln Val Asp Phe Gln Lys Thr Met Lys Val Thr Gly Val
1355 1360 1365

Thr Thr Gln Gly Val Lys Ser Leu Leu Thr Ser Met Tyr Val Lys
1370 1375 1380

Glu Phe Leu Ile Ser Ser Ser Gln Asp Gly His Gln Trp Thr Leu
1385 1390 1395

Phe Phe Gln Asn Gly Lys Val Lys Val Phe Gln Gly Asn Gln Asp
1400 1405 1410

Ser Phe Thr Pro Val Val Asn Ser Leu Asp Pro Pro Leu Leu Thr
1415 1420 1425

Arg Tyr Leu Arg Ile His Pro Gln Ser Trp Val His Gln Ile Ala
1430 1435 1440

Leu Arg Met Glu Val Leu Gly Cys Glu Ala Gln Asp Leu Tyr
1445 1450 1455

<210> SEQ ID NO 9
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
atgcagattg agctgagcac ctgtttcttc ctgtgcctgc tgagattttg cttctcagct 60
acccgcaggt actacctggg agccgttgag ctgtcctggg attacatgca gtcagatctg 120

-continued

```
ggggagctgc ctgtggacgc tcggtttccc cccagagtgc caaagtcctt tcccttcaac    180
accagcgtgg tgtacaaaaa gacacttttt gttgaattta ctgaccactt gttcaacatc    240
gccaagccac gacccccatg gatgggcctg ctggggccaa ccattcaggc agaggtttac    300
gacacagtcg tgatcacact gaagaacatg gcctcccatc cagtgtctct gcacgccgtc    360
ggtgtgtcct actggaaagc atccgagggc gccgagtatg acgaccagac cagccagaga    420
gagaaagagg acgacaaagt gttccctgga ggcagccaca cctacgtgtg gcaggtgttg    480
aaggaaaatg ggcccatggc cagtgaccct ttgtgtctga cttactcata cctgtctcat    540
gtggatctag tcaaggacct gaattctgga ctgattgggg cactgcttgt gtgccgcgaa    600
ggcagcctgg ccaaagaaaa gacacagacc cttcacaagt tcatcctgct gttcgccgtg    660
ttcgacgaag gcaaatcctg gcactcagaa accaaaaact cactgatgca ggaccgggat    720
gccgcctctg cccgcgcatg gccaaaaatg cacaccgtca acggctatgt caatagaagt    780
ttgcccggcc tcattggatg tcacaggaaa agcgtctatt ggcatgtaat cgggatggga    840
accacacctg aggtccacag catatttctg gaaggccaca catttctggt gagaaatcat    900
cgccaggctt ccctggaaat ttcccccatc accttcttga ccgcccagac actgctcatg    960
gatcttgggc agtttctgct gttttgtcat atttcttctc accaacacga cggaatggag   1020
gcctacgtta aggtcgatag ttgccctgaa gaacctcagc tgaggatgaa gaacaacgag   1080
gaagccgagg actacgatga cgatttgacc gattccgaaa tggacgtggt gcgctttgat   1140
gatgacaatt ctccatcctt cattcagatt agatccgtcg ccaagaagca ccccaagacc   1200
tgggtgcact acattgcagc cgaggaggag gattgggact acgcccccct ggtgctggca   1260
cccgacgacc gaagctacaa atctcagtac ctgaacaatg gtccacaacg gatcggcagg   1320
aagtacaaga aagtgcggtt catggcctat acagacgaaa ccttcaaaac cagggaggct   1380
atccagcacg agtctgggat tctgggacca ctcctgtacg gcgaagtggg cgacaccttg   1440
ttaattatct tcaagaacca ggctagtaga ccttataaca tttatcccca cggcattacc   1500
gatgtgcggc ctctctactc taggcggctt ccaaaggggg tgaaacacct gaaggacttt   1560
cccatcctcc ctggcgaaat ctttaagtat aagtggacag tgaccgtgga ggatggacca   1620
accaagagcg accccaggtg cctgacacgc tattattcaa gcttcgtgaa tatggaaagg   1680
gacctcgcat ctggcttgat cggccctctg ctgatatgtt acaaggaaag cgtcgatcag   1740
agaggaaatc agatcatgtc agacaaaagg aatgtgatcc tgttctccgt cttcgatgaa   1800
aacaggagct ggtatctgac agagaacatc cagagattcc tgccaaatcc cgccggcgtc   1860
cagctggagg acccggagtt tcaggcatct aacatcatgc attccattaa tggttacgtg   1920
ttcgactccc tgcagctgag cgtgtgcctc cacgaggtgg cctactggta catcttgagc   1980
atcggcgccc agaccgactt tctgagcgtc tttttctccg ggtatacttt caaacataag   2040
atggtgtacg aagatactct gacgctgttc cctttctctg ggagactgt gtttatgtct   2100
atggagaacc ctggactgtg gattctcgga tgccacaaca gtgactttcg taatagaggg   2160
atgactgcac tgctgaaggt gtccagctgt gataaaaata ctggcgacta ctacgaagat   2220
agctatgagg atatctcagc atacctgctg agcaagaata acgccatcga gccccgaagc   2280
ttctcacaga atccccctgt cctcaagagg caccagcgag agatcacaag gaccacactc   2340
cagtccgacc aggaggagat tgactacgat gacacgattt ctgtggagat gaaaaaagag   2400
gactttgaca tctacgatga ggatgaaaac cagagcccta ggtcgttcca gaagaaaaca   2460
aggcactact tcattgccgc cgtggagaga ctgtgggact acggaatgag tagttcccca   2520
```

```
cacgtgttgc ggaacagagc ccagagtggg tccgtcccac agttcaagaa ggttgttttc   2580

caggagttca cagatggctc cttcactcag ccactgtatc gcggcgagct gaatgagcac   2640

ttgggcttat tgggccccta cattcgcgca gaagtcgaag ataatattat ggtgaccttc   2700

cgcaaccagg ccagccggcc ttactcattc tactcctctc tcatctctta tgaggaggat   2760

cagcgccagg gcgccgaacc ccggaagaac tttgtgaagc ccaatgaaac caaaacttac   2820

ttttggaagg tgcagcacca tatggcgccg acgaaagacg aatttgactg caaagcctgg   2880

gcctacttca gcgacgtcga cttggagaag gacgtccaca gcggcctgat tggccctttg   2940

ttggtctgcc ataccaatac actcaaccct gcccacggga ggcaggtgac cgtgcaggag   3000

tttgccttgt tcttcaccat cttcgacgaa accaagagct ggtacttcac agagaacatg   3060

gagaggaact gcagagcacc ctgtaacatc cagatggagg accctacttt caaggaaaat   3120

tacaggttcc atgccattaa tggctacatc atggataccc tccccgggct tgtgatggct   3180

caggaccagc gcatccgctg gtacctgctc tcaatgggct ccaacgagaa cattcatagc   3240

atccacttta gtggccacgt gtttaccgtg cgcaagaagg aggagtacaa gatggcactg   3300

tacaacctgt accctggcgt gtttgagaca gtggagatgc tgccatccaa ggccggcatc   3360

tggcgcgtgg agtgcctcat tggggagcac ctccatgctg gcatgtctac actgttcctg   3420

gtgtacagca acaagtgtca gactccactc ggaatggcct ccgggcatat ccgcgatttt   3480

cagatcacgg cctctggcca gtatggccaa tgggctccca agctggccag gctgcactac   3540

agtgggagta tcaacgcttg gagcaccaag gagcctttct cctggatcaa ggtggacctg   3600

cttgccccca tgattattca cggcattaag acacaggggg ccaggcagaa attctcctcc   3660

ctgtacatct cccagttcat catcatgtac agtctggacg gcaaaaagtg gcagacctac   3720

cgcgggaaca gtaccgggac attgatggtg ttcttcggga acgtggactc tagcggcatt   3780

aaacacaaca ttttcaaccc ccccatcatt gctaggtata tcaggctcca tcccacccac   3840

tatagcatca ggtccactct gcggatggag ctgatgggct gcgaccttaa ttcatgcagc   3900

atgccgctgg gcatggagtc aaaggccatc tccgacgccc aaatcaccgc ctccagctac   3960

ttcaccaata tgttcgccac ctggagcccc agcaaggccc ggctgcacct gcagggccgc   4020

agcaacgcct ggcggcctca ggtgaacaac cccaaggagt ggctgcaggt ggacttccag   4080

aaaaccatga aggtgactgg ggtcaccacc cagggagtca agagcctgct gaccagcatg   4140

tatgtgaagg agttcttgat cagctcgtca caggatggcc accagtggac tttgttcttt   4200

cagaacggta aggtgaaagt gttccaggga aaccaagatt cctttacacc agtggtcaac   4260

tctctggatc ctcccctgct gacacggtac ctgcggatcc atccccagtc atgggtgcac   4320

cagattgctc tgcgcatgga ggtgcttggc tgcgaggccc aggacctgta ctga         4374
```

```
<210> SEQ ID NO 10
<211> LENGTH: 1457
<212> TYPE: PRT
<213> ORGANISM: Homo sapiens

<400> SEQUENCE: 10

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45
```

-continued

```
Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460
```

-continued

```
Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Ala His Gln Ala Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
```

-continued

```
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185

Thr Lys  Glu Pro Phe Ser Trp  Ile Lys Val Asp Leu  Leu Ala Pro
    1190                1195                1200

Met Ile  Ile His Gly Ile Lys  Thr Gln Gly Ala Arg  Gln Lys Phe
    1205                1210                1215

Ser Ser  Leu Tyr Ile Ser Gln  Phe Ile Ile Met Tyr  Ser Leu Asp
    1220                1225                1230

Gly Lys  Lys Trp Gln Thr Tyr  Arg Gly Asn Ser Thr  Gly Thr Leu
    1235                1240                1245

Met Val  Phe Phe Gly Asn Val  Asp Ser Ser Gly Ile  Lys His Asn
    1250                1255                1260

Ile Phe  Asn Pro Pro Ile Ile  Ala Arg Tyr Ile Arg  Leu His Pro
    1265                1270                1275

Thr His  Tyr Ser Ile Arg Ser  Thr Leu Arg Met Glu  Leu Met Gly
    1280                1285                1290
```

Cys Asp Leu Asn Ser Cys Ser Met Pro Leu Gly Met Glu Ser Lys
1295 1300 1305

Ala Ile Ser Asp Ala Gln Ile Thr Ala Ser Ser Tyr Phe Thr Asn
1310 1315 1320

Met Phe Ala Thr Trp Ser Pro Ser Lys Ala Arg Leu His Leu Gln
1325 1330 1335

Gly Arg Ser Asn Ala Trp Arg Pro Gln Val Asn Asn Pro Lys Glu
1340 1345 1350

Trp Leu Gln Val Asp Phe Gln Lys Thr Met Lys Val Thr Gly Val
1355 1360 1365

Thr Thr Gln Gly Val Lys Ser Leu Leu Thr Ser Met Tyr Val Lys
1370 1375 1380

Glu Phe Leu Ile Ser Ser Ser Gln Asp Gly His Gln Trp Thr Leu
1385 1390 1395

Phe Phe Gln Asn Gly Lys Val Lys Val Phe Gln Gly Asn Gln Asp
1400 1405 1410

Ser Phe Thr Pro Val Val Asn Ser Leu Asp Pro Pro Leu Leu Thr
1415 1420 1425

Arg Tyr Leu Arg Ile His Pro Gln Ser Trp Val His Gln Ile Ala
1430 1435 1440

Leu Arg Met Glu Val Leu Gly Cys Glu Ala Gln Asp Leu Tyr
1445 1450 1455

<210> SEQ ID NO 11
<211> LENGTH: 4374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
atgcagattg agctgagcac ctgtttcttc ctgtgcctgc tgagattttg cttctcagct 60
acccgcaggt actacctggg agccgttgag ctgtcctggg attacatgca gtcagatctg 120
ggggagctgc ctgtggacgc tcggtttccc cccagagtgc caaagtcctt tcccttcaac 180
accagcgtgg tgtacaaaaa gacacttttt gttgaattta ctgaccactt gttcaacatc 240
gccaagccac gacccccatg gatgggcctg ctggggccaa ccattcaggc agaggtttac 300
gacacagtcg tgatcacact gaagaacatg gcctcccatc cagtgtctct gcacgccgtc 360
ggtgtgtcct actggaaagc atccgagggc gccgagtatg acgaccagac cagccagaga 420
gagaaagagg acgacaaagt gttccctgga ggcagccaca cctacgtgtg gcaggtgttg 480
aaggaaaatg ggcccatggc cagtgaccct ttgtgtctga cttactcata cctgtctcat 540
gtggatctag tcaaggacct gaattctgga ctgattgggg cactgcttgt gtgccgcgaa 600
ggcagcctgg ccaaagaaaa gacacagacc cttcacaagt tcatcctgct gttcgccgtg 660
ttcgacgaag gcaaatcctg gcactcagaa accaaaaact cactgatgca ggaccgggat 720
gccgcctctg cccgcgcatg gccaaaaatg cacaccgtca acggctatgt caatagaagt 780
ttgcccggcc tcattggatg tcacaggaaa agcgtctatt ggcatgtaat cgggatggga 840
accacacctg aggtccacag catatttctg gaaggccaca catttctggt gagaaatcat 900
cgccaggctt ccctggaaat ttcccccatc accttcttga ccgcccagac actgctcatg 960
gatcttgggc agtttctgct gttttgtcat atttcttctc accaacacga cggaatggag 1020

-continued

```
gcctacgtta aggtcgatag ttgccctgaa gaacctcagc tgaggatgaa gaacaacgag   1080
gaagccgagg actacgatga cgatttgacc gattccgaaa tggacgtggt gcgctttgat   1140
gatgacaatt ctccatcctt cattcagatt agatccgtcg ccaagaagca ccccaagacc   1200
tgggtgcact acattgcagc cgaggaggag gattgggact acgcccccct ggtgctggca   1260
cccgacgacc gaagctacaa atctcagtac ctgaacaatg gtccacaacg gatcggcagg   1320
aagtacaaga aagtgcggtt catggcctat acagacgaaa ccttcaaaac cagggaggct   1380
atccagcacg agtctgggat tctgggacca ctcctgtacg gcgaagtggg cgacaccttg   1440
ttaattatct tcaagaacca ggctagtaga ccttataaca tttatcccca cggcattacc   1500
gatgtgcggc ctctctactc taggcggctt ccaaaggggg tgaaacacct gaaggacttt   1560
cccatcctcc ctggcgaaat ctttaagtat aagtggacag tgaccgtgga ggatggacca   1620
accaagagcg accccaggtg cctgacacgc tattattcaa gcttcgtgaa tatggaaagg   1680
gacctcgcat ctggcttgat cggccctctg ctgatatgtt acaaggaaag cgtcgatcag   1740
agaggaaatc agatcatgtc agacaaaagg aatgtgatcc tgttctccgt cttcgatgaa   1800
aacaggagct ggtatctgac agagaacatc cagagattcc tgccaaatcc cgccggcgtc   1860
cagctggagg acccggagtt tcaggcatct aacatcatgc attccattaa tggttacgtg   1920
ttcgactccc tgcagctgag cgtgtgcctc cacgaggtgg cctactggta catcttgagc   1980
atcggcgccc agaccgactt tctgagcgtc tttttctccg ggtatacttt caaacataag   2040
atggtgtacg aagatactct gacgctgttc cctttctctg ggagactgt gtttatgtct   2100
atggagaacc ctggactgtg gattctcgga tgccacaaca gtgactttcg taatagaggg   2160
atgactgcac tgctgaaggt gtccagctgt gataaaaata ctggcgacta ctacgaagat   2220
agctatgagg atatctcagc atacctgctg agcaagaata acgccatcga gccccgaagc   2280
ttctcacaga atccccctgt cctcaaggcc caccaggcgg agatcacaag gaccacactc   2340
cagtccgacc aggaggagat tgactacgat gacacgattt ctgtggagat gaaaaaagag   2400
gactttgaca tctacgatga ggatgaaaac cagagcccta ggtcgttcca gaagaaaaca   2460
aggcactact tcattgccgc cgtggagaga ctgtgggact acggaatgag tagttcccca   2520
cacgtgttgc ggaacagagc ccagagtggg tccgtcccac agttcaagaa ggttgttttc   2580
caggagttca cagatggctc cttcactcag ccactgtatc gcggcgagct gaatgagcac   2640
ttgggcttat tgggccccta cattcgcgca gaagtcgaag ataatattat ggtgaccttc   2700
cgcaaccagg ccagccggcc ttactcattc tactcctctc tcatctctta tgaggaggat   2760
cagcgccagg gcgccgaacc ccggaagaac tttgtgaagc ccaatgaaac caaaacttac   2820
ttttggaagg tgcagcacca tatggcgccg acgaaagacg aatttgactg caaagcctgg   2880
gcctacttca gcgacgtcga cttggagaag gacgtccaca gcggcctgat tggccctttg   2940
ttggtctgcc ataccaatac actcaaccct gcccacggga ggcaggtgac cgtgcaggag   3000
tttgccttgt tcttcaccat cttcgacgaa accaagagct ggtacttcac agagaacatg   3060
gagaggaact gcagagcacc ctgtaacatc cagatggagg accctacttt caaggaaaat   3120
tacaggttcc atgccattaa tggctacatc atggataccc tccccgggct tgtgatggct   3180
caggaccagc gcatccgctg gtacctgctc tcaatgggct ccaacgagaa cattcatagc   3240
atccacttta gtggccacgt gtttaccgtg cgcaagaagg aggagtacaa gatggcactg   3300
tacaacctgt accctggcgt gtttgagaca gtggagatgc tgccatccaa ggccggcatc   3360
tggcgcgtgg agtgcctcat tggggagcac ctccatgctg gcatgtctac actgttcctg   3420
```

-continued

```
gtgtacagca acaagtgtca gactccactc ggaatggcct ccgggcatat ccgcgatttt   3480

cagatcacgg cctctggcca gtatggccaa tgggctccca agctggccag gctgcactac   3540

agtgggagta tcaacgcttg gagcaccaag gagcctttct cctggatcaa ggtggacctg   3600

cttgccccca tgattattca cggcattaag acacaggggg ccaggcagaa attctcctcc   3660

ctgtacatct cccagttcat catcatgtac agtctggacg gcaaaaagtg gcagacctac   3720

cgcgggaaca gtaccgggac attgatggtg ttcttcggga acgtggactc tagcggcatt   3780

aaacacaaca ttttcaaccc ccccatcatt gctaggtata tcaggctcca tcccacccac   3840

tatagcatca ggtccactct gcggatggag ctgatgggct gcgaccttaa ttcatgcagc   3900

atgccgctgg gcatggagtc aaaggccatc tccgacgccc aaatcaccgc ctccagctac   3960

ttcaccaata tgttcgccac ctggagcccc agcaaggccc ggctgcacct gcagggccgc   4020

agcaacgcct ggcggcctca ggtgaacaac cccaaggagt ggctgcaggt ggacttccag   4080

aaaaccatga aggtgactgg ggtcaccacc cagggagtca agagcctgct gaccagcatg   4140

tatgtgaagg agttcttgat cagctcgtca caggatggcc accagtggac tttgttcttt   4200

cagaacggta aggtgaaagt gttccaggga aaccaagatt cctttacacc agtggtcaac   4260

tctctggatc ctcccctgct gacacggtac ctgcggatcc atccccagtc atgggtgcac   4320

cagattgctc tgcgcatgga ggtgcttggc tgcgaggccc aggacctgta ctga         4374
```

<210> SEQ ID NO 12
<211> LENGTH: 1457
<212> TYPE: PRT
<213> ORGANISM: Homo sapiens

<400> SEQUENCE: 12

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205
```

```
Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620
```

```
Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys His His Gln Arg Glu Ile Thr Arg Thr Thr Leu Gln Ser Asp Gln
    770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Ser Pro His Val Leu Arg Asn Arg Ala Gln
        835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu  Phe Ala Leu Phe Phe  Thr Ile Phe
        995                 1000                1005

Asp Glu  Thr Lys Ser Trp Tyr  Phe Thr Glu Asn Met  Glu Arg Asn
    1010                1015                1020

Cys Arg  Ala Pro Cys Asn Ile  Gln Met Glu Asp Pro  Thr Phe Lys
    1025                1030                1035

Glu Asn  Tyr Arg Phe His Ala  Ile Asn Gly Tyr Ile  Met Asp Thr
```

```
    1040                1045                1050

Leu Pro  Gly Leu Val Met Ala  Gln Asp Gln Arg Ile  Arg Trp Tyr
    1055                1060                1065

Leu Leu  Ser Met Gly Ser Asn  Glu Asn Ile His Ser  Ile His Phe
    1070                1075                1080

Ser Gly  His Val Phe Thr Val  Arg Lys Lys Glu Glu  Tyr Lys Met
    1085                1090                1095

Ala Leu  Tyr Asn Leu Tyr Pro  Gly Val Phe Glu Thr  Val Glu Met
    1100                1105                1110

Leu Pro  Ser Lys Ala Gly Ile  Trp Arg Val Glu Cys  Leu Ile Gly
    1115                1120                1125

Glu His  Leu His Ala Gly Met  Ser Thr Leu Phe Leu  Val Tyr Ser
    1130                1135                1140

Asn Lys  Cys Gln Thr Pro Leu  Gly Met Ala Ser Gly  His Ile Arg
    1145                1150                1155

Asp Phe  Gln Ile Thr Ala Ser  Gly Gln Tyr Gly Gln  Trp Ala Pro
    1160                1165                1170

Lys Leu  Ala Arg Leu His Tyr  Ser Gly Ser Ile Asn  Ala Trp Ser
    1175                1180                1185

Thr Lys  Glu Pro Phe Ser Trp  Ile Lys Val Asp Leu  Leu Ala Pro
    1190                1195                1200

Met Ile  Ile His Gly Ile Lys  Thr Gln Gly Ala Arg  Gln Lys Phe
    1205                1210                1215

Ser Ser  Leu Tyr Ile Ser Gln  Phe Ile Ile Met Tyr  Ser Leu Asp
    1220                1225                1230

Gly Lys  Lys Trp Gln Thr Tyr  Arg Gly Asn Ser Thr  Gly Thr Leu
    1235                1240                1245

Met Val  Phe Phe Gly Asn Val  Asp Ser Ser Gly Ile  Lys His Asn
    1250                1255                1260

Ile Phe  Asn Pro Pro Ile Ile  Ala Arg Tyr Ile Arg  Leu His Pro
    1265                1270                1275

Thr His  Tyr Ser Ile Arg Ser  Thr Leu Arg Met Glu  Leu Met Gly
    1280                1285                1290

Cys Asp  Leu Asn Ser Cys Ser  Met Pro Leu Gly Met  Glu Ser Lys
    1295                1300                1305

Ala Ile  Ser Asp Ala Gln Ile  Thr Ala Ser Ser Tyr  Phe Thr Asn
    1310                1315                1320

Met Phe  Ala Thr Trp Ser Pro  Ser Lys Ala Arg Leu  His Leu Gln
    1325                1330                1335

Gly Arg  Ser Asn Ala Trp Arg  Pro Gln Val Asn Asn  Pro Lys Glu
    1340                1345                1350

Trp Leu  Gln Val Asp Phe Gln  Lys Thr Met Lys Val  Thr Gly Val
    1355                1360                1365

Thr Thr  Gln Gly Val Lys Ser  Leu Leu Thr Ser Met  Tyr Val Lys
    1370                1375                1380

Glu Phe  Leu Ile Ser Ser Ser  Gln Asp Gly His Gln  Trp Thr Leu
    1385                1390                1395

Phe Phe  Gln Asn Gly Lys Val  Lys Val Phe Gln Gly  Asn Gln Asp
    1400                1405                1410

Ser Phe  Thr Pro Val Val Asn  Ser Leu Asp Pro Pro  Leu Leu Thr
    1415                1420                1425

Arg Tyr  Leu Arg Ile His Pro  Gln Ser Trp Val His  Gln Ile Ala
    1430                1435                1440
```

```
Leu Arg  Met Glu Val Leu Gly  Cys Glu Ala Gln Asp  Leu Tyr
    1445                1450                1455


<210> SEQ ID NO 13
<211> LENGTH: 1453
<212> TYPE: PRT
<213> ORGANISM: Homo sapiens

<400> SEQUENCE: 13

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
```

-continued

```
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
        755                 760                 765

Lys Glu Ile Thr Arg Thr Thr Leu Gln Ser Asp Gln Glu Glu Ile Asp
    770                 775                 780
```

Tyr Asp Asp Thr Ile Ser Val Glu Met Lys Lys Glu Asp Phe Asp Ile
785 790 795 800

Tyr Asp Glu Asp Glu Asn Gln Ser Pro Arg Ser Phe Gln Lys Lys Thr
805 810 815

Arg His Tyr Phe Ile Ala Ala Val Glu Arg Leu Trp Asp Tyr Gly Met
820 825 830

Ser Ser Ser Pro His Val Leu Arg Asn Arg Ala Gln Ser Gly Ser Val
835 840 845

Pro Gln Phe Lys Lys Val Val Phe Gln Glu Phe Thr Asp Gly Ser Phe
850 855 860

Thr Gln Pro Leu Tyr Arg Gly Glu Leu Asn Glu His Leu Gly Leu Leu
865 870 875 880

Gly Pro Tyr Ile Arg Ala Glu Val Glu Asp Asn Ile Met Val Thr Phe
885 890 895

Arg Asn Gln Ala Ser Arg Pro Tyr Ser Phe Tyr Ser Ser Leu Ile Ser
900 905 910

Tyr Glu Glu Asp Gln Arg Gln Gly Ala Glu Pro Arg Lys Asn Phe Val
915 920 925

Lys Pro Asn Glu Thr Lys Thr Tyr Phe Trp Lys Val Gln His His Met
930 935 940

Ala Pro Thr Lys Asp Glu Phe Asp Cys Lys Ala Trp Ala Tyr Phe Ser
945 950 955 960

Asp Val Asp Leu Glu Lys Asp Val His Ser Gly Leu Ile Gly Pro Leu
965 970 975

Leu Val Cys His Thr Asn Thr Leu Asn Pro Ala His Gly Arg Gln Val
980 985 990

Thr Val Gln Glu Phe Ala Leu Phe Phe Thr Ile Phe Asp Glu Thr Lys
995 1000 1005

Ser Trp Tyr Phe Thr Glu Asn Met Glu Arg Asn Cys Arg Ala Pro
1010 1015 1020

Cys Asn Ile Gln Met Glu Asp Pro Thr Phe Lys Glu Asn Tyr Arg
1025 1030 1035

Phe His Ala Ile Asn Gly Tyr Ile Met Asp Thr Leu Pro Gly Leu
1040 1045 1050

Val Met Ala Gln Asp Gln Arg Ile Arg Trp Tyr Leu Leu Ser Met
1055 1060 1065

Gly Ser Asn Glu Asn Ile His Ser Ile His Phe Ser Gly His Val
1070 1075 1080

Phe Thr Val Arg Lys Lys Glu Glu Tyr Lys Met Ala Leu Tyr Asn
1085 1090 1095

Leu Tyr Pro Gly Val Phe Glu Thr Val Glu Met Leu Pro Ser Lys
1100 1105 1110

Ala Gly Ile Trp Arg Val Glu Cys Leu Ile Gly Glu His Leu His
1115 1120 1125

Ala Gly Met Ser Thr Leu Phe Leu Val Tyr Ser Asn Lys Cys Gln
1130 1135 1140

Thr Pro Leu Gly Met Ala Ser Gly His Ile Arg Asp Phe Gln Ile
1145 1150 1155

Thr Ala Ser Gly Gln Tyr Gly Gln Trp Ala Pro Lys Leu Ala Arg
1160 1165 1170

Leu His Tyr Ser Gly Ser Ile Asn Ala Trp Ser Thr Lys Glu Pro
1175 1180 1185

Phe Ser Trp Ile Lys Val Asp Leu Leu Ala Pro Met Ile Ile His
1190 1195 1200

Gly Ile Lys Thr Gln Gly Ala Arg Gln Lys Phe Ser Ser Leu Tyr
1205 1210 1215

Ile Ser Gln Phe Ile Ile Met Tyr Ser Leu Asp Gly Lys Lys Trp
1220 1225 1230

Gln Thr Tyr Arg Gly Asn Ser Thr Gly Thr Leu Met Val Phe Phe
1235 1240 1245

Gly Asn Val Asp Ser Ser Gly Ile Lys His Asn Ile Phe Asn Pro
1250 1255 1260

Pro Ile Ile Ala Arg Tyr Ile Arg Leu His Pro Thr His Tyr Ser
1265 1270 1275

Ile Arg Ser Thr Leu Arg Met Glu Leu Met Gly Cys Asp Leu Asn
1280 1285 1290

Ser Cys Ser Met Pro Leu Gly Met Glu Ser Lys Ala Ile Ser Asp
1295 1300 1305

Ala Gln Ile Thr Ala Ser Ser Tyr Phe Thr Asn Met Phe Ala Thr
1310 1315 1320

Trp Ser Pro Ser Lys Ala Arg Leu His Leu Gln Gly Arg Ser Asn
1325 1330 1335

Ala Trp Arg Pro Gln Val Asn Asn Pro Lys Glu Trp Leu Gln Val
1340 1345 1350

Asp Phe Gln Lys Thr Met Lys Val Thr Gly Val Thr Thr Gln Gly
1355 1360 1365

Val Lys Ser Leu Leu Thr Ser Met Tyr Val Lys Glu Phe Leu Ile
1370 1375 1380

Ser Ser Ser Gln Asp Gly His Gln Trp Thr Leu Phe Phe Gln Asn
1385 1390 1395

Gly Lys Val Lys Val Phe Gln Gly Asn Gln Asp Ser Phe Thr Pro
1400 1405 1410

Val Val Asn Ser Leu Asp Pro Pro Leu Leu Thr Arg Tyr Leu Arg
1415 1420 1425

Ile His Pro Gln Ser Trp Val His Gln Ile Ala Leu Arg Met Glu
1430 1435 1440

Val Leu Gly Cys Glu Ala Gln Asp Leu Tyr
1445 1450

<210> SEQ ID NO 14
<211> LENGTH: 1454
<212> TYPE: PRT
<213> ORGANISM: Homo sapiens

<400> SEQUENCE: 14

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

Ala Lys Pro Arg Pro Pro Trp Met Gly Leu Leu Gly Pro Thr Ile Gln
85 90 95

-continued

```
Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510
```

Gly Val Lys His Leu Lys Asp Phe Pro Ile Leu Pro Gly Glu Ile Phe
515 520 525

Lys Tyr Lys Trp Thr Val Thr Val Glu Asp Gly Pro Thr Lys Ser Asp
530 535 540

Pro Arg Cys Leu Thr Arg Tyr Tyr Ser Ser Phe Val Asn Met Glu Arg
545 550 555 560

Asp Leu Ala Ser Gly Leu Ile Gly Pro Leu Leu Ile Cys Tyr Lys Glu
565 570 575

Ser Val Asp Gln Arg Gly Asn Gln Ile Met Ser Asp Lys Arg Asn Val
580 585 590

Ile Leu Phe Ser Val Phe Asp Glu Asn Arg Ser Trp Tyr Leu Thr Glu
595 600 605

Asn Ile Gln Arg Phe Leu Pro Asn Pro Ala Gly Val Gln Leu Glu Asp
610 615 620

Pro Glu Phe Gln Ala Ser Asn Ile Met His Ser Ile Asn Gly Tyr Val
625 630 635 640

Phe Asp Ser Leu Gln Leu Ser Val Cys Leu His Glu Val Ala Tyr Trp
645 650 655

Tyr Ile Leu Ser Ile Gly Ala Gln Thr Asp Phe Leu Ser Val Phe Phe
660 665 670

Ser Gly Tyr Thr Phe Lys His Lys Met Val Tyr Glu Asp Thr Leu Thr
675 680 685

Leu Phe Pro Phe Ser Gly Glu Thr Val Phe Met Ser Met Glu Asn Pro
690 695 700

Gly Leu Trp Ile Leu Gly Cys His Asn Ser Asp Phe Arg Asn Arg Gly
705 710 715 720

Met Thr Ala Leu Leu Lys Val Ser Ser Cys Asp Lys Asn Thr Gly Asp
725 730 735

Tyr Tyr Glu Asp Ser Tyr Glu Asp Ile Ser Ala Tyr Leu Leu Ser Lys
740 745 750

Asn Asn Ala Ile Glu Pro Arg Ser Phe Ser Gln Asn Pro Pro Val Leu
755 760 765

Lys Arg Glu Ile Thr Arg Thr Thr Leu Gln Ser Asp Gln Glu Glu Ile
770 775 780

Asp Tyr Asp Asp Thr Ile Ser Val Glu Met Lys Lys Glu Asp Phe Asp
785 790 795 800

Ile Tyr Asp Glu Asp Glu Asn Gln Ser Pro Arg Ser Phe Gln Lys Lys
805 810 815

Thr Arg His Tyr Phe Ile Ala Ala Val Glu Arg Leu Trp Asp Tyr Gly
820 825 830

Met Ser Ser Ser Pro His Val Leu Arg Asn Arg Ala Gln Ser Gly Ser
835 840 845

Val Pro Gln Phe Lys Lys Val Val Phe Gln Glu Phe Thr Asp Gly Ser
850 855 860

Phe Thr Gln Pro Leu Tyr Arg Gly Glu Leu Asn Glu His Leu Gly Leu
865 870 875 880

Leu Gly Pro Tyr Ile Arg Ala Glu Val Glu Asp Asn Ile Met Val Thr
885 890 895

Phe Arg Asn Gln Ala Ser Arg Pro Tyr Ser Phe Tyr Ser Ser Leu Ile
900 905 910

Ser Tyr Glu Glu Asp Gln Arg Gln Gly Ala Glu Pro Arg Lys Asn Phe
915 920 925

Val Lys Pro Asn Glu Thr Lys Thr Tyr Phe Trp Lys Val Gln His His

```
    930                 935                 940

Met Ala Pro Thr Lys Asp Glu Phe Asp Cys Lys Ala Trp Ala Tyr Phe
945                 950                 955                 960

Ser Asp Val Asp Leu Glu Lys Asp Val His Ser Gly Leu Ile Gly Pro
                965                 970                 975

Leu Leu Val Cys His Thr Asn Thr Leu Asn Pro Ala His Gly Arg Gln
            980                 985                 990

Val Thr Val Gln Glu Phe Ala Leu  Phe Phe Thr Ile Phe  Asp Glu Thr
        995                 1000                1005

Lys Ser  Trp Tyr Phe Thr Glu  Asn Met Glu Arg Asn  Cys Arg Ala
    1010                1015                1020

Pro Cys  Asn Ile Gln Met Glu  Asp Pro Thr Phe Lys  Glu Asn Tyr
    1025                1030                1035

Arg Phe  His Ala Ile Asn Gly  Tyr Ile Met Asp Thr  Leu Pro Gly
    1040                1045                1050

Leu Val  Met Ala Gln Asp Gln  Arg Ile Arg Trp Tyr  Leu Leu Ser
    1055                1060                1065

Met Gly  Ser Asn Glu Asn Ile  His Ser Ile His Phe  Ser Gly His
    1070                1075                1080

Val Phe  Thr Val Arg Lys Lys  Glu Glu Tyr Lys Met  Ala Leu Tyr
    1085                1090                1095

Asn Leu  Tyr Pro Gly Val Phe  Glu Thr Val Glu Met  Leu Pro Ser
    1100                1105                1110

Lys Ala  Gly Ile Trp Arg Val  Glu Cys Leu Ile Gly  Glu His Leu
    1115                1120                1125

His Ala  Gly Met Ser Thr Leu  Phe Leu Val Tyr Ser  Asn Lys Cys
    1130                1135                1140

Gln Thr  Pro Leu Gly Met Ala  Ser Gly His Ile Arg  Asp Phe Gln
    1145                1150                1155

Ile Thr  Ala Ser Gly Gln Tyr  Gly Gln Trp Ala Pro  Lys Leu Ala
    1160                1165                1170

Arg Leu  His Tyr Ser Gly Ser  Ile Asn Ala Trp Ser  Thr Lys Glu
    1175                1180                1185

Pro Phe  Ser Trp Ile Lys Val  Asp Leu Leu Ala Pro  Met Ile Ile
    1190                1195                1200

His Gly  Ile Lys Thr Gln Gly  Ala Arg Gln Lys Phe  Ser Ser Leu
    1205                1210                1215

Tyr Ile  Ser Gln Phe Ile Ile  Met Tyr Ser Leu Asp  Gly Lys Lys
    1220                1225                1230

Trp Gln  Thr Tyr Arg Gly Asn  Ser Thr Gly Thr Leu  Met Val Phe
    1235                1240                1245

Phe Gly  Asn Val Asp Ser Ser  Gly Ile Lys His Asn  Ile Phe Asn
    1250                1255                1260

Pro Pro  Ile Ile Ala Arg Tyr  Ile Arg Leu His Pro  Thr His Tyr
    1265                1270                1275

Ser Ile  Arg Ser Thr Leu Arg  Met Glu Leu Met Gly  Cys Asp Leu
    1280                1285                1290

Asn Ser  Cys Ser Met Pro Leu  Gly Met Glu Ser Lys  Ala Ile Ser
    1295                1300                1305

Asp Ala  Gln Ile Thr Ala Ser  Ser Tyr Phe Thr Asn  Met Phe Ala
    1310                1315                1320

Thr Trp  Ser Pro Ser Lys Ala  Arg Leu His Leu Gln  Gly Arg Ser
    1325                1330                1335
```

Asn Ala Trp Arg Pro Gln Val Asn Asn Pro Lys Glu Trp Leu Gln
1340 1345 1350

Val Asp Phe Gln Lys Thr Met Lys Val Thr Gly Val Thr Thr Gln
1355 1360 1365

Gly Val Lys Ser Leu Leu Thr Ser Met Tyr Val Lys Glu Phe Leu
1370 1375 1380

Ile Ser Ser Ser Gln Asp Gly His Gln Trp Thr Leu Phe Phe Gln
1385 1390 1395

Asn Gly Lys Val Lys Val Phe Gln Gly Asn Gln Asp Ser Phe Thr
1400 1405 1410

Pro Val Val Asn Ser Leu Asp Pro Pro Leu Leu Thr Arg Tyr Leu
1415 1420 1425

Arg Ile His Pro Gln Ser Trp Val His Gln Ile Ala Leu Arg Met
1430 1435 1440

Glu Val Leu Gly Cys Glu Ala Gln Asp Leu Tyr
1445 1450

<210> SEQ ID NO 15
<211> LENGTH: 1474
<212> TYPE: PRT
<213> ORGANISM: Homo sapiens

<400> SEQUENCE: 15

Met Gln Ile Glu Leu Ser Thr Cys Phe Phe Leu Cys Leu Leu Arg Phe
1 5 10 15

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

Ala Lys Pro Arg Pro Pro Trp Met Gly Leu Leu Gly Pro Thr Ile Gln
85 90 95

Ala Glu Val Tyr Asp Thr Val Val Ile Thr Leu Lys Asn Met Ala Ser
100 105 110

His Pro Val Ser Leu His Ala Val Gly Val Ser Tyr Trp Lys Ala Ser
115 120 125

Glu Gly Ala Glu Tyr Asp Asp Gln Thr Ser Gln Arg Glu Lys Glu Asp
130 135 140

Asp Lys Val Phe Pro Gly Gly Ser His Thr Tyr Val Trp Gln Val Leu
145 150 155 160

Lys Glu Asn Gly Pro Met Ala Ser Asp Pro Leu Cys Leu Thr Tyr Ser
165 170 175

Tyr Leu Ser His Val Asp Leu Val Lys Asp Leu Asn Ser Gly Leu Ile
180 185 190

Gly Ala Leu Leu Val Cys Arg Glu Gly Ser Leu Ala Lys Glu Lys Thr
195 200 205

Gln Thr Leu His Lys Phe Ile Leu Leu Phe Ala Val Phe Asp Glu Gly
210 215 220

Lys Ser Trp His Ser Glu Thr Lys Asn Ser Leu Met Gln Asp Arg Asp
225 230 235 240

Ala Ala Ser Ala Arg Ala Trp Pro Lys Met His Thr Val Asn Gly Tyr

-continued

```
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670
```

-continued

```
Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ala Thr Asn Val
        755                 760                 765

Ser Asn Asn Ser Asn Thr Ser Asn Asp Ser Asn Val Ser Pro Pro Val
    770                 775                 780

Leu Lys Arg His Gln Arg Glu Ile Thr Arg Thr Thr Leu Gln Ser Asp
785                 790                 795                 800

Gln Glu Glu Ile Asp Tyr Asp Asp Thr Ile Ser Val Glu Met Lys Lys
                805                 810                 815

Glu Asp Phe Asp Ile Tyr Asp Glu Asp Glu Asn Gln Ser Pro Arg Ser
            820                 825                 830

Phe Gln Lys Lys Thr Arg His Tyr Phe Ile Ala Ala Val Glu Arg Leu
        835                 840                 845

Trp Asp Tyr Gly Met Ser Ser Ser Pro His Val Leu Arg Asn Arg Ala
    850                 855                 860

Gln Ser Gly Ser Val Pro Gln Phe Lys Lys Val Val Phe Gln Glu Phe
865                 870                 875                 880

Thr Asp Gly Ser Phe Thr Gln Pro Leu Tyr Arg Gly Glu Leu Asn Glu
                885                 890                 895

His Leu Gly Leu Leu Gly Pro Tyr Ile Arg Ala Glu Val Glu Asp Asn
            900                 905                 910

Ile Met Val Thr Phe Arg Asn Gln Ala Ser Arg Pro Tyr Ser Phe Tyr
        915                 920                 925

Ser Ser Leu Ile Ser Tyr Glu Glu Asp Gln Arg Gln Gly Ala Glu Pro
    930                 935                 940

Arg Lys Asn Phe Val Lys Pro Asn Glu Thr Lys Thr Tyr Phe Trp Lys
945                 950                 955                 960

Val Gln His His Met Ala Pro Thr Lys Asp Glu Phe Asp Cys Lys Ala
                965                 970                 975

Trp Ala Tyr Phe Ser Asp Val Asp Leu Glu Lys Asp Val His Ser Gly
            980                 985                 990

Leu Ile Gly Pro Leu Leu Val Cys  His Thr Asn Thr Leu  Asn Pro Ala
        995                 1000                1005

His Gly  Arg Gln Val Thr Val  Gln Glu Phe Ala Leu  Phe Phe Thr
    1010                1015                1020

Ile Phe  Asp Glu Thr Lys Ser  Trp Tyr Phe Thr Glu  Asn Met Glu
    1025                1030                1035

Arg Asn  Cys Arg Ala Pro Cys  Asn Ile Gln Met Glu  Asp Pro Thr
    1040                1045                1050

Phe Lys  Glu Asn Tyr Arg Phe  His Ala Ile Asn Gly  Tyr Ile Met
    1055                1060                1065

Asp Thr  Leu Pro Gly Leu Val  Met Ala Gln Asp Gln  Arg Ile Arg
    1070                1075                1080
```

-continued

```
Trp Tyr  Leu Leu Ser Met Gly  Ser Asn Glu Asn Ile  His Ser Ile
    1085                 1090                 1095

His Phe  Ser Gly His Val Phe  Thr Val Arg Lys Lys  Glu Glu Tyr
    1100                 1105                 1110

Lys Met  Ala Leu Tyr Asn Leu  Tyr Pro Gly Val Phe  Glu Thr Val
    1115                 1120                 1125

Glu Met  Leu Pro Ser Lys Ala  Gly Ile Trp Arg Val  Glu Cys Leu
    1130                 1135                 1140

Ile Gly  Glu His Leu His Ala  Gly Met Ser Thr Leu  Phe Leu Val
    1145                 1150                 1155

Tyr Ser  Asn Lys Cys Gln Thr  Pro Leu Gly Met Ala  Ser Gly His
    1160                 1165                 1170

Ile Arg  Asp Phe Gln Ile Thr  Ala Ser Gly Gln Tyr  Gly Gln Trp
    1175                 1180                 1185

Ala Pro  Lys Leu Ala Arg Leu  His Tyr Ser Gly Ser  Ile Asn Ala
    1190                 1195                 1200

Trp Ser  Thr Lys Glu Pro Phe  Ser Trp Ile Lys Val  Asp Leu Leu
    1205                 1210                 1215

Ala Pro  Met Ile Ile His Gly  Ile Lys Thr Gln Gly  Ala Arg Gln
    1220                 1225                 1230

Lys Phe  Ser Ser Leu Tyr Ile  Ser Gln Phe Ile Ile  Met Tyr Ser
    1235                 1240                 1245

Leu Asp  Gly Lys Lys Trp Gln  Thr Tyr Arg Gly Asn  Ser Thr Gly
    1250                 1255                 1260

Thr Leu  Met Val Phe Phe Gly  Asn Val Asp Ser Ser  Gly Ile Lys
    1265                 1270                 1275

His Asn  Ile Phe Asn Pro Pro  Ile Ile Ala Arg Tyr  Ile Arg Leu
    1280                 1285                 1290

His Pro  Thr His Tyr Ser Ile  Arg Ser Thr Leu Arg  Met Glu Leu
    1295                 1300                 1305

Met Gly  Cys Asp Leu Asn Ser  Cys Ser Met Pro Leu  Gly Met Glu
    1310                 1315                 1320

Ser Lys  Ala Ile Ser Asp Ala  Gln Ile Thr Ala Ser  Ser Tyr Phe
    1325                 1330                 1335

Thr Asn  Met Phe Ala Thr Trp  Ser Pro Ser Lys Ala  Arg Leu His
    1340                 1345                 1350

Leu Gln  Gly Arg Ser Asn Ala  Trp Arg Pro Gln Val  Asn Asn Pro
    1355                 1360                 1365

Lys Glu  Trp Leu Gln Val Asp  Phe Gln Lys Thr Met  Lys Val Thr
    1370                 1375                 1380

Gly Val  Thr Thr Gln Gly Val  Lys Ser Leu Leu Thr  Ser Met Tyr
    1385                 1390                 1395

Val Lys  Glu Phe Leu Ile Ser  Ser Ser Gln Asp Gly  His Gln Trp
    1400                 1405                 1410

Thr Leu  Phe Phe Gln Asn Gly  Lys Val Lys Val Phe  Gln Gly Asn
    1415                 1420                 1425

Gln Asp  Ser Phe Thr Pro Val  Val Asn Ser Leu Asp  Pro Pro Leu
    1430                 1435                 1440

Leu Thr  Arg Tyr Leu Arg Ile  His Pro Gln Ser Trp  Val His Gln
    1445                 1450                 1455

Ile Ala  Leu Arg Met Glu Val  Leu Gly Cys Glu Ala  Gln Asp Leu
    1460                 1465                 1470

Tyr
```

<210> SEQ ID NO 16
<211> LENGTH: 461
<212> TYPE: PRT
<213> ORGANISM: Homo sapiens

<400> SEQUENCE: 16

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Leu
```

370 375 380

Ser Thr Lys Phe Thr Ile Tyr Asn Asn Met Phe Cys Ala Gly Phe His
385 390 395 400

Glu Gly Gly Arg Asp Ser Cys Gln Gly Asp Ser Gly Gly Pro His Val
405 410 415

Thr Glu Val Glu Gly Thr Ser Phe Leu Thr Gly Ile Ile Ser Trp Gly
420 425 430

Glu Glu Cys Ala Met Lys Gly Lys Tyr Gly Ile Tyr Thr Lys Val Ser
435 440 445

Arg Tyr Val Asn Trp Ile Lys Glu Lys Thr Lys Leu Thr
450 455 460

<210> SEQ ID NO 17
<211> LENGTH: 1386
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17
atgcagcgcg tgaacatgat tatggccgag tctcccggcc tgatcaccat ctgtctgctg 60
ggctatctgc tgagcgccga gtgcaccgtg tttctggatc acgagaacgc caacaagatc 120
ctgaacagac ccaagcggta caacagcggc aagctggaag agttcgtgca gggcaacctg 180
gaacgcgagt gcatggaaga gaagtgcagc ttcgaagagg ccagagaggt gttcgagaac 240
accgagagaa ccaccgagtt ctggaagcag tacgtggacg gcgatcagtg cgagagcaac 300
ccttgtctga atggcggcag ctgcaaggac gacatcaaca gctacgagtg ctggtgcccc 360
ttcggcttcg agggcaagaa ttgcgagctg gacgtgacct gcaacatcaa gaacggcaga 420
tgcgagcagt tctgcaagaa cagcgccgac aacaaggtcg tgtgctcctg cacagagggc 480
tacagactgg ccgagaacca gaagtcttgc gagcccgctg tgccctttcc atgtggcaga 540
gtgtctgtgt cccagaccag caagctgacc agagccgaga cagtgttccc cgacgtggac 600
tacgtgaaca gcaccgaggc cgagacaatc ctggacaaca tcacccagag cacccagtcc 660
ttcaacgact tcaccagagt cgtcggcggc gaggatgcta agcctggaca gtttccttgg 720
caagtggtgc tgaacggcaa ggtggacgct ttttgtggcg gctccatcgt gaacgagaag 780
tggatcgtga ccgccgctca ctgtgtggaa accggcgtga agattacagt ggtggccggc 840
gagcacaaca tcgaggaaac agagcacacc gagcagaaac ggaacgtgat cagaatcatc 900
cctcaccaca actacaacgc cgccatcaac aagtacaacc acgatatcgc cctgctggaa 960
ctggacgagc ccctggtcct gaactcttac gtgacccccta tctgtatcgc cgacaaagag 1020
tacaccaaca tctttctgaa gttcggcagc ggctacgtgt ccggctgggg aagagttttc 1080
cacaagggca gatcagccct ggtgctgcag tacctgagag tgcccctggt ggatagagcc 1140
acatgcctgc tgagcaccaa gttcaccatc tacaacaaca tgttctgcgc cggcttccac 1200
gaaggcggca gagattcttg tcaaggcgat tctggcggcc ctcacgtgac agaggttgag 1260
ggcacaagct ttctgaccgg catcatcagc tggggcgaag agtgtgccat gaaggggaag 1320
tacggcatct acaccaaggt gtccagatac gtgaactgga tcaaagaaaa gaccaagctc 1380
acctga 1386

<210> SEQ ID NO 18
<211> LENGTH: 466

<212> TYPE: PRT
<213> ORGANISM: Homo sapiens

<400> SEQUENCE: 18

Met Val Ser Gln Ala Leu Arg Leu Leu Cys Leu Leu Leu Gly Leu Gln
1 5 10 15

Gly Cys Leu Ala Ala Gly Gly Val Ala Lys Ala Ser Gly Gly Glu Thr
20 25 30

Arg Asp Met Pro Trp Lys Pro Gly Pro His Arg Val Phe Val Thr Gln
35 40 45

Glu Glu Ala His Gly Val Leu His Arg Arg Arg Arg Ala Asn Ala Phe
50 55 60

Leu Glu Glu Leu Arg Pro Gly Ser Leu Glu Arg Glu Cys Lys Glu Glu
65 70 75 80

Gln Cys Ser Phe Glu Glu Ala Arg Glu Ile Phe Lys Asp Ala Glu Arg
85 90 95

Thr Lys Leu Phe Trp Ile Ser Tyr Ser Asp Gly Asp Gln Cys Ala Ser
100 105 110

Ser Pro Cys Gln Asn Gly Gly Ser Cys Lys Asp Gln Leu Gln Ser Tyr
115 120 125

Ile Cys Phe Cys Leu Pro Ala Phe Glu Gly Arg Asn Cys Glu Thr His
130 135 140

Lys Asp Asp Gln Leu Ile Cys Val Asn Glu Asn Gly Gly Cys Glu Gln
145 150 155 160

Tyr Cys Ser Asp His Thr Gly Thr Lys Arg Ser Cys Arg Cys His Glu
165 170 175

Gly Tyr Ser Leu Leu Ala Asp Gly Val Ser Cys Thr Pro Thr Val Glu
180 185 190

Tyr Pro Cys Gly Lys Ile Pro Ile Leu Glu Lys Arg Asn Ala Ser Lys
195 200 205

Pro Gln Gly Arg Ile Val Gly Gly Lys Val Cys Pro Lys Gly Glu Cys
210 215 220

Pro Trp Gln Val Leu Leu Leu Val Asn Gly Ala Gln Leu Cys Gly Gly
225 230 235 240

Thr Leu Ile Asn Thr Ile Trp Val Val Ser Ala Ala His Cys Phe Asp
245 250 255

Lys Ile Lys Asn Trp Arg Asn Leu Ile Ala Val Leu Gly Glu His Asp
260 265 270

Leu Ser Glu His Asp Gly Asp Glu Gln Ser Arg Arg Val Ala Gln Val
275 280 285

Ile Ile Pro Ser Thr Tyr Val Pro Gly Thr Thr Asn His Asp Ile Ala
290 295 300

Leu Leu Arg Leu His Gln Pro Val Val Leu Thr Asp His Val Val Pro
305 310 315 320

Leu Cys Leu Pro Glu Arg Thr Phe Ser Glu Arg Thr Leu Ala Phe Val
325 330 335

Arg Phe Ser Leu Val Ser Gly Trp Gly Gln Leu Leu Asp Arg Gly Ala
340 345 350

Thr Ala Leu Glu Leu Met Val Leu Asn Val Pro Arg Leu Met Thr Gln
355 360 365

Asp Cys Leu Gln Gln Ser Arg Lys Val Gly Asp Ser Pro Asn Ile Thr
370 375 380

Glu Tyr Met Phe Cys Ala Gly Tyr Ser Asp Gly Ser Lys Asp Ser Cys
385 390 395 400

Lys Gly Asp Ser Gly Gly Pro His Ala Thr His Tyr Arg Gly Thr Trp
405 410 415

Tyr Leu Thr Gly Ile Val Ser Trp Gly Gln Gly Cys Ala Thr Val Gly
420 425 430

His Phe Gly Val Tyr Thr Arg Val Ser Gln Tyr Ile Glu Trp Leu Gln
435 440 445

Lys Leu Met Arg Ser Glu Pro Arg Pro Gly Val Leu Leu Arg Ala Pro
450 455 460

Phe Pro
465

<210> SEQ ID NO 19
<211> LENGTH: 1401
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19
atggtgtcac aggccctgag actgctgtgt ctgctgctgg gactgcaggg atgtttggct 60
gctggcggag tggctaaagc ctctggcgga gagacaagag acatgccctg gaagcctgga 120
cctcacagag tgttcgtgac ccaagaggaa gcccacggcg ttctgcacag aagaagaagg 180
gccaacgcct tcctggaaga actgaggcct ggctctctgg aacgcgagtg caaagaggaa 240
cagtgcagct tcgaggaagc cagagagatc ttcaaggacg ccgagcggac caagctgttc 300
tggatcagct acagcgacgg cgaccagtgt gccagctctc cttgtcagaa tggcggcagc 360
tgcaaggacc agctgcagag ctacatctgc ttttgcctgc ctgccttcga gggcagaaac 420
tgcgagacac acaaggacga ccagctgatc tgcgtgaacg agaacggcgg ctgcgagcag 480
tactgtagcg atcacacagg caccaagcgg agctgcagat gtcacgaggg ctattccctg 540
ctggccgatg gcgttagctg taccccctacc gtggaatacc cctgcggcaa gatccccatc 600
ctggaaaaga gaaacgccag caagccccag ggcagaatcg ttggcggcaa agtgtgccct 660
aagggcgagt gtccttggca ggttctgctg cttgtgaatg gcgctcagct gtgtggcggc 720
accctgatca ataccatctg ggtcgtgtcc gccgctcact gcttcgacaa gatcaagaac 780
tggcggaacc tgatcgccgt gctgggagag cacgatctgt ctgaacacga tggcgacgag 840
cagtctcgga gagtggccca agtgatcatc cccagcacct atgtgcccgg caccaccaat 900
cacgatatcg ccctgctcag actgcaccag cctgtggtgc tgacagatca cgtggtgcct 960
ctgtgcctgc cagagaggac ctttagcgag agaaccctgg ccttcgtgcg gttctctctg 1020
gtgtctggat ggggccagct gctggataga ggcgctacag ctctggaact gatggtgctg 1080
aacgtgccca gactgatgac ccaggattgc ctgcagcaga gcagaaaagt gggcgacagc 1140
cccaacatca ccgagtacat gttctgcgcc ggctactccg acggcagcaa ggatagctgt 1200
aaaggcgatt ctggcggccc tcacgccaca cactatagag gcacctggta tctgaccggc 1260
atcgtgtctt ggggacaggg ctgtgctaca gtgggccact ttggcgtgta caccagagtg 1320
tcccagtaca tcgagtggct gcagaaactc atgcggagcg agcctagacc tggcgtgttg 1380
ctgagagccc cttttcctta a 1401

<210> SEQ ID NO 20
<211> LENGTH: 1401
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 20

```
atggtgagcc aggccctgcg cctgctgtgc ctgctgctgg gcctgcaggg ctgcctggcc     60

gccggcggcg tggccaaggc cagcggcggc gagacccgcg acatgccctg gaagcccggc    120

ccccaccgcg tgttcgtgac ccaggaggag gcccacggcg tgctgcaccg ccgccgccgc    180

gccaacgcct tcctggagga gctgcgcccc ggcagcctgg agcgcgagtg caaggaggag    240

cagtgcagct tcgaggaggc ccgcgagatc ttcaaggacg ccgagcgcac caagctgttc    300

tggatcagct acagcgacgg cgaccagtgc gccagcagcc cctgccagaa cggcggcagc    360

tgcaaggacc agctgcagag ctacatctgc ttctgcctgc ccgccttcga gggccgcaac    420

tgcgagaccc acaaggacga ccagctgatc tgcgtgaacg agaacggcgg ctgcgagcag    480

tactgcagcg accacaccgg caccaagcgc agctgccgct gccacgaggg ctacagcctg    540

ctggccgacg gcgtgagctg cacccccacc gtggagtacc cctgcggcaa gatccccatc    600

ctggagaagc gcaacgccag caagccccag ggccgcatcg tgggcggcaa ggtgtgcccc    660

aagggcgagt gcccctggca ggtgctgctg ctggtgaacg gcgcccagct gtgcggcggc    720

accctgatca acaccatctg ggtggtgagc gccgcccact gcttcgacaa gatcaagaac    780

tggcgcaacc tgatcgccgt gctgggcgag cacgacctga gcgagcacga cggcgacgag    840

cagagccgcc gcgtggccca ggtgatcatc cccagcacct acgtgcccgg caccaccaac    900

cacgacatcg ccctgctgcg cctgcaccag cccgtggtgc tgaccgacca cgtggtgccc    960

ctgtgcctgc ccgagcgcac cttcagcgag cgcaccctgg ccttcgtgcg cttcagcctg   1020

gtgagcggct ggggccagct gctggaccgc ggcgccaccg ccctggagct gatggtgctg   1080

aacgtgcccc gcctgatgac ccaggactgc ctgcagcaga gccgcaaggt gggcgacagc   1140

cccaacatca ccgagtacat gttctgcgcc ggctacagcg acggcagcaa ggacagctgc   1200

aagggcgaca gcggcggccc ccacgccacc cactaccgcg gcacctggta cctgaccggc   1260

atcgtgagct ggggccaggg ctgcgccacc gtgggccact tcggcgtgta cacccgcgtg   1320

agccagtaca tcgagtggct gcagaagctg atgcgcagcg agccccgccc cggcgtgctg   1380

ctgcgcgccc ccttccccta a                                             1401
```

<210> SEQ ID NO 21
<211> LENGTH: 429
<212> TYPE: PRT
<213> ORGANISM: Homo sapiens

<400> SEQUENCE: 21

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
```

-continued

```
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425
```

<210> SEQ ID NO 22
<211> LENGTH: 1290
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
atgcagctga gaaaccccga actgcacctg ggatgtgccc tggctctgag atttctggcc      60

ctggtgtctt gggacatccc tggcgctaga gccctggata atggcctggc cagaacacct     120
```

acaatgggct ggctgcactg ggagagattc atgtgcaacc tggactgcca agaggaaccc 180
gacagctgca tcagcgagaa gctgttcatg gaaatggccg agctgatggt gtccgaaggc 240
tggaaggatg ccggctacga gtacctgtgc atcgacgact gttggatggc ccctcagaga 300
gactctgagg gcagactgca ggccgatcct cagagatttc cccacggcat tagacagctg 360
gccaactacg tgcacagcaa gggcctgaag ctgggcatct atgccgacgt gggcaacaag 420
acctgtgccg gctttcctgg cagcttcggc tactacgata tcgacgccca gaccttcgcc 480
gattggggag tcgatctgct gaagttcgac ggctgctact gcgacagcct ggaaaatctg 540
gccgacggct acaagcacat gtcactggcc ctgaatcgga ccggcagatc catcgtgtac 600
agctgcgagt ggcccctgta catgtggccc ttccagaagc ctaactacac cgagatcaga 660
cagtactgca accactggcg gaacttcgcc gacatcgacg atagctggaa gtccatcaag 720
agcatcctgg actggaccag cttcaatcaa gagcggatcg tggacgtggc aggacctggc 780
ggatggaacg atcctgacat gctggtcatc ggcaacttcg gcctgagctg gaaccagcaa 840
gtgacccaga tggccctgtg ggccattatg gccgctcctc tgttcatgag caacgacctg 900
agacacatca gccctcaggc caaggctctg ctgcaggaca aggatgtgat cgctatcaac 960
caggatcctc tgggcaagca gggctaccag ctgagacagg gcgacaattt cgaagtgtgg 1020
gaaagacccc tgagcggact ggcttgggcc gtcgccatga tcaacagaca agagatcggc 1080
ggaccccggt cctacacaat tgccgtggct tctctcggca aaggcgtggc ctgtaatccc 1140
gcctgcttta tcacacagct gctgcccgtg aagagaaagc tgggctttta cgagtggacc 1200
agcagactgc ggagccacat caatcctacc ggcacagtgc tgctgcagct ggaaaacacc 1260
atgcagatga gcctgaagga cctgctgtaa 1290

<210> SEQ ID NO 23
<211> LENGTH: 1290
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23
atgcagctgc gcaaccccga gctgcacctg ggctgcgccc tggccctgcg cttcctggcc 60
ctggtgagct gggacatccc cggcgcccgc gccctggaca acggcctggc ccgcaccccc 120
accatgggct ggctgcactg ggagcgcttc atgtgcaacc tggactgcca ggaggagccc 180
gacagctgca tcagcgagaa gctgttcatg gagatggccg agctgatggt gagcgagggc 240
tggaaggacg ccggctacga gtacctgtgc atcgacgact gctggatggc cccccagcgc 300
gacagcgagg gccgcctgca ggccgacccc cagcgcttcc cccacggcat ccgccagctg 360
gccaactacg tgcacagcaa gggcctgaag ctgggcatct acgccgacgt gggcaacaag 420
acctgcgccg gcttccccgg cagcttcggc tactacgaca tcgacgccca gaccttcgcc 480
gactggggcg tggacctgct gaagttcgac ggctgctact gcgacagcct ggagaacctg 540
gccgacggct acaagcacat gagcctggcc ctgaaccgca ccggccgcag catcgtgtac 600
agctgcgagt ggcccctgta catgtggccc ttccagaagc ccaactacac cgagatccgc 660
cagtactgca accactggcg caacttcgcc gacatcgacg acagctggaa gagcatcaag 720
agcatcctgg actggaccag cttcaaccag gagcgcatcg tggacgtggc cggccccggc 780
ggctggaacg accccgacat gctggtgatc ggcaacttcg gcctgagctg gaaccagcag 840

```
gtgacccaga tggccctgtg ggccatcatg gccgcccccc tgttcatgag caacgacctg    900

cgccacatca gcccccaggc caaggccctg ctgcaggaca aggacgtgat cgccatcaac    960

caggaccccc tgggcaagca gggctaccag ctgcgccagg gcgacaactt cgaggtgtgg   1020

gagcgccccc tgagcggcct ggcctgggcc gtggccatga tcaaccgcca ggagatcggc   1080

ggcccccgca gctacaccat cgccgtggcc agcctgggca agggcgtggc ctgcaacccc   1140

gcctgcttca tcacccagct gctgcccgtg aagcgcaagc tgggcttcta cgagtggacc   1200

agccgcctgc gcagccacat caaccccacc ggcaccgtgc tgctgcagct ggagaacacc   1260

atgcagatga gcctgaagga cctgctgtaa                                    1290


<210> SEQ ID NO 24
<211> LENGTH: 419
<212> TYPE: PRT
<213> ORGANISM: Homo sapiens

<400> SEQUENCE: 24

Met Gly Trp Arg Ala Ala Gly Ala Leu Leu Leu Ala Leu Leu Leu His
1               5                   10                  15

Gly Arg Leu Leu Ala Leu Asp Asn Gly Leu Ala Arg Thr Pro Thr Met
            20                  25                  30

Gly Trp Leu His Trp Glu Arg Phe Met Cys Asn Leu Asp Cys Gln Glu
        35                  40                  45

Glu Pro Asp Ser Cys Ile Ser Glu Lys Leu Phe Met Glu Met Ala Glu
    50                  55                  60

Leu Met Val Ser Glu Gly Trp Lys Asp Ala Gly Tyr Glu Tyr Leu Cys
65                  70                  75                  80

Ile Asp Asp Cys Trp Met Ala Pro Gln Arg Asp Ser Glu Gly Arg Leu
                85                  90                  95

Gln Ala Asp Pro Gln Arg Phe Pro His Gly Ile Arg Gln Leu Ala Asn
            100                 105                 110

Tyr Val His Ser Lys Gly Leu Lys Leu Gly Ile Tyr Ala Asp Val Gly
        115                 120                 125

Asn Lys Thr Cys Ala Gly Phe Pro Gly Ser Phe Gly Tyr Tyr Asp Ile
    130                 135                 140

Asp Ala Gln Thr Phe Ala Asp Trp Gly Val Asp Leu Leu Lys Phe Asp
145                 150                 155                 160

Gly Cys Tyr Cys Asp Ser Leu Glu Asn Leu Ala Asp Gly Tyr Lys His
                165                 170                 175

Met Ser Leu Ala Leu Asn Arg Thr Gly Arg Ser Ile Val Tyr Ser Cys
            180                 185                 190

Glu Trp Pro Leu Tyr Met Trp Pro Phe Gln Lys Pro Asn Tyr Thr Glu
        195                 200                 205

Ile Arg Gln Tyr Cys Asn His Trp Arg Asn Phe Ala Asp Ile Asp Asp
    210                 215                 220

Ser Trp Lys Ser Ile Lys Ser Ile Leu Asp Trp Thr Ser Phe Asn Gln
225                 230                 235                 240

Glu Arg Ile Val Asp Val Ala Gly Pro Gly Gly Trp Asn Asp Pro Asp
                245                 250                 255

Met Leu Val Ile Gly Asn Phe Gly Leu Ser Trp Asn Gln Gln Val Thr
            260                 265                 270

Gln Met Ala Leu Trp Ala Ile Met Ala Ala Pro Leu Phe Met Ser Asn
        275                 280                 285
```

-continued

```
Asp Leu Arg His Ile Ser Pro Gln Ala Lys Ala Leu Leu Gln Asp Lys
    290                 295                 300

Asp Val Ile Ala Ile Asn Gln Asp Pro Leu Gly Lys Gln Gly Tyr Gln
305                 310                 315                 320

Leu Arg Gln Gly Asp Asn Phe Glu Val Trp Glu Arg Pro Leu Ser Gly
                325                 330                 335

Leu Ala Trp Ala Val Ala Met Ile Asn Arg Gln Glu Ile Gly Gly Pro
            340                 345                 350

Arg Ser Tyr Thr Ile Ala Val Ala Ser Leu Gly Lys Gly Val Ala Cys
        355                 360                 365

Asn Pro Ala Cys Phe Ile Thr Gln Leu Leu Pro Val Lys Arg Lys Leu
    370                 375                 380

Gly Phe Tyr Glu Trp Thr Ser Arg Leu Arg Ser His Ile Asn Pro Thr
385                 390                 395                 400

Gly Thr Val Leu Leu Gln Leu Glu Asn Thr Met Gln Met Ser Leu Lys
                405                 410                 415

Asp Leu Leu
```

<210> SEQ ID NO 25
<211> LENGTH: 1260
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
atgggctggc gagctgctgg tgcacttctg ctggctctgc tgcttcatgg cagactgctt     60

gctctggaca acggcctggc ccgcaccccc accatgggct ggctgcactg ggagcgcttc    120

atgtgcaacc tggactgcca ggaggagccc gacagctgca tcagcgagaa gctgttcatg    180

gagatggccg agctgatggt gagcgagggc tggaaggacg ccggctacga gtacctgtgc    240

atcgacgact gctggatggc cccccagcgc gacagcgagg gccgcctgca ggccgacccc    300

cagcgcttcc cccacggcat ccgccagctg gccaactacg tgcacagcaa gggcctgaag    360

ctgggcatct acgccgacgt gggcaacaag acctgcgccg gcttccccgg cagcttcggc    420

tactacgaca tcgacgccca gaccttcgcc gactggggcg tggacctgct gaagttcgac    480

ggctgctact gcgacagcct ggagaacctg gccgacggct acaagcacat gagcctggcc    540

ctgaaccgca ccggccgcag catcgtgtac agctgcgagt ggcccctgta catgtggccc    600

ttccagaagc ccaactacac cgagatccgc cagtactgca accactggcg caacttcgcc    660

gacatcgacg acagctggaa gagcatcaag agcatcctgg actggaccag cttcaaccag    720

gagcgcatcg tggacgtggc cggccccggc ggctggaacg accccgacat gctggtgatc    780

ggcaacttcg gcctgagctg gaaccagcag gtgacccaga tggccctgtg ggccatcatg    840

gccgcccccc tgttcatgag caacgacctg cgccacatca gcccccaggc caaggccctg    900

ctgcaggaca aggacgtgat cgccatcaac caggaccccc tgggcaagca gggctaccag    960

ctgcgccagg gcgacaactt cgaggtgtgg gagcgccccc tgagcggcct ggcctgggcc   1020

gtggccatga tcaaccgcca ggagatcggc ggcccccgca gctacaccat cgccgtggcc   1080

agcctgggca agggcgtggc ctgcaacccc gcctgcttca tcacccagct gctgcccgtg   1140

aagcgcaagc tgggcttcta cgagtggacc agccgcctgc gcagccacat caaccccacc   1200

ggcaccgtgc tgctgcagct ggagaacacc atgcagatga gcctgaagga cctgctgtaa   1260
```

<210> SEQ ID NO 26
<211> LENGTH: 999
<212> TYPE: DNA
<213> ORGANISM: Homo sapiens

<400> SEQUENCE: 26
agtaccactt ttatactata aatatattta tactgtatat atttatatat atttatacta 60
tatatttttt tactatatat atttatacta tatatattta taagtatgtg ttcagcactg 120
tgacaattat tgttacaagg catgcttctt ttagatcata attgggatac aactagagcc 180
ttgatttttt tttttatttt cctttcgttt ttcatgcctg ttgactgagt gtatcttatt 240
tccatagatt gagtggggag cttgtgcact tgttctcaca ggaaacacag tcatctttgc 300
aactatacta ggctttttct tggtctttgg aagcaatgac gacttcagct ggcagcagtg 360
gtgaaaagaa attactgaac tattgtcaaa tggacttcct gtcatttgtt ggccattcac 420
gcacacagga gatggggcag ttaatgctga atggtatagc aagcctcttg gggtatttt 480 aggtgctccc ttctcacttt tattgtaagc atactatttt cacagagact tgctgaagga 540
ttaaaaggat tttctctttt ggaaaagctt gactgatttc acacttatct atagtatgct 600
ttttgtggtg tcctgctgaa tttaaatatt tatgtgtttt tcctgttagg ttgatttttt 660
ttggaatcaa tatgcaatgt taaacacttt tttaatgtaa tcatttgcat tggttaggaa 720
ttcagaattc cgccggctct attactggtc aagtacatct tttctcttaa aattatttag 780
cctccattat tacaaaaaat tataaaaata agttttcagt cagtcaggat gacatcactc 840
ccaatgttat gcagacatac agacggttgg catacgttat agactgtata ctcagtgcaa 900
atatagctgc atttatacct cagaggggcc aagtgttaat gcccatgccc tccgttaagg 960
gttgttggtt ttactggtag acagatgttt tgtggattg 999

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Arg Gly Asp Ser Pro
1 5

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Ser Trp Glu Leu Tyr Tyr Pro Leu Arg Ala Asn Leu
1 5 10

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

His Ala Val Asp Ile
1 5

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Asp Gly Glu Ala
1

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Phe Tyr Phe Asp Leu Arg
1 5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (3)..(3)
<223> OTHER INFORMATION: 4-hydroxyproline

<400> SEQUENCE: 32

Gly Phe Pro Gly Glu Arg
1 5

<210> SEQ ID NO 33
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (19)..(19)
<223> OTHER INFORMATION: 4-hydroxyproline

<400> SEQUENCE: 33

Pro Gly Pro Pro Gly Pro Pro Gly Pro Pro Gly Pro Pro Gly Pro Pro
1 5 10 15

Gly Phe Pro Gly Glu Arg Gly Pro Pro Gly Pro Pro Gly Pro Pro Gly
20 25 30

Pro Pro Gly Pro Pro
35

<210> SEQ ID NO 34
<211> LENGTH: 4
<212> TYPE: PRT

<213> ORGANISM: Artificial Sequence
<220> FEATURE:
<223> OTHER INFORMATION: Description of Artificial Sequence: Synthetic peptide

<400> SEQUENCE: 34

Val Ala Pro Gly
1

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Lys Gln Ala Gly Asp Val
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Pro His Ser Arg Asn
1               5

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Pro His Ser Arg Asn Gly Gly Gly Gly Gly Gly Arg Gly Asp Ser
1               5                   10                  15

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Arg Glu Asp Val
1

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Ile Lys Val Ala Val
1               5

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

```
Ser Arg Ala Arg Lys Gln Ala Ala Ser Ile Lys Val Ala Val Ala Asp
1               5                   10                  15

Arg
```

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

```
Lys Gln Leu Arg Glu Gln
1               5
```

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

```
Tyr Ile Gly Ser Arg
1               5
```

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

```
Ser Val Val Tyr Gly Leu Arg
1               5
```

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

```
Ala Glu Ile Asp Gly Ile Glu Leu
1               5
```

<210> SEQ ID NO 45
<211> LENGTH: 4
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 45

Val Thr Cys Gly
1

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Val Thr Cys Gly
1               5

<210> SEQ ID NO 47
<211> LENGTH: 6
<212> TYPE: PRT
<213> ORGANISM: Homo sapiens

<400> SEQUENCE: 47

Leu Lys Arg His Gln Arg
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Arg Gly Asp Ser Pro
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Arg Gly Asp Ser Pro
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Gly Gly Arg Gly Asp Ser Pro
1               5

<210> SEQ ID NO 51
<211> LENGTH: 4
<212> TYPE: PRT

-continued

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(4)
<223> OTHER INFORMATION: This sequence may encompass 1-4 residues

<400> SEQUENCE: 51

Gly Gly Gly Gly
1
```

MONOCLONAL CELL LINES EXPRESSING AN EXOGENOUS SUBSTANCE AND USES THEREOF

CROSS-REFERENCE TO RELATED APPLICATIONS

This application is a U.S. National Phase Application under 35 U.S.C. § 371 of International Application No. PCT/US2020/061524, filed Nov. 20, 2020, which claims priority to U.S. Provisional Application No. 62/938,995 filed on Nov. 22, 2019 and U.S. Provisional Application No. 63/004,212 filed on Apr. 2, 2020. The entire contents of each of the foregoing applications is hereby incorporated by reference.

BACKGROUND

Treating chronic and genetic diseases by implanting cells engineered to produce a therapeutic substance capable of treating such diseases has exciting potential to improve the health of patients with such diseases. To fully achieve the potential of such therapies, the implanted cells must be capable of producing therapeutic levels of the desired therapeutic substance for several weeks, months or even longer under conditions in which a selection marker is undesirable. Thus, a general approach to achieve stable, high level expression of the therapeutic substance is to implant engineered cells from a monoclonal cell line in which the therapeutic substance is encoded by an exogenous coding sequence inserted into one or more locations in the cell genome. However, generating a suitable monoclonal cell line is a time-consuming and expensive research endeavor because it is unpredictable which genomic locations will allow long-term acceptable expression levels of the therapeutic substance without transgene silencing and with minimal negative effects on the functioning and viability of the engineered cells.

SUMMARY

The present disclosure is based on the identification of specific open chromatin regions in the genome of a human retinal pigment epithelial (RPE) cell line that are suitable insertion sites for an exogenous transcription unit to achieve stable, high expression of a polypeptide encoded by the exogenous transcription unit.

Described herein is a genetically modified cell derived from a human cell, e.g., an immortalized human cell, and comprising at least one exogenous transcription unit inserted into at least one of three open chromatin regions (OCRs) located on Chromosomes 2, 5 and 12, or into at least one of four OCRs located on Chromosomes 2, 5, 8 and 12. In an embodiment, the insertion site of the transcription unit is defined by reference to certain nucleotide positions in the human hg19 reference genome (hg19) sequences for these chromosomes: the Chr 2 OCR is located between nucleotide positions corresponding to 100817157 and 100818556; the Chr 5 OCR is located nucleotide positions corresponding to 53853682 and 53854987; the Chr 12 OCR is located between nucleotide positions corresponding to 122186354 and 122187572. In an embodiment, the insertion site of the transcription unit in Chr 8 is defined by reference to certain nucleotide positions in the human hg38 reference genome (hg38) sequence for Chr 8: the OCR is located between nucleotide positions corresponding to 30,105,499 and 30,106,497. In another embodiment, the location of one or more of the OCRs is defined in reference to a nucleotide sequence present in the corresponding hg19 chromosome sequence: the Chr 2 OCR comprises SEQ ID NO:1 or a nucleotide sequence that is at least 90%, 95%, 98%, or 99% identical to SEQ ID NO:1; the Chr 5 OCR comprises SEQ ID NO:2 or a nucleotide sequence that is at least 90%, 95%, 98%, or 99% identical to SEQ ID NO:2; the Chr 8 OCR comprises SEQ ID NO:26 or a nucleotide sequence that is at least 90%, 95%, 98%, or 99% identical to SEQ ID NO:26; and the Chr 12 OCR comprises SEQ ID NO:3 or a nucleotide sequence that is at least 90%, 95%, 98%, or 99% identical to SEQ ID NO:3. In an embodiment, the exogenous transcription unit is inserted into one, two, three or four of the following locations: between two nucleotide positions corresponding to 211 and 218 in SEQ ID NO:1; between two nucleotide positions corresponding to 59 and 60 in SEQ ID NO:2; between two nucleotide positions corresponding to 440 and 445 in SEQ ID NO:26; and between two nucleotide positions corresponding to 518 and 525 in SEQ ID NO:3.

In an embodiment, the genetically modified cell is derived from a human epithelial cell. In an embodiment, the genetically modified cell is derived from an RPE cell, e.g, an immortalized human RPE cell. In an embodiment, the genetically modified cell is derived from a human cell line available from the American Type Culture Collection (Manassas, VA), e.g., the ARPE-19 (ATCC® CRL-2302™) cell line or the hTERT RPE-1 (ATCC® CRL-4000™) cell line.

In some embodiments, the exogenous transcription unit comprises a promoter sequence operably linked to a coding sequence for a polypeptide and a poly A signal sequence operably linked to the coding sequence. The promoter, poly A signal sequences are preferably selected to achieve high expression of the polypeptide in the parental human cell line. In an embodiment, the genetically modified cell is derived from the ARPE-19 cell line, the promoter consists essentially of, or consists of, SEQ ID NO:4 or SEQ ID NO:5, and the poly A signal sequence consists essentially of, or consists of, SEQ ID NO:6. The coding sequence is preferably codon-optimized for expression of the polypeptide in the parental cell line. In an embodiment, the polypeptide is constitutively expressed by the genetically modified cell when the cell is cultured in vitro. In an embodiment, the polypeptide is a blood clotting factor, e.g., a human FVIII protein.

The present disclosure also provides a composition comprising a plurality of genetically modified cells described herein and a method of manufacturing the composition. In an embodiment, the composition comprises a cell culture media or a storage medium. In an embodiment, the composition comprises a polymer solution in which the cells are suspended, e.g., a polymer solution described herein, e.g., comprising alginate and a cell-binding substance. In an embodiment, the method of manufacturing the composition comprises culturing a plurality of a genetically modified cell described herein until a desired number of cultured cells has been produced, and combining the desired number of cultured cells with a cell culture media, a storage medium or a polymer solution.

In yet another aspect, the present disclosure provides a device comprising at least one cell-containing compartment which comprises a genetically modified cell described herein or a plurality of such cells. In some embodiments, the device comprises a polymer composition encapsulating the genetically modified cell(s). In an embodiment, the encapsulating polymer composition comprises at least one cell binding-substance (CBS), e.g., a cell binding peptide, e.g., RGD or RGDSP. In some embodiments, the device further comprises at least one means for mitigating the foreign body response (FBR) when the device is placed inside a subject. In an embodiment, the means for mitigating the FBR comprises an afibrotic compound, as defined herein, disposed on an exterior surface of the device and/or within a barrier compartment surrounding the cell-containing compartment. In an embodiment, the afibrotic compound is a compound of Formula (I):

(I)

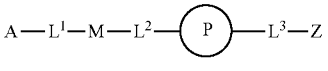

or a pharmaceutically acceptable salt thereof, wherein the variables A, L', M, $L^2$, P, $L^3$, and Z, as well as related subvariables, are defined herein. In some embodiments, the compound of Formula (I) or a pharmaceutically acceptable salt thereof (e.g., Formulas (I-a), (I-b), (I-c), (I-d), (I-e), (I-f), (II), (II-a), (III), (III-a), (III-b), (III-c), or (III-d)) is a compound described herein, including for example, one of the compounds shown in Table 3 herein. In an embodiment, the afibrotic compound is Compound 100, Compound 101 or Compound 102 shown in Table 3.

In one aspect, a device of the disclosure is a 2-compartment hydrogel capsule (e.g., a microcapsule (less than 1 mm in diameter) or a millicapsule (at least 1 mm in diameter)) in which a cell-containing compartment (e.g., the inner compartment) comprising a plurality of live genetically modified cells described herein (and optionally one or more cell binding substances) is surrounded by a barrier compartment comprising an afibrotic polymer (e.g., the outer compartment, e.g., hydrogel layer). In an embodiment, the afibrotic polymer comprises an afibrotic compound. In an embodiment, the afibrotic compound is a compound of Formula (I).

In another aspect, the present disclosure features a preparation (e.g., a composition) comprising a plurality (at least any of 3, 6, 12, 25, 50 or more) of a cell-containing device described herein, e.g, a preparation of hydrogel capsules encapsulating genetically modified RPE cells. In some embodiments, the preparation is a pharmaceutically acceptable composition.

In another aspect, the present disclosure features a method of making or manufacturing a device comprising a genetically modified cell described herein. In some embodiments, the method comprises providing the genetically modified cell, or a plurality of such cells, and disposing the cell(s) in an enclosing component, e.g., a cell-containing compartment of the device as described herein. In some embodiments, the enclosing component comprises a flexible polymer (e.g., PLA, PLG, PEG, CMC, or a polysaccharide, e.g., alginate). In some embodiments, the enclosing component comprises an inflexible polymer or metal housing. In some embodiments, the surface of the device is chemically modified, e.g., with a compound of Formula (I) as described herein.

In another aspect, the present disclosure features a method of evaluating a composition, device or device preparation described herein. In some embodiments, the method comprises providing the composition, device or device preparation and evaluating a functional parameter of the composition, device or device preparation. In an embodiment, the functional parameter is the amount of the exogenous polypeptide produced by the cells in the composition, device or device preparation in vitro (e.g., when placed in a suitable culture medium) and/or in vivo (e.g., after implant into a subject, e.g., a non-human subject or a human subject).

In another aspect, the present disclosure features a method of treating a subject in need of therapy with an exogenous polypeptide expressed by a genetically modified cell described herein. The method comprises administering to the subject a device or device preparation comprising the genetically modified cell. In some embodiments, the administering step comprises placing into the subject a pharmaceutically acceptable preparation comprising a plurality of devices, each of which has the ability to produce the exogenous polypeptide. In some embodiments, the device or device preparation is administered to, placed in, or provided to a site other than the central nervous system, brain, spinal column, eye, or retina. In some embodiments, the implantable element is administered to, placed in, or injected in the peritoneal cavity (e.g., the lesser sac), the omentum, or the subcutaneous fat of a subject. In an embodiment, the method further comprises measuring the amount or activity of the exogenous polypeptide present in a tissue sample removed from the subject, e.g., in plasma separated from a blood sample, a liver biopsy. In an embodiment, the tissue sample is removed at 15, 30, 60 or 120 days after administration, implantation, or placement of the device or device preparation. In some embodiments, the subject is a human. In an embodiment, the patient has been diagnosed with hemophilia A and the polypeptide is a FVIII protein.

The details of one or more embodiments of the disclosure are set forth herein. Other features, objects, and advantages of the disclosure will be apparent from the Detailed Description, the Figures, the Examples, and the Claims.

BRIEF DESCRIPTION OF THE DRAWINGS

FIGS. 1A-1D show nucleotide sequences from the human hg19 genome for four OCRs that contain suitable transcription unit insertion sites for genetically modified cells of the present disclosure, with FIG. 1A (SEQ ID NO:1) showing the reference nucleotide sequence of an OCR on Chr 2, FIG. 1B (SEQ ID NO:2) showing the reference nucleotide sequence of an OCR on Chr 5, FIG. 1C (SEQ ID NO:3) showing the reference nucleotide sequence of an OCR on Chr 12, FIG. 1D (SEQ ID NO:26) showing the reference nucleotide sequence of an OCR on Chr 8, and bold, italics underlining indicating the 5' and 3' boundaries of four specific insertion sites for an exogenous transcription unit encoding an FVIII-BDD protein in a clonal cell line derived from ARPE-19 cells.

FIG. 2 shows nucleotide sequences for various exogenous transcription unit elements that are useful to generate exemplary genetically modified cells of the present disclosure, with FIG. 2A and FIG. 2B showing nucleotide sequences of two different promoters (SEQ ID NO: 4 and SEQ ID NO:5), FIG. 2C showing the nucleotide sequence of a poly A signal sequence (SEQ ID NO:6), and FIG. 2D showing the nucleotide sequence of a complete exemplary transcription unit (SEQ ID NO:7), with underlining indicating the promoter sequence, shading indicating the Kozak sequence, [ORF] indicating the insertion site for a coding sequence for a polypeptide of interest, and bold italics indicating the polyA signal sequence.

FIG. 3A shows the amino acid sequence (SEQ ID NO:8) of an exemplary human FVIII-BDD protein, with underlining indicating the signal peptide.

FIG. 3B shows an exemplary codon optimized nucleotide sequence (SEQ ID NO:9) for expressing the human FVIII-BDD protein of SEQ ID NO:8 in a genetically modified ARPE-19 cell of the present disclosure.

FIG. 3C shows the amino acid sequence (SEQ ID NO:10) of an exemplary human single chain FVIII-BDD protein, with underlining indicating the signal peptide.

FIG. 3D shows an exemplary codon optimized nucleotide sequence (SEQ ID NO:11) for expressing the human single-chain FVIII-BDD protein of SEQ ID NO:10 in genetically modified ARPE-19 cell of the present disclosure.

FIGS. 3E, 3F and 3G show the amino acid sequences (SEQ ID NO:12, 13 and 14) of other exemplary human single chain FVIII-BDD proteins, with underlining indicating the signal peptide.

FIG. 311 shows the amino acid sequence (SEQ ID NO:15) of another exemplary human FVIII-BDD protein, with underlining indicating the signal peptide.

FIG. 4A shows the amino acid sequence (SEQ ID NO:16) of an exemplary human FIX protein, with underlining indicating the signal peptide.

FIG. 4B shows an exemplary codon optimized nucleotide sequence (SEQ ID NO:17) for expressing the human FIX protein of SEQ ID NO:16 in a genetically modified ARPE-19 cell of the present disclosure.

FIG. 5A shows the amino acid sequence (SEQ ID NO:18) of an exemplary human FVII protein, with underlining indicating the signal peptide.

FIG. 5B and FIG. 5C show exemplary codon optimized nucleotide sequences (SEQ ID NO:19 and SEQ ID NO:20) for expressing the human FVII protein of SEQ ID NO:18 in a genetically modified ARPE-19 cell of the present disclosure.

FIG. 6A shows the amino acid sequence (SEQ ID NO:21) of an exemplary human GLA protein, with underlining indicating the signal peptide.

FIG. 6B and FIG. 6C show exemplary codon optimized nucleotide sequences (SEQ ID NO:22 and SEQ ID NO:23)) for expressing the human GLA protein of SEQ ID NO:21 in a genetically modified ARPE-19 cell of the present disclosure.

FIG. 6D shows the amino acid sequence (SEQ ID NO:24) of an exemplary human GLA fusion protein, with underlining indicating the signal peptide.

FIG. 6E shows an exemplary codon optimized nucleotide sequence (SEQ ID NO:25) for expressing the human GLA fusion protein of SEQ ID NO:24 in a genetically modified ARPE-19 cell of the present disclosure.

DETAILED DESCRIPTION

Figure 7:
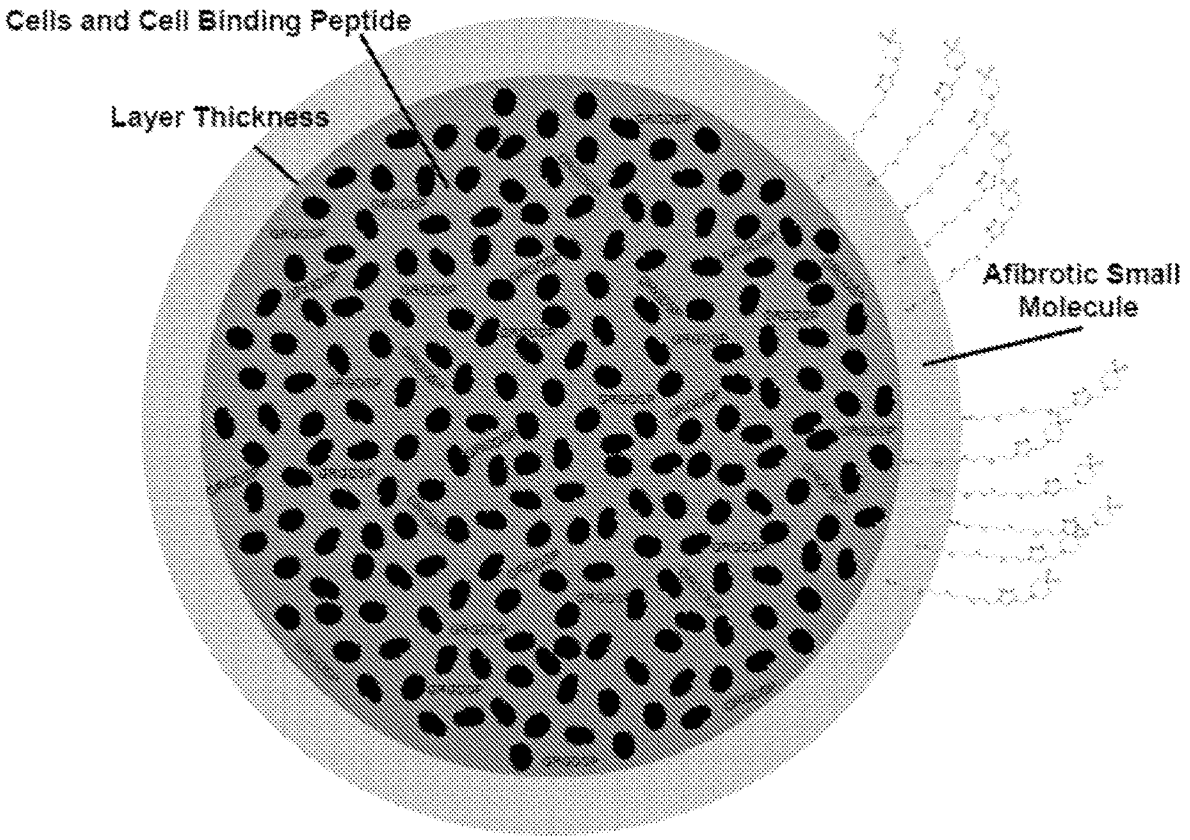
FIG. 7 illustrates an exemplary device of the disclosure (e.g., a two compartment hydrogel capsule), with lines indicating: a first, inner compartment formed from a polymer covalently attached to a cell binding peptide and genetically modified cells encapsulated therein; a second compartment (e.g., layer); and an afibrotic compound disposed within the second compartment and on the surface of the capsule.

The present disclosure features genetically modified human cells (e.g., derived from human RPE cells, e.g., ARPE-19 cells), which have been engineered to produce an exogenous polypeptide of interest by inserting an exogenous transcription unit into one or more specific genomic OCRs that have been shown to allow stable, high level expression of a polypeptide encoded by the transcription unit. The present disclosure also provides compositions, devices and device preparations comprising such genetically modified cells. In some embodiments, the genetically modified cells, compositions, and devices are useful for delivering a therapeutic polypeptide to a subject in need of treatment with the therapeutic polypeptide.

Definitions

So that the disclosure may be more readily understood, certain technical and scientific terms used herein are specifically defined below. Unless specifically defined elsewhere in this document, all other technical and scientific terms used herein have the meaning commonly understood by one of ordinary skill in the art to which this disclosure belongs.

As used herein, including the appended claims, the singular forms of words such as "a," "an," and "the," include their corresponding plural references unless the context clearly dictates otherwise.

"About" or "approximately" when used herein to modify a numerically defined parameter (e.g., amount of genetically modified cells in a composition or device (e.g., hydrogel capsule), a physical description of a device such as diameter, sphericity, number of cells encapsulated therein, the number of devices in a preparation), means that the recited numerical value is within an acceptable functional range for the defined parameter as determined by one of ordinary skill in the art, which will depend in part on how the numerical value is measured or determined, e.g., the limitations of the measurement system, including the acceptable error range for that measurement system. For example, "about" can mean a range of 20% above and below the recited numerical value. As a non-limiting example, a device defined as having a diameter of about 1.5 millimeters (mm) and encapsulating about 5 million (M) cells may have a diameter of 1.2 to 1.8 mm and may encapsulate 4 M to 6 M cells. As another non-limiting example, a preparation of about 100 devices (e.g., hydrogel capsules) includes preparations having 80 to 120 devices. In some embodiments, the term "about" means that the modified parameter may vary by as much as 15%, 10% or 5% above and below the stated numerical value for that parameter.

"Acquire" or "acquiring" as used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., performing an analytical method or protocol) to obtain the value or physical entity. "Indirectly acquiring" refers to receiving the value or physical entity from another party or source (e.g., a third party laboratory that directly acquired the physical entity or value). Directly acquiring a value or physical entity includes performing a process that includes a physical change in a physical substance or the use of a machine or device. Examples of directly acquiring a value include obtaining a sample from a human subject. Directly acquiring a value includes performing a process that uses a machine or device, e.g., using a fluorescence microscope to acquire fluorescence microscopy data.

"Administer," "administering," or "administration," as used herein, refer to implanting, absorbing, ingesting, injecting, placing or otherwise introducing into a subject, an entity described herein (e.g., a device or a preparation of devices), or providing such an entity to a subject for administration.

"Afibrotic", as used herein, means a compound or material that mitigates the foreign body response (FBR) to an implanted device. For example, the amount of FBR in a biological tissue that is induced by implant into that tissue of a device (e.g., a hydrogel capsule) comprising an afibrotic compound (e.g., a hydrogel capsule comprising a polymer covalently modified with a compound listed in Table 3) is lower than the FBR induced by implantation of an afibrotic-null reference device, i.e., a device that lacks any afibrotic compound, but is of substantially the same composition (e.g., same CBP-polymer, same cell type(s)) and structure (e.g., size, shape, no. of compartments). In an embodiment, the degree of the FBR is assessed by the immunological response in the tissue containing the implanted device (e.g., hydrogel capsule), which may include, for example, protein adsorption, macrophages, multinucleated foreign body giant cells, fibroblasts, and angiogenesis, using assays known in the art, e.g., as described in WO 2017/075630, or using one or more of the assays/methods described Vegas, A., et al., *Nature Biotechnol* (*supra*), (e.g., subcutaneous cathepsin measurement of implanted capsules, Masson's trichrome (MT), hematoxylin or eosin staining of tissue sections, quantification of collagen density, cellular staining and confocal microscopy for macrophages (CD68 or F4/80), myofibroblasts (alpha-muscle actin, SMA) or general cellular deposition, quantification of 79 RNA sequences of known inflammation factors and immune cell markers, or FACS analysis for macrophage and neutrophil cells on retrieved devices (e.g., capsules) after 14 days in the intraperitoneal space of a suitable test subject, e.g., an immunocompetent mouse. In an embodiment, the FBR is assessed by measuring the levels in the tissue containing the implant of one or more biomarkers of immune response, e.g., cathepsin, TNF-α, IL-13, IL-6, G-CSF, GM-CSF, IL-4, CCL2, or CCL4. In some embodiments, the FBR induced by a device of the invention (e.g., a hydrogel capsule comprising an afibrotic compound disposed on its outer surface), is at least about 80%, about 85%, about 90%, about 95%, about 99%, or about 100% lower than the FBR induced by an FBR-null reference device, e.g., a device that is substantially identical to the test or claimed device except for lacking the means for mitigating the FBR (e.g., a hydrogel capsule that does not comprise an afibrotic compound but is otherwise substantially identical to the claimed capsule. In some embodiments, the FBR (e.g., level of a biomarker(s)) is measured after about 30 minutes, about 1 hour, about 6 hours, about 12 hours, about 1 day, about 2 days, about 3 days, about 4 days, about 1 week, about 2 weeks, about 1 month, about 2 months, about 3 months, about 6 months, or longer.

"Alpha-galactosidase A" "α-Gal A", "alpha-D-galactosidase-A", alpha-galactoside galactohydrolase", "galactosidase alpha", and "GLA protein" may be used interchangeably herein and refer to a homodimeric protein comprising the mature amino acid sequence encoded by a wild-type mammalian GLA gene or an amino acid sequence with conservative substitutions thereof. In an embodiment, the conservatively substituted GLA protein has enzyme activity that is within 80-120%, 85-115%, 90-110% or 95-105% of the corresponding wild-type mammalian mature GLA protein, as measured by a GLA activity assay described herein. The wild-type human GLA gene encodes a 429-amino acid polypeptide, of which the N-terminal 31 amino acids constitute a signal peptide. The full DNA sequence of the wild-type human GLA gene, including introns and exons, is available in GenBank Accession No. X14448.1. The amino acid sequence for wild-type human precursor α-Gal A is available in GenBank Accession Nos. X14448.1 and U78027 and shown in FIG. 6A (SEQ ID NO:21). In some embodiments, the term "GLA protein" (and any of the aforesaid synonyms) refers to a polypeptide comprising the wild-type mature amino acid sequence shown in FIG. 6A, and optionally preceded by the GLA signal peptide (underlined in FIG. 6A) or by a signal peptide for a different secretory protein, e.g., a protein secreted by human cells (e.g., human epithelial cells), e.g., the signal peptide for HSPG2, as shown in FIG. 6D, which is also referred to herein as a GLA fusion protein.

"Cell," as used herein, refers to a human cell that is engineered (genetically modified) or a human cell that is not engineered (not genetically modified). In an embodiment, a cell is an immortalized cell, or an engineered cell derived from an immortalized human cell line. In an embodiment, the cell is a live cell, e.g., is viable as measured by any technique described herein or known in the art.

"Cell-binding peptide (CBP)", as used herein, means a linear or cyclic peptide that comprises an amino acid sequence that is derived from the cell binding domain of a ligand for a cell-adhesion molecule (CAM) (e.g., that mediates cell-matrix junctions or cell-cell junctions). The CBP is less than 50, 40 30, 25, 20, 15 or 10 amino acids in length. In an embodiment, the CBP is between 3 and 12 amino acids, 4 and 10 amino acids in length, or is 3, 4, 5, 6, 7 8, 9 or 10 amino acids in length. The CBP amino acid sequence may be identical to the naturally occurring binding domain sequence or may be a conservatively substituted variant thereof. In an embodiment, the CAM ligand is a mammalian protein. In an embodiment, the CAM ligand is a human protein selected from the group of proteins listed in Table 1 below. In an embodiment, the CBP comprises, consists essentially of, or consists of a cell binding sequence listed in Table 1 below or a conservatively substituted variant thereof. In an embodiment, the CBP is an RGD peptide, which means the peptide comprises the amino acid sequence RGD and optionally comprises one or more additional amino acids located at the N-terminus and/or the C-terminus. In an embodiment, the CBP is a cyclic peptide comprising RGD, e.g., one of the cyclic RGD peptides described in Vilaca, H. et al., *Tetrahedron* 70 (35):5420-5427 (2014). In an embodiment, the CBP is a linear peptide comprising RGD and is less than 6 amino acids in length. In an embodiment, the CBP is a linear peptide that consists essentially of RGD or RGDSP.

TABLE 1

Exemplary CAM Ligand Proteins and Cell Binding Sequences

| Protein | Cell Binding Sequence |
|---|---|
| E-cadherin | SWELYYPLRANL |
| N-cadherin | HAVDI |
| Collagen I | DGEA |
| Collagen IV | FYFDLR<br>GFOGER, where O is 4-hydroxyproline<br>P(GPP)$_5$GFOGER(GPP)$_5$,<br>where O is 4-hydroxyproline |
| Elastin | VAPG |
| Fibrinogen | RGD<br>GPR |
| Fibronectin | RGD<br>KQAGDV<br>PHSRN<br>PHSRNGGGGGGRGDS<br>REDV |

TABLE 1-continued

| Exemplary CAM Ligand Proteins and Cell Binding Sequences | |
|---|---|
| Protein | Cell Binding Sequence |
| Laminin | IKVAV<br>SRARKQAASIKVAVADR<br>LRE<br>KQLREQ<br>YIGSR |
| Nidogen-1 | RGD |
| Osteopontin | SVVYGLR |
| Tenascin C (TN-C) | AEIDGIEL |
| Tenascin-R | RGD |
| Tenascin-X | RGD |
| Thrombospondin | VTCG<br>SVTCG |
| Vitronectin | RGD |
| Von Willebrand Factor | RGD |

"CBP-polymer", as used herein, means a polymer comprising at least one cell-binding peptide molecule covalently attached to the polymer via a linker. In an embodiment, the polymer in the CBP-polymer is not a peptide or a polypeptide. In an embodiment, the polymer in a CBP-polymer is a synthetic or naturally occurring polysaccharide, e.g., an alginate, e.g., a sodium alginate. In an embodiment, the linker is an amino acid linker (i.e., consists essentially of a single amino acid, or a peptide of several identical or different amino acids), which is joined via a peptide bond to the N-terminus or C-terminus of the CBP. In an embodiment, the C-terminus of an amino acid linker is joined to the N-terminus of the CBP and the N-terminus of the amino acid linker is joined to at least one pendant carboxyl group in the polysaccharide via an amide bond. In an embodiment, the structure of the linker-CBP is expressed as $G_{(1-4)}$-CBP, meaning that the linker has one, two, three or four glycine residues. In an embodiment, one or more of the monosaccharide moieties in a CBP-polysaccharide, e.g., a CBP-alginate) is not modified with the CBP, e.g, the unmodified moiety has a free carboxyl group or lacks a modifiable pendant carboxyl group. In an embodiment, the number of polysaccharide moieties with a covalently attached CBP is less than any of the following values: 99%, 95%, 90%, 80%, 70%, 60%, 50%, 40% 30%, 20%, 10%, 5%, 1%.

"Cell-binding polypeptide (CBPP)", as used herein, means a polypeptide of at least 50, at least 75, or at least 100 amino acids in length and comprising the amino acid sequence of a cell binding domain of a CAM ligand, or a conservatively substituted variant thereof. In an embodiment, the CAM ligand is a mammalian protein. In an embodiment, the CBPP amino acid comprises the naturally occurring amino acid sequence of a full-length CAM ligand, e.g., one of the proteins listed in Table 1 below, or a conservatively substituted variant thereof.

"Cell-binding substance (CBS)", as used herein, means any chemical, biological or other type of substance (e.g., a small organic compound, a peptide, a polypeptide) that is capable of mimicking at least one activity of a ligand for a cell-adhesion molecule (CAM) or other cell-surface molecule that mediates cell-matrix junctions or cell-cell junctions or other receptor-mediated signaling. In an embodiment, when present in a polymer composition encapsulating live cells, the CBS is capable of forming a transient or permanent bond or contact with one or more of the cells. In an embodiment, the CBS facilitates interactions between two or more live cells encapsulated in the polymer composition. In an embodiment, the CBS is physically attached to one or more polymer molecules in the polymer composition. In an embodiment, the CBS is a cell-binding peptide or cell-binding polypeptide, as defined herein.

"Conservatively modified variants" or conservative substitution", as used herein, refers to a variant of a reference peptide or polypeptide that is identical to the reference molecule, except for having one or more conservative amino acid substitutions in its amino acid sequence. In an embodiment, a conservatively modified variant consists of an amino acid sequence that is at least 70%, 80%, 85%, 90%, 95%, 97%, 98% or 99% identical to the reference amino acid sequence. A conservative amino acid substitution refers to substitution of an amino acid with an amino acid having similar characteristics (e.g., charge, side-chain size, hydrophobicity/hydrophilicity, backbone conformation and rigidity, etc.) and which has minimal impact on the biological activity of the resulting substituted peptide or polypeptide. Conservative substitution tables of functionally similar amino acids are well known in the art, and exemplary substitutions grouped by functional features are set forth in Table 2 below.

TABLE 2

| Exemplary conservative amino acid substitution groups. | |
|---|---|
| Feature | Conservative Amino Group |
| Charge/Polarity | His, Arg, Lys |
| | Asp, Glu |
| | Cys, Thr, Ser, Gly, Asn, Gln, Tyr |
| | Ala, Pro, Met, Leu, Ile, Val, Phe, Trp |
| Hydrophobicity | Asp, Glu, Asn, Gln, Arg, Lys |
| | Cys, Ser, Thr, Pro, Gly, His, Tyr |
| | Ala, Met, Ile Leu, Val, Phe, Trp |
| Structural/Surface Exposure | Asp, Glu, Asn, Aln, His, Arg, Lys |
| | Cys, Ser, Tyr, Pro, Ala, Gly, Trp, Tyr |
| | Met, Ile, Leu, Val, Phe |
| Secondary Structure Propensity | Ala, Glu, Aln, His, Lys, Met, Leu, Arg |
| | Cys, Thr, Ile, Val, Phe, Tyr, Trp |
| | Ser, Gly, Pro, Asp, Asn |
| Evolutionary Conservation | Asp, Glu |
| | His, Lys, Arg |
| | Asn, Gln |
| | Ser, Thr |
| | Leu, Ile, Val |
| | Phe, Tyr, Trp |
| | Ala, Gly |
| | Met, Cys |

"Consists essentially of", and variations such as "consist essentially of" or "consisting essentially of" as used throughout the specification and claims, indicate the inclusion of any recited elements or group of elements, and the optional inclusion of other elements, of similar or different nature than the recited elements, that do not materially change the basic or novel properties of the specified molecule, composition, device, or method. As a non-limiting example, a cell-binding peptide or an FVIII protein that consists essentially of a recited amino acid sequence may also include one or more amino acids, including substitutions in the recited amino acid sequence, of one or more amino acid residues, which do not materially affect the relevant biological activity of the cell-binding peptide or the FVIII protein, respectively.

"Derived from", as used herein with respect to a cell or cells, refers to cells obtained from tissue, cell lines, or cells, which optionally are then cultured, passaged, immortalized, differentiated and/or induced, etc. to produce the derived cell(s).

"Device", as used herein, refers to any implantable object (e.g., a particle, a hydrogel capsule, an implant, a medical device), which contains live, genetically modified human cells (e.g., derived from RPE cells) capable of expressing, and optionally secreting, an exogenous polypeptide following implant of the device, and has a configuration that supports the viability of the cells by allowing cell nutrients to enter the device. In some embodiments, the device allows release from the device of metabolic byproducts generated by the cells.

"Effective amount", as used herein, refers to an amount of genetically modified cells (e.g., derived from human cells (e.g., epithelial cells)) producing an exogenous polypeptide or a device preparation producing the polypeptide that is sufficient to elicit a desired biological response. In an embodiment, the desired biological response is an increase in levels of the exogenous polypeptide within the cells, or for secreted polypeptides, in a tissue sample removed from a subject treated with (e.g., implanted with) the genetically modified cells, a device or a device preparation containing such cells. As will be appreciated by those of ordinary skill in this art, the effective amount may vary depending on such factors as the desired biological endpoint, the pharmacokinetics of the exogenous polypeptide, composition or device, the condition being treated, the mode of administration, and the age and health of the subject. An effective amount encompasses therapeutic and prophylactic treatment.

An "endogenous nucleic acid" as used herein, is a nucleic acid that occurs naturally in a subject cell.

An "endogenous polypeptide," as used herein, is a polypeptide that occurs naturally in a subject cell.

"Engineered human cell" and "genetically modified human cell", may be used interchangeably herein, and each term means a human cell (e.g., an epithelial cell) having a non-naturally occurring genetic alteration (e.g., in the cellular genome), and typically comprises an exogenous nucleic acid sequence (e.g., DNA or RNA) not present (or present at a different level than) in an otherwise similar human cell (e.g., epithelial cell) that is not engineered. In an embodiment, an engineered human cell (e.g., engineered RPE cell) comprises an exogenous nucleic acid encoding a polypeptide, e.g., a therapeutic protein. In an embodiment, the exogenous nucleic acid sequence is chromosomal (e.g., the exogenous nucleic acid sequence is an exogenous sequence disposed in endogenous chromosomal sequence) or is extra chromosomal (e.g., a non-integrated expression vector). In an embodiment, the exogenous nucleic acid sequence comprises an RNA sequence, e.g., an mRNA. In an embodiment, the exogenous nucleic acid sequence comprises a chromosomal or extra-chromosomal exogenous nucleic acid sequence that comprises a sequence which is expressed as RNA, e.g., mRNA or a regulatory RNA. In an embodiment, the exogenous nucleic acid sequence comprises a first chromosomal or extra-chromosomal exogenous nucleic acid sequence that modulates the conformation or expression of a second nucleic acid sequence the second nucleic acid sequence can be exogenous or endogenous. For example, an engineered cell can comprise an exogenous nucleic acid that controls the expression of an endogenous sequence. In an embodiment, the engineered cell comprises an exogenous nucleic acid sequence which comprises a codon optimized coding sequence for a polypeptide of interest and achieves higher expression of the polypeptide than a naturally-occurring coding sequence. The codon optimized coding sequence may be generated using a commercially available algorithm, e.g., GeneOptimizer (ThermoFisher Scientific), OptimumGene™ (GenScript, Piscataway, NJ USA), GeneGPS® (ATUM, Newark, CA USA), or Java Codon Adaptation Tool (JCat, www.jcat.de, Grote, A. et al., Nucleic Acids Research, Vol 33, Issue suppl 2, pp. W526-W531 (2005). In an embodiment, an engineered cell (e.g., engineered epithelial cell, e.g., engineered RPE cell, e.g., engineered ARPE-19 cell) is cultured from a monoclonal cell line. In some embodiments, the engineered cell is not an islet cell, as defined herein.

An "exogenous nucleic acid," as used herein, is a nucleic acid that does not occur naturally in a subject cell.

An "exogenous polypeptide," as used herein, is a polypeptide that is encoded by an exogenous nucleic acid in a subject cell. Reference to an amino acid position of a specific sequence means the position of said amino acid in a reference amino acid sequence, e.g., sequence of a full-length mature (after signal peptide cleavage) wild-type protein (unless otherwise stated), and does not exclude the presence of variations, e.g., deletions, insertions and/or substitutions at other positions in the reference amino acid sequence.

"Factor VII protein" or "FVII protein" as used herein, means a polypeptide that comprises the amino acid sequence of a naturally occurring factor VII protein or variant thereof that has a FVII biological activity, e.g., promoting blood clotting, as determined by an art-recognized assay, unless otherwise specified. Naturally occurring FVII exists as a single chain zymogen, a zymogen-like two-chain polypeptide and a fully activated two-chain form (FVIIa). In some embodiments, reference to FVII includes single-chain and two-chain forms thereof, including zymogen-like and FVIIa. FVII proteins that may be produced by a genetically modified cell described herein (e.g., derived from a human epithelial cell line, e.g., the ARPE-19 cell line), include wild-type primate (e.g., human), porcine, canine, and murine proteins, as well as variants of such wild-type proteins, including fragments, mutants, variants with one or more amino acid substitutions and/or deletions. In some embodiments, a variant FVII protein is capable of being activated to the fully activated two-chain form (Factor VIIa) that has at least 50%, 75%, 90% or more (including >100%) of the activity of wild-type Factor VIIa. Variants of FVII and FVIIa are known, e.g., marzeptacog alfa (activated) (MarzAA) and the variants described in European Patent No. 1373493, U.S. Pat. Nos. 7,771,996, 9,476,037 and US published application No. US20080058255.

Factor VII biological activity may be quantified by an art recognized assay, unless otherwise specified. For example, FVII biological activity in a sample of a biological fluid, e.g., plasma, may be quantified by (i) measuring the amount of Factor Xa produced in a system comprising tissue factor (TF) embedded in a lipid membrane and Factor X (Persson et al., *J. Biol. Chem.* 272:19919-19924, 1997); (ii) measuring Factor X hydrolysis in an aqueous system; (iii) measuring its physical binding to TF using an instrument based on surface plasmon resonance (Persson, *FEBS Letts.* 413:359-363, 1997); or (iv) measuring hydrolysis of a synthetic substrate; and/or (v) measuring generation of thrombin in a TF-independent in vitro system. In an embodiment, FVII activity is assessed by a commercially available chromogenic assay (BIOPHEN FVII, HYPHEN BioMed Neuville sur Oise, France), in which the biological sample containing FVII is mixed with thromboplastin calcium, Factor X and SXa-11 (a chromogenic substrate specific for Factor Xa.

"Factor VIII protein" or "FVIII protein" as used herein, means a polypeptide that comprises the amino acid sequence of a naturally occurring factor VIII polypeptide or variant thereof that has an FVIII biological activity, e.g., coagulation activity, as determined by an art-recognized assay, unless otherwise specified. FVIII proteins that may be expressed by a genetically modified cell described herein (e.g., derived from a human epithelial cell line, e.g., the ARPE-19 cell line), include wild-type primate (e.g., human), porcine, canine, and murine proteins, as well as variants of such wild-type proteins, including fragments, mutants, variants with one or more amino acid substitutions and/or deletions, B-domain deletion (BDD) variants, single chain variants and fusions of any of the foregoing wild-type or variants with a half-life extending polypeptide. In an embodiment, the cells are engineered to encode a precursor factor VIII polypeptide (e.g., with the signal sequence) with a full or partial deletion of the B domain. In an embodiment, the cells are engineered to encode a single chain factor VIII polypeptide which contains a variant FVIII protein preferably has at least 50%, 75%, 90% or more (including >100%) of the coagulation activity of the corresponding wild-type factor VIII. Assays for measuring the coagulation activity of FVIII proteins include the one stage or two stage coagulation assay (Rizza et al., 1982, Coagulation assay of FVIII:C and FIXa in Bloom ed. The Hemophelias. NY Churchill Livingston 1992) or the chromogenic substrate FVIII:C assay (Rosen, S. 1984. *Scand J Haematol* 33:139-145, suppl.).

A number of FVIII-BDD variants are known, and include, e.g., variants with the full or partial B-domain deletions disclosed in any of the following U.S. Pat. No. 4,868,112 (e.g., col. 2, line 2 to col. 19, line 21 and table 2); U.S. Pat. No. 5,112,950 (e.g., col. 2, lines 55-68, FIG. 2, and example 1); U.S. Pat. No. 5,171,844 (e.g., col. 4, line 22 to col. 5, line 36); U.S. Pat. No. 5,543,502 (e.g., col. 2, lines 17-46); U.S. Pat. Nos. 5,595,886; 5,610,278; 5,789,203 (e.g., col. 2, lines 26-51 and examples 5-8); U.S. Pat. No. 5,972,885 (e.g., col. 1, lines 25 to col. 2, line 40); 6,048,720 (e.g., col. 6, lines 1-22 and example 1); U.S. Pat. Nos. 6,060,447; 6,228,620; 6,316,226 (e.g., col. 4, line 4 to col. 5, line 28 and examples 1-5); U.S. Pat. Nos. 6,346,513; 6,458,563 (e.g., col. 4, lines 25-53) and U.S. Pat. No. 7,041,635 (e.g., col. 2, line 1 to col. 3, line 19, col. 3, line 40 to col. 4, line 67, col. 7, line 43 to col. 8, line 26, and col. 11, line 5 to col. 13, line 39).

In some embodiments, a FVIII-BDD protein produced by a genetically modified cell described herein (e.g., derived from a human epithelial cell line, e.g., the ARPE-19 cell line) has one or more of the following deletions of amino acids in the B-domain: (i) most of the B domain except for amino-terminal B-domain sequences essential for intracellular processing of the primary translation product into two polypeptide chains (WO 91/09122); (ii) a deletion of amino acids 747-1638 (Hoeben R. C., et al. *J. Biol. Chem.* 265 (13): 7318-7323 (1990)); amino acids 771-1666 or amino acids 868-1562 (Meulien P., et al. *Protein Eng.* 2(4):301-6 (1988); amino acids 982-1562 or 760-1639 (Toole et al., *Proc. Natl. Acad. Sci. U.S.A.* 83:5939-5942 (1986)); amino acids 797-1562 (Eaton et al., *Biochemistry* 25:8343-8347 (1986)); 741-1646 (Kaufman, WO 87/04187)), 747-1560 (Sarver et al., DNA 6:553-564 (1987)); amino acids 741-1648 (Pasek, WO 88/00831)), amino acids 816-1598 or 741-1689 (Lagner (Behring Inst. Mitt. (1988) No 82:16-25, EP 295597); a deletion that includes one or more residues in a furin protease recognition sequence, including any of the specific deletions recited in U.S. Pat. No. 9,956,269 at col. 10, line 65 to col. 11, line 36.

In other embodiments, a FVIII-BDD protein retains any of the following B-domain amino acids or amino acid sequences: (i) one or more N-linked glycosylation sites in the B-domain, e.g., residues 757, 784, 828, 900, 963, or optionally 943, first 226 amino acids or first 163 amino acids (Miao, H. Z., et al., *Blood* 103(a): 3412-3419 (2004), Kasuda, A., et al., *J. Thromb. Haemost.* 6: 1352-1359 (2008), and Pipe, S. W., et al., *J. Thromb. Haemost.* 9: 2235-2242 (2011).

In some embodiments, the FVIII-BDD protein is a single-chain variant generated by substitution or deletion of one or more amino acids in the furin protease recognition sequence LKRHQR at amino acids 768-773 in SEQ ID NO:8 that prevents proteolytic cleavage at this site, including any of the substitutions at the R1645 and/or R1648 positions described in U.S. Pat. Nos. 10,023,628, 9,394,353 and 9,670,267.

In some embodiments, any of the above FVIII-BDD proteins may further comprise one or more of the following variations: a F3095 substitution to improve expression of the FVIII-BDD protein (Miao, H. Z., et al., Blood 103(a): 3412-3419 (2004); albumin fusions (WO 2011/020866); and Fc fusions (WO 04/101740).

All FVIII-BDD amino acid positions referenced herein refer to the positions in full-length human FVIII, unless otherwise specified.

"Factor IX protein" or "FIX protein", as used herein, means a polypeptide that comprises the amino acid sequence of a naturally occurring factor IX protein or variant thereof that has a FIX biological activity, e.g., coagulation activity, as determined by an art-recognized assay, unless otherwise specified. FIX is produced as an inactive zymogen, which is converted to an active form by factor XIa excision of the activation peptide to produce a heavy chain and a light chain held together by one or more disulfide bonds. FIX proteins that may be produced by a genetically modified described herein (e.g., derived from an RPE cell line, e.g., the ARPE-19 cell line), include wild-type primate (e.g., human), porcine, canine, and murine proteins, as well as variants of such wild-type proteins, including fragments, mutants, variants with one or more amino acid substitutions and/or deletions and fusions of any of the foregoing wild-type or variant proteins with a half-life extending polypeptide. In an embodiment, cells are engineered to encode a full-length wild-type human factor IX polypeptide (e.g., with the signal sequence) or a functional variant thereof. A variant FIX protein preferably has at least 50%, 75%, 90% or more (including >100%) of the coagulation activity of wild-type factor VIX. Assays for measuring the coagulation activity of FIX proteins include the Biophen Factor IX assay (Hyphen BioMed) and the one stage clotting assay (activated partial thromboplastin time (aPTT), e.g., as described in EP 2 032 607, thrombin generation time assay (TGA) and rotational thromboelastometry, e.g., as described in WO 2012/006624.

A number of functional FIX variants are known and may be expressed by engineered cells encapsulated in a device described herein, including any of the functional FIX variants described in the following international patent publications: WO 02/040544 at page 4, lines 9-30 and page 15, lines 6-31; WO 03/020764 in Tables 2 and 3 at pages 14-24, and at page 12, lines 1-27; WO 2007/149406 at page 4, line 1 to page 19, line 11; WO 2007/149406 A2 at page 19, line 12 to page 20, line 9; WO 08/118507 at page 5, line 14 to page 6, line 5; WO 09/051717 at page 9, line 11 to page 20, line 2; WO 09/137254 at page 2, paragraph [006] to page 5, paragraph [011] and page 16, paragraph [044] to page 24, paragraph [057]; WO 09/130198 A2 at page 4, line 26 to page 12, line 6; WO 09/140015 at page 11, paragraph [0043] to page 13, paragraph [0053]; WO 2012/006624; WO 2015/086406.

In certain embodiments, the FIX polypeptide comprises a wild-type or variant sequence fused to a heterologous polypeptide or non-polypeptide moiety extending the half-life of the FIX protein. Exemplary half-life extending moieties include Fc, albumin, a PAS sequence, transferrin, CTP (28 amino acid C-terminal peptide (CTP) of human chorionic gonadotropin (hCG) with its 4 O-glycans), polyethylene glycol (PEG), hydroxyethyl starch (HES), albumin binding polypeptide, albumin-binding small molecules, or any combination thereof. An exemplary FIX polypeptide is the rFIXFc protein described in WO 2012/006624, which is an FIXFc single chain (FIXFc-sc) and an Fc single chain (Fc-sc) bound together through two disulfide bonds in the hinge region of Fc.

FIX variants also include gain and loss of function variants. An example of a gain of function variant is the "Padua" variant of human FIX, which has a L (leucine) at position 338 of the mature protein instead of an R (arginine) (corresponding to amino acid position 384 of SEQ ID NO:16), and has greater catalytic and coagulant activity compared to wild-type human FIX (Chang et al., J. Biol. Chem., 273:12089-94 (1998)). An example of a loss of function variant is an alanine substituted for lysine in the fifth amino acid position from the beginning of the mature protein, which results in a protein with reduced binding to collagen IV (e.g., loss of function).

"Islet cell", as used herein, means a cell that comprises any naturally occurring or any synthetically created, or modified, cell that is intended to recapitulate, mimic or otherwise express, in part or in whole, the functions, in part or in whole, of the cells of the pancreatic islets of Langerhans. The term "islet cell" includes a glucose-responsive, insulin producing cell derived from a stem cell, e.g., from an induced pluripotent stem cell line.

"Polymer composition", as used herein, is a composition (e.g., a solution, mixture) comprising one or more polymers. As a class, "polymers' includes homopolymers, heteropolymers, co-polymers, block polymers, block co-polymers and can be both natural and synthetic. Homopolymers contain one type of building block, or monomer, whereas co-polymers contain more than one type of monomer.

"Polypeptide", as used herein, refers to a polymer comprising amino acid residues linked through peptide bonds and having at least two, and in some embodiments, at least 3, 4, 5, 10, 50, 75,100, 150 or 200 amino acid residues.

"Prevention," "prevent," and "preventing" as used herein refers to a treatment that comprises administering a composition (or preparation) of devices encapsulating genetically modified cells that express an exogenous polypeptide, prior to the onset of one or more symptoms of a disease or condition that is amenable to treatment with the exogenous polypeptide, to preclude the physical manifestation of the symptom(s). In some embodiments, "prevention," "prevent," and "preventing" require that signs or symptoms of a disease or condition have not yet developed or have not yet been observed.

"RPE cell" as used herein refers to a cell having one or more of the following characteristics: a) it comprises a retinal pigment epithelial cell (RPE) (e.g., cultured using an RPE cell line, e.g., the ARPE-19 cell line (ATCC® CRL-2302™)) or a cell derived or engineered therefrom, e.g., by stably transfecting cells cultured from the ARPE-19 cell line with an exogenous sequence that encodes a polypeptide of interest or inserting the exogenous sequence into one of the specific OCR insertion sites described herein, a cell derived from a primary cell culture of RPE cells, a cell isolated directly (without long term culturing, e.g., less than 5 or 10 passages or rounds of cell division since isolation) from naturally occurring RPE cells, e.g., from a human or other mammal, a cell derived from a transformed, an immortalized, or a long term (e.g., more than 5 or 10 passages or rounds of cell division) RPE cell culture; b) a cell that has been obtained from a less differentiated cell, e.g., a cell developed, programmed, or reprogramed (e.g., in vitro) into an RPE cell or a cell that is, except for any genetic engineering, substantially similar to one or more of a naturally occurring RPE cell or a cell from a primary or long term culture of RPE cells (e.g., the cell can be derived from an IPS cell); or c) a cell that has one or more of the following properties: i) it expresses one or more of the biomarkers CRALBP, RPE-65, RLBP, BEST1, or αB-crystallin; ii) it does not express one or more of the biomarkers CRALBP, RPE-65, RLBP, BEST1, or αB-crystallin; iii) it is naturally found in the retina and forms a monolayer above the choroidal blood vessels in the Bruch's membrane; or iv) it is responsible for epithelial transport, light absorption, secretion, and immune modulation in the retina; or v) it has been created synthetically, or modified from a naturally occurring cell, to have the same or substantially the same genetic content, and optionally the same or substantially the same epigenetic content, as an immortalized RPE cell line (e.g., the ARPE-19 cell line (ATCC® CRL-2302™)). Other exemplary strains of RPE cells include ARPE-19-SEAP-2-neo cells, RPE-J cells, and hTERT RPE-1 cells. In an embodiment, an RPE described herein is engineered, e.g., to have a new property, e.g., the cell is genetically modified by inserting at least one exogenous transcription unit into one or more of the OCR locations described herein. In other embodiments, an RPE cell is not engineered.

"Sequence identity" or "percent identical", when used herein to refer to two nucleotide sequences or two amino acid sequences, means the two sequences are the same within a specified region, or have the same nucleotides or amino acids at a specified percentage of nucleotide or amino acid positions within the specified when the two sequences are compared and aligned for maximum correspondence over a comparison window or designated region. Sequence identity may be determined using standard techniques known in the art including, but not limited to, any of the algorithms described in US Patent Application Publication No. 2017/02334455 A1. In an embodiment, the specified percentage of identical nucleotide or amino acid positions is at least about 80%, 85%, 90%, 91%, 92%, 93%, 94%, 95%, 96%, 97%, 98%, 99% or higher.

"Spherical" as used herein, mean a device (e.g., a hydrogel capsule or other particle) having a curved surface that forms a sphere (e.g., a completely round ball) or sphere-like shape, which may have waves and undulations, e.g., on the surface. Spheres and sphere-like objects can be mathematically defined by rotation of circles, ellipses, or a combination around each of the three perpendicular axes, a, b, and c. For a sphere, the three axes are the same length. Generally, a sphere-like shape is an ellipsoid (for its averaged surface) with semi-principal axes within 10%, or 5%, or 2.5% of each other. The diameter of a sphere or sphere-like shape is the average diameter, such as the average of the semi-principal axes.

"Spheroid", as that term is used herein to refer to a device (e.g., a hydrogel capsule or other particle), means the device has (i) a perfect or classical oblate spheroid or prolate spheroid shape or (ii) has a surface that roughly forms a spheroid, e.g., may have waves and undulations and/or may be an ellipsoid (for its averaged surface) with semi-principal axes within 100% of each other.

"Subject" as used herein refers to a human or non-human animal. In an embodiment, the subject is a human (i.e., a male or female) of any age group, e.g., a pediatric human subject (e.g., infant, child, adolescent) or adult human subject (e.g., young adult, middle-aged adult, or senior adult)). In an embodiment, the subject is a non-human animal, for example, a mammal (e.g., a mouse, a dog, a primate (e.g., a cynomolgus monkey or a rhesus monkey). In an embodiment, the subject is a commercially relevant mammal (e.g., cattle, pig, horse, sheep, goat, cat, or dog) or a bird (e.g., a commercially relevant bird such as a chicken, duck, goose, or turkey). In certain embodiments, the animal is a mammal. The animal may be a male or female and at any stage of development. A non-human animal may be a transgenic animal.

"Transcription unit" means a DNA sequence, e.g., present in an exogenous nucleic acid, that comprises at least a promoter sequence operably linked to a coding sequence, and may also comprise one or more additional elements that control or enhance transcription of the coding sequence into RNA molecules or translation of the RNA molecules into polypeptide molecules in some embodiments, a transcription unit also comprises a polyadenylation (polyA) signal sequence and poly A site. In an embodiment, a transcription unit is present as an exogenous sequence integrated in one or more of the specific OCR insertion locations described herein.

"Treatment," "treat," and "treating" as used herein refers to one or more of reducing, reversing, alleviating, delaying the onset of, or inhibiting the progress of one or more of a symptom, manifestation, or underlying cause, of a disease (e.g., hemophilia A). In an embodiment, treating comprises reducing, reversing, alleviating, delaying the onset of, or inhibiting the progress of a symptom or condition associated with the disease. In an embodiment, treating comprises increasing levels of a therapeutic polypeptide in at least one tissue of a subject in need thereof, e.g., in one or more of plasma, liver, kidney and heart. In some embodiments, "treatment," "treat," and "treating" require that signs or symptoms associated with the disease or condition have developed or have been observed. In other embodiments, treatment may be administered in the absence of signs or symptoms of the disease or condition, e.g., in preventive treatment. For example, treatment may be administered to a susceptible individual prior to the onset of symptoms (e.g., due to a history of symptoms and/or genetic or other susceptibility factors). Treatment may also be continued after symptoms have resolved, for example, to delay or prevent recurrence. In some embodiments, treatment comprises prevention and in other embodiments it does not.

Selected Chemical Definitions

Definitions of specific functional groups and chemical terms are described in more detail below. The chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry,* $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* $3^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

When a range of values is listed, it is intended to encompass each value and sub-range within the range. For example, "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

As used herein, "alkyl" refers to a radical of a straight-chain or branched saturated hydrocarbon group having from 1 to 24 carbon atoms ("$C_1$-$C_{24}$ alkyl"). In some embodiments, an alkyl group has 1 to 12 carbon atoms ("$C_1$-$C_{12}$ alkyl"), 1 to 10 carbon atoms ("$C_1$-$C_{10}$ alkyl"), 1 to 8 carbon atoms ("$C_1$-$C_8$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). In some embodiments, an alkyl group has 2 to 6 carbon atoms ("$C_2$-$C_6$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent.

As used herein, "alkenyl" refers to a radical of a straight-chain or branched hydrocarbon group having from 2 to 24 carbon atoms, one or more carbon-carbon double bonds, and no triple bonds ("$C_2$-$C_{24}$ alkenyl"). In some embodiments, an alkenyl group has 2 to 12 carbon atoms ("$C_2$-$C_{12}$ alkenyl"), 2 to 10 carbon atoms ("$C_2$-$C_{10}$ alkenyl"), 2 to 8 carbon atoms ("$C_2$-$C_8$ alkenyl"), 2 to 6 carbon atoms ("$C_2$-$C_6$ alkenyl"), 2 to 5 carbon atoms ("$C_2$-$C_5$ alkenyl"), 2 to 4 carbon atoms ("$C_2$-$C_4$ alkenyl"), 2 to 3 carbon atoms ("$C_2$-$C_3$ alkenyl"), or 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_2$-4 alkenyl groups as well as pentenyl ($C_5$), pentadienyl ($C_5$), hexenyl ($C_6$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent.

As used herein, the term "alkynyl" refers to a radical of a straight-chain or branched hydrocarbon group having from 2 to 24 carbon atoms, one or more carbon-carbon triple bonds ("$C_2$-$C_{24}$ alkenyl"). In some embodiments, an alkynyl group has 2 to 12 carbon atoms ("$C_2$-$C_{12}$ alkynyl"), 2 to 10 carbon atoms ("$C_2$-$C_{10}$ alkynyl"), 2 to 8 carbon atoms ("$C_2$-$C_8$ alkynyl"), 2 to 6 carbon atoms ("$C_2$-$C_6$ alkynyl"), 2 to 5 carbon atoms ("$C_2$-$C_5$ alkynyl"), 2 to 4 carbon atoms ("$C_2$-$C_4$ alkynyl"), 2 to 3 carbon atoms ("$C_2$-$C_3$ alkynyl"), or 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include ethynyl ($C_2$), 1-propynyl ($C_3$), 2-propynyl ($C_3$), 1-butynyl ($C_4$), 2-butynyl ($C_4$), and the like. Each instance of an alkynyl group may be independently optionally substituted, i.e., unsubstituted (an "unsubstituted alkynyl") or substituted (a "substituted alkynyl") with one or more substituents e.g., for instance from 1 to 5 substituents, 1 to 3 substituents, or 1 substituent.

As used herein, the term "heteroalkyl," refers to a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any position of the heteroalkyl group. Exemplary heteroalkyl groups include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—$ $S(O)_2—CH_3$, $—CH=CH—O—CH_3$, $—Si(CH_3)_3$, $—CH_2—CH=N—OCH_3$, $—CH=CH—N(CH_3)—CH_3$, $—O—CH_3$, and $—O—CH_2—CH_3$. Up to two or three heteroatoms may be consecutive, such as, for example, $—CH_2—NH—OCH_3$ and $—CH_2—O—Si(CH_3)_3$. Where "heteroalkyl" is recited, followed by recitations of specific heteroalkyl groups, such as $—CH_2O$, $—NR^CR^D$, or the like, it will be understood that the terms heteroalkyl and $—CH_2O$ or $—NR^CR^D$ are not redundant or mutually exclusive. Rather, the specific heteroalkyl groups are recited to add clarity. Thus, the term "heteroalkyl" should not be interpreted herein as excluding specific heteroalkyl groups, such as $—CH_2O$, $—NR^CR^D$, or the like. Each instance of a heteroalkyl group may be independently optionally substituted, i.e., unsubstituted (an "unsubstituted heteroalkyl") or substituted (a "substituted heteroalkyl") with one or more substituents e.g., for instance from 1 to 5 substituents, 1 to 3 substituents, or 1 substituent.

The terms "alkylene," "alkenylene," "alkynylene," or "heteroalkylene," alone or as part of another substituent, mean, unless otherwise stated, a divalent radical derived from an alkyl, alkenyl, alkynyl, or heteroalkyl, respectively. An alkylene, alkenylene, alkynylene, or heteroalkylene group may be described as, e.g., a $C_1$-$C_6$-membered alkylene, $C_2$-$C_6$-membered alkenylene, $C_1$-$C_6$-membered alkynylene, or $C_1$-$C_6$-membered heteroalkylene, wherein the term "membered" refers to the non-hydrogen atoms within the moiety. In the case of heteroalkylene groups, heteroatoms can also occupy either or both chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ may represent both $—C(O)_2R'$- and $—R'C(O)_2—$.

As used herein, "aryl" refers to a radical of a monocyclic or polycyclic (e.g., bicyclic or tricyclic) 4n+2 aromatic ring system (e.g., having 6, 10, or 14 $\pi$ electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents.

As used herein, "heteroaryl" refers to a radical of a 5-10 membered monocyclic or bicyclic 4n+2 aromatic ring system (e.g., having 6 or 10 $\pi$ electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Other exemplary heteroaryl groups include heme and heme derivatives.

As used herein, the terms "arylene" and "heteroarylene," alone or as part of another substituent, mean a divalent radical derived from an aryl and heteroaryl, respectively.

As used herein, "cycloalkyl" refers to a radical of a non-aromatic cyclic hydrocarbon group having from 3 to 10 ring carbon atoms ("$C_3$-$C_{10}$ cycloalkyl") and zero heteroatoms in the non–aromatic ring system. In some embodiments, a cycloalkyl group has 3 to 8 ring carbon atoms ("$C_3$-$C_8$cycloalkyl"), 3 to 6 ring carbon atoms ("$C_3$-$C_6$ cycloalkyl"), or 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_3$-$C_8$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_5$), bicyclo[2.2.2]octanyl ($C_8$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro [4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents.

"Heterocyclyl" as used herein refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, aziridinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, piperazinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl or thiomorpholinyl-1,1-dioxide. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a6,6-bicyclic heterocyclic ring) include, without limitation, tetrahydroquinolinyl, tetrahydroisoquinolinyl, and the like.

"Amino" as used herein refers to the radical —$NR^{70}R^{71}$, wherein $R^{70}$ and $R^{71}$ are each independently hydrogen, $C_1$-$C_8$ alkyl, $C_3$-$C_{10}$ cycloalkyl, $C_4$-$C_{10}$ heterocyclyl, $C_6$-$C_{10}$ aryl, and $C_5$-$C_{10}$ heteroaryl. In some embodiments, amino refers to $NH_2$.

As used herein, "cyano" refers to the radical —CN.

As used herein, "halo" or "halogen," independently or as part of another substituent, mean, unless otherwise stated, a fluorine (F), chlorine ($C_1$), bromine (Br), or iodine (I) atom.

As used herein, "hydroxy" refers to the radical —OH.

Alkyl, alkenyl, alkynyl, heteroalkyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present disclosure contemplates any and all such combinations to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Compounds of Formula (I) described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

Compounds of Formula (I) described herein may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, and $^{14}C$; O may be in any isotopic form, including $^{16}O$ and $^{18}O$; and the like.

The term "pharmaceutically acceptable salt" is meant to include salts of the active compounds that are prepared with relatively nontoxic acids or bases, depending on the particular substituents found on the compounds described herein. When compounds of Formula (I) used to prepare devices of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds used in the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, e.g., Berge et al, *Journal of Pharmaceutical Science* 66: 1-19 (1977)). Certain specific compounds used in the devices of the present disclosure (e.g., a particle, a hydrogel capsule) contain both basic and acidic functionalities that allow the compounds to be converted into either base or acid addition salts. These salts may be prepared by methods known to those skilled in the art. Other pharmaceutically acceptable carriers known to those of skill in the art are suitable for use in the present disclosure.

Devices of the present disclosure may contain a compound of Formula (I) in a prodrug form. Prodrugs are those compounds that readily undergo chemical changes under physiological conditions to provide the compounds useful to mitigate the FBR to devices of the present disclosure. Additionally, prodrugs can be converted to useful compounds of Formula (I) by chemical or biochemical methods in an ex vivo environment.

Certain compounds of Formula (I) described herein can exist in unsolvated forms as well as solvated forms, including hydrated forms. In general, the solvated forms are equivalent to unsolvated forms and are encompassed within the scope of the present disclosure. Certain compounds of Formula (I) described herein may exist in multiple crystalline or amorphous forms. In general, all physical forms are equivalent for the uses contemplated by the present disclosure and are intended to be within the scope of the present disclosure.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound and wherein x is a number greater than 0.

The term "tautomer" as used herein refers to compounds that are interchangeable forms of a compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Tautomeric forms may be relevant to the attainment of the optimal chemical reactivity and biological activity of a compound of interest.

The symbol "〰" as used herein refers to a connection to an entity, e.g., a polymer (e.g., hydrogel-forming polymer such as alginate) or surface of an implantable element (e.g., a particle, device (e.g., a hydrogel capsule) or material). The connection represented by "〰" may refer to direct attachment to the entity, e.g., a polymer or an implantable element (e.g., a device), or may refer to linkage to the entity through an attachment group. An "attachment group," as described herein, refers to a moiety for linkage of a compound of Formula (I) to an entity (e.g., a polymer or an implantable element as described herein), and may comprise any attachment chemistry known in the art. A listing of exemplary attachment groups is outlined in *Bioconjugate Techniques* ($3^{rd}$ ed, Greg T. Hermanson, Waltham, MA: Elsevier, Inc, 2013), which is incorporated herein by reference in its entirety. In some embodiments, an attachment group comprises alkyl, alkenyl, alkynyl, heteroalkyl, cycloalkyl, heterocyclyl, aryl, heteroaryl, —C(O)—, —OC(O)—, —N($R^C$)C(O)—, —C(O)N($R^C$)—, —N($R^C$)N($R^D$)—, —NCN—, —C(=N($R^C$)($R^D$))O—, —S—, —$S(O)_x$—, —$OS(O)_x$—, —N($R^C$)$S(O)_x$—, —$S(O)_x$N($R^C$)—, —$P(R^F)_y$—, —$Si(OR^A)_2$—,—Si($R^G$)($OR^A$)—, —B($OR^A$)—, or a metal, wherein each of $R^A$, $R^C$, $R^D$, $R^F$, $R^G$, x and y is independently as described herein. In some embodiments, an attachment group comprises an amine, ketone, ester, amide, alkyl, alkenyl, alkynyl, or thiol. In some embodiments, an attachment group is a cross-linker. In some embodiments, the attachment group is —C(O)($C_1$-$C_6$-alkylene)-, wherein alkylene is substituted with $R^1$, and $R^1$ is as described herein. In some embodiments, the attachment group is —C(O)($C_1$-$C_6$-alkylene)-, wherein alkylene is substituted with 1-2 alkyl groups (e.g., 1-2 methyl groups). In some embodiments, the attachment group is —$C(O)C(CH_3)_2$—. In some embodiments, the attachment group is —C(O)(methylene)-, wherein alkylene is substituted with 1-2 alkyl groups (e.g., 1-2 methyl groups). In some embodiments, the attachment group is —$C(O)CH(CH_3)$—. In some embodiments, the attachment group is —$C(O)C(CH_3)$—.

OCR Insertion Sites and Exogenous Transcription Units

The genetically modified cells (e.g., genetically modified human RPE cells) of the present disclosure comprises at least one exogenous transcription unit stably integrated into one or more of four target OCRs in the genome: an OCR on Chr 2, an OCR on Chr 5, an OCR on Chr 8, and an OCR on Chr 12. The 5' and 3' boundaries of a target OCR may be defined in relation to: (i) a human reference genome sequence assembly, e.g., the GRCh37 assembly (also known as hg19) or the GRCh38. p13 assembly (also known as hg38) in Ensembl, which assemblies are based at the European Molecular Biology Laboratory's European Bioinformatics Institute (EMBI-EBI) (Cambridge, United Kingdom) (available at the following Ensembl webpages: grch 37.ensembl.org and useast.ensembl.org/Homo_sapiens/Info/Index) and/or (ii) the OCR nucleotide sequence recited in SEQ ID NO:1 (for the Chr 2 OCR), SEQ ID NO:2 (for the Chr 5 OCR), SEQ ID NO:26 (for the Chr 8 OCR) or SEQ ID NO:3 (for the Chr 12 OCR).

In an embodiment, the exogenous transcription unit is inserted in the target genomic OCR(s) of the genetically modified cell anywhere between the two nucleotide positions that define the 5' and 3' boundaries of the target OCR(s), e.g., between two nucleotide positions that correspond to the first and last nucleotides of SEQ ID NO:1, SEQ ID NO:2, SEQ ID NO:26, or SEQ ID NO:3. In an embodiment, the corresponding nucleotide positions in a target OCR or insertion site are in a nucleotide sequence that shares at least 90% sequence identity with SEQ ID NO:1, SEQ ID NO:2, SEQ ID NO:26 or SEQ ID NO:3. In an embodiment, the shared sequence identity of a target OCR in the cell line and the corresponding Chr 2 OCR sequence, Chr 5 OCR sequence, Chr 8 OCR sequence or Chr 12 OCR sequence recited herein is 91%, 92%, 93%, 94%, 95%, 96%, 97%, 98%, 99% or greater. These sequences may be used in combination with a targeted genome editing technique to insert the transcription unit into a human cell, e.g., an epithelial cell, at a desired site(s) in the target OCR(s), e.g., on Chr 2, Chr 5, Chr 8 and/or Chr 12. The targeted genome editing technique may be any technique known in the art, e.g., techniques that employ site directed nucleases such as CRISPR-Cas, zinc finger nucleases, transcription activator-like effector nucleases (TALENs), and meganucleases, In some embodiments, an insertion site for the transcription unit on Chr 2 is located between two nucleotide positions corresponding to positions $x_1$ and $y_1$ in SEQ ID NO:1, wherein $x_1$ and $y_1$ are selected from the group consisting of: 10 and 1200; 25 and 900; 50 and 600; 100 and 300; 200 and 250 and 211 and 218. In an embodiment, an insertion site on Chr 2 is located between two nucleotide positions corresponding to positions 100,817,368 and 100,817,374 in the hg19 sequence for Chr 2.

In some embodiments, an insertion site for the transcription unit on Chr 5 is located between two nucleotide positions corresponding to positions $x_2$ and $y_2$ in SEQ ID NO:2, wherein $x_2$ and $y_2$ are selected from the group consisting of: 10 and 1100; 20 and 800; 30 and 500; 40 and 200; 50 and 100; and 59 and 60. In an embodiment, an insertion site on Chr 5 is located between two nucleotide positions corresponding to positions 53,853,740 and 53,853,741 in the hg19 sequence for Chr 5.

In some embodiments, an insertion site for the transcription unit on Chr 12 is located between two nucleotide positions corresponding to positions $x_3$ and $y_3$ in SEQ ID NO:3, wherein $x_3$ and $y_3$ are selected from the group consisting of: 50 and 1200; 100 and 1000; 200 and 800; 400 and 600; 500 and 550; and 518 and 525. In an embodiment, an insertion site on Chr 5 is located between two nucleotide positions corresponding to positions 122,186,872 and 122,186,877 in the hg19 sequence for Chr 12.

In some embodiments, an insertion site for the transcription unit on Chr 8 is located between two nucleotide positions corresponding to positions $x_4$ and $y_4$ in SEQ ID NO:26, wherein $x_4$ and $y_4$ are selected from the group consisting of: 50 and 950; 150 and 850; 300 and 700; 400 and 600; 425 and 475; and 440 and 445. In an embodiment, an insertion site on Chr 8 is located between two nucleotide positions corresponding to positions 30,105,939 and 30,105,944 in the human hg38 reference genome sequence for Chr 8.

In an embodiment, an exogenous transcription unit is inserted into one, two, three or all four of the target OCRs on Chr 2, Chr 5, Chr 8 and Chr 12 of the genetically modified cell. The transcription unit in each insertion site may encode the same or different substance, e.g., a polypeptide. Two or more transcription units may be inserted in tandem at a single site in a target OCR, and may encode the same or different substances. In an embodiment, the promoter in the upstream transcription unit is different than the promoter in the downstream transcription unit. In an embodiment, the two transcription units are identical with each other except for the promoter.

The promoter sequence in each inserted transcription unit may be for any promoter capable of driving expression of a coding sequence operably linked to the promoter in the genetically modified cell. In an embodiment, the promoter sequence consists essentially of, or consists of, SEQ ID NO:4 or a nucleotide sequence that is substantially identical to SEQ ID NO:4, e.g., is at least 95%, 96%, 97%, 98%, 99% or more identical to SEQ ID NO:4. In an embodiment, the promoter consists of SEQ ID NO:4. In an embodiment, the promoter sequence consists essentially of, or consists of, SEQ ID NO:5 or a nucleotide sequence that is substantially identical to SEQ ID NO:5, e.g., is at least 95%, 96%, 97%, 98%, 99% or more identical to SEQ ID NO:5. In an embodiment, the promoter consists of SEQ ID NO:5.

In an embodiment, the genetically modified cell comprises two transcription units inserted in tandem in at least one of the target OCRs described herein. In an embodiment, the promoter sequence in the upstream transcription unit comprises SEQ ID NO:4 or a nucleotide sequence that is substantially identical to SEQ ID NO:4, e.g., is at least 95%, 96%, 97%, 98%, 99% or more identical to SEQ ID NO:4. In an embodiment, the promoter sequence in the upstream transcription unit comprises SEQ ID NO:5 or a nucleotide sequence that is substantially identical to SEQ ID NO:5, e.g., is at least 95%, 96%, 97%, 98%, 99% or more identical to SEQ ID NO:5. In an embodiment, the promoter sequences recited in the previous sentence are reversed, such that the upstream transcription unit comprises SEQ ID NO:5 or the substantially similar nucleotide sequence and the downstream transcription unit comprises SEQ ID NO:5 or the substantially similar nucleotide sequence.

The coding sequence in each inserted transcription unit may be operably linked to a polyA signal sequence, which sequence may be the same or different in each transcription unit. In an embodiment, the polyA signal sequence consists essentially of, or consists of, SEQ ID NO:6 or a nucleotide sequence that is substantially identical to SEQ ID NO:6, e.g., is at least 95%, 96%, 97%, 98%, 99% or more identical to SEQ ID NO:6. In an embodiment, the polyA signal sequence consists of SEQ ID NO:6.

In some embodiments, the exogenous transcription unit encodes a therapeutic polypeptide (e.g., a protein), such as a clotting factor, growth factor, hormone, enzyme, cytokine (e.g., a pro-inflammatory cytokine or an anti-inflammatory cytokine), cytokine receptor, chimeric protein, fusion protein or lipoprotein. The polypeptide encoded by the exogenous transcription unit may have a naturally occurring amino acid sequence or may contain a variant of the naturally occurring sequence. The variant can be a non-naturally occurring or naturally occurring amino acid substitution, mutation, deletion or addition relative to the reference (e.g., naturally occurring) sequence. The naturally occurring amino acid sequence may be a polymorphic variant. The naturally occurring amino acid sequence can be a human or a non-human amino acid sequence. In some embodiments, the naturally occurring amino acid sequence is a human sequence. In some embodiments, the therapeutic polypeptide has about 2, 3, 4, 5, 6, 7, 8, 9, 10, 12, 14, 16, 18, 20, 25, 30, 35, 40, 45, or less than 50 amino acids. In some embodiments, the polypeptide has an average molecular weight of 5 kD, 10 kD, 25 kD, 50 kD, 100 kD, 150 kD, 200 kD, 250 kD, 500 kD, or more.

In some embodiments, the polypeptide is a hormone. Exemplary hormones include anti-diuretic hormone (ADH), oxytocin, growth hormone (GH), prolactin, growth hormone-releasing hormone (GHRH), thyroid stimulating hormone (TSH), thyrotropin-release hormone (TRH), adrenocorticotropic hormone (ACTH), follicle-stimulating hormone (FSH), luteinizing hormone (LH), luteinizing hormone-releasing hormone (LHRH), thyroxine, calcitonin, parathyroid hormone (PTH), aldosterone, cortisol, epinephrine, glucagon, insulin, estrogen, progesterone, and testosterone. In some embodiments, the polypeptide is insulin (e.g., insulin A-chain, insulin B-chain, or proinsulin). In some embodiments, the polypeptide is a growth hormone, such as human growth hormone (hGH), recombinant human growth hormone (rhGH), bovine growth hormone, methionine-human growth hormone, des-phenylalanine human growth hormone, and porcine growth hormone.

In some embodiments, the polypeptide is a growth factor, e.g., vascular endothelial growth factor (VEGF), nerve growth factor (NGF), platelet-derived growth factor (PDGF), fibroblast growth factor (FGF), epidermal growth factor (EGF), transforming growth factor (TGF), and insulin-like growth factor-I and -II (IGF-I and IGF-II).

In some embodiments, the polypeptide is a clotting factor or a coagulation factor, e.g., a blood clotting factor or a blood coagulation factor. In some embodiments, the polypeptide is involved in coagulation, i.e., the process by which blood is converted from a liquid to solid or gel. Exemplary clotting factors and coagulation factors include Factor I (e.g., fibrinogen), Factor II (e.g., prothrombin), Factor III (e.g., tissue factor), Factor V (e.g., proaccelerin, labile factor), Factor VI, Factor VII (e.g., stable factor, proconvertin), Factor VIII (e.g., antihemophilic factor A), Factor VIIIC, Factor IX (e.g., antihemophilic factor B), Factor X (e.g., Stuart-Prower factor), Factor XI (e.g., plasma thromboplastin antecedent), Factor XII (e.g., Hagerman factor), Factor XIII (e.g., fibrin-stabilizing factor), von Willebrand factor (vWF), prekallikrein, heparin cofactor II, high molecular weight kininogen (e.g., Fitzgerald factor), antithrombin III, and fibronectin. In some embodiments, the polypeptide is an anti-clotting factor, such as Protein C.

In some embodiments, the polypeptide is an immunoglobulin chain (heavy or light chain) or fragment thereof, comprising at least one immunoglobulin variable domain sequence, and optionally comprising an immunoglobulin Fc region. In an embodiment, the polypeptide a full-length immunoglobulin chain.

In some embodiments, the polypeptide is a cytokine or a cytokine receptor, or a chimeric protein including cytokines or their receptors, including, for example tumor necrosis factor alpha and beta, their receptors and their derivatives, renin; lipoproteins; colchicine; corticotrophin; vasopressin; somatostatin; lypressin; pancreozymin; leuprolide; alpha-1-antitrypsin; atrial natriuretic factor; lung surfactant; a plasminogen activator other than a tissue-type plasminogen activator (t-PA), for example a urokinase; bombesin; thrombin; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; chorionic gonadotropin; a microbial protein, such as beta-lactamase; DNase; inhibin; activin; receptors for hormones or growth factors; integrin; protein A or D; rheumatoid factors; platelet-derived growth factor (PDGF); epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; an interferon such as interferon-alpha (e.g., interferon.alpha.2A), -beta, -gamma, -lambda and consensus interferon; colony stimulating factors (CSFs), e.g., M-CSF, GM-CSF, and G-CSF; interleukins (ILs), e.g., IL-1, IL-2 to IL-10; superoxide dismutase; T-cell receptors; surface membrane proteins; decay accelerating factor; transport proteins; homing receptors; addressins; fertility inhibitors such as the prostaglandins; fertility promoters; regulatory proteins; antibodies (including fragments thereof) and chimeric proteins, such as immunoadhesins. Suitable polypeptides may be native or recombinant and include, e.g., fusion proteins.

Examples of a polypeptide that may be encoded by the exogenous transcription unit also include CCL1, CCL2 (MCP-1), CCL3 (MIP-1α), CCL4 (MIP-1(3), CCL5 (RANTES), CCL6, CCL7, CCL8, CCL9 (CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1 (KC), CXCL2 (SDF1a), CXCL3, CXCL4, CXCL5, CXCL6, CXCL7, CXCL8 (IL8), CXCL9, CXCL10, CXCL11, CXCL12, CXCL13, CXCL14, CXCL15, CXCL16, CXCL17, CX3CL1, XCL1, XCL2, TNFA, TNFB (LTA), TNFC (LTB), TNFSF4, TNFSF5 (CD40LG), TNFSF6, TNFSF7, TNFSF8, TNFSF9, TNFSF10, TNFSF11, TNFSF13B, EDA, IL2, IL15, IL4, IL13, IL7, IL9, IL21, IL3, ILS, Il1.6, IL11, IL27, IL30, IL31, OSM, LIF, CNTF, CTF1, IL12a, IL12b, IL23, IL27, IL35, IL14, IL16, IL32, IL34, IL10, IL22, IL19, IL20, IL24, IL26, IL29, IFNL1, IFNL2, IFNL3, IL28, IFNA1, IFNA2, IFNA4, IFNA5, IFNA6, IFNA7, IFNA8, IFNA10, IFNA13, IFNA14, IFNA16, IFNA17, IFNA21, IFNB1, IFNK, IFNW1, IFNG, IL1A (IL1F1), IL1B (IL1F2), IL1Ra (IL1F3), IL1F5 (IL36RN), IL1F6 (IL36A), IL1F7 (IL37), IL1F8 (IL36B), IL1F9 (IL36G), IL1F10 (IL38), IL33 (IL1F11), IL18 (IL1G), IL17, KITLG, IL25 (IL17E), CSF1 (M-CSF), CSF2 (GM-CSF), CSF3 (G-CSF), SPP1, TGFB1, TGFB2, TGFB3, CCL3L1, CCL3L2, CCL3L3, CCL4L1, CCL4L2, IL17B, IL17C, IL17D, IL17F, AIMP1 (SCYE1), MIF, Areg, BC096441, Bmp1, Bmp10, Bmp15, Bmp2, Bmp3, Bmp4, Bmp5, Bmp6, Bmp7, Bmp8a, Bmp8b, Clqtnf 4, Cc121a, Cc127a, Cd70, Cer1, Ck1f, C1cf1, Cmtm 2a, Cmtm 2b, Cmtm 3, Cmtm 4, Cmtm 5, Cmtm 6, Cmtm 7, Cmtm 8, Cr1f1, Ctf2, Ebi3, Edn1, Fam3b, Fas1, Fgf2, Flt31, Gdf10, Gdf11, Gdf15, Gdf2, Gdf3, Gdf5, Gdf6, Gdf7, Gdf9, Gm12597, Gm13271, Gm13275, Gm13276, Gm13280, Gm13283, Gm2564, Gpi1, Grem 1, Grem 2, Grn, Hmgb 1, Ifna 11, Ifna 12, Ifna 9, Ifnab, Ifne, 1117a, I123a, I125, I131, I1tifb, Inhba, Lefty 1, Lefty 2, Mstn, Nampt, Ndp, Noda 1, Pf4, Pg1yrp 1, Pr17d1, Scg2, Scgb 3a1, Slurp 1, Spp1, Thpo, Tnfsf 10, Tnfsf 11, Tnfsf 12, Tnfsf 13, Tnfsf 13b, Tnfsf 14, Tnfsf 15, Tnfsf 18, Tnfsf 4, Tnfsf 8, Tnfsf 9, Ts1p, Vegfa, Wnt1, Wnt2, Wnt5a, Wnt7a, Xcl1, epinephrine, melatonin, triiodothyronine, a prostaglandin, a leukotriene, prostacyclin, thromboxane, islet amyloid polypeptide, mullerian inhibiting factor or hormone, adiponectin, corticotropin, angiotensin, vasopressin, arginine vasopressin, atriopeptin, brain natriuretic peptide, calcitonin, cholecystokinin, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, hepcidin, human chorionic gonadotropin, human placental lactogen, inhibin, somatomedin, leptin, lipotropin, melanocyte stimulating hormone, motilin, orexin, oxytocin, pancreatic polypeptide, pituitary adenylate cyclase-activating peptide, relaxin, renin, secretin, somatostatin, thrombopoietin, thyrotropin, thyrotropin-releasing hormone, vasoactive intestinal peptide, androgen, alpha-glucosidase (also known as acid maltase), glycogen phosphorylase, glycogen debrancher enzyme, phosphofructokinase, phosphoglycerate kinase, phosphoglycerate mutase, lactate dehydrogenase, carnitine palmityl transferase, carnitine, and myoadenylate deaminase.

In some embodiments, the polypeptide is a replacement therapy or a replacement protein. In some embodiments, the replacement therapy or replacement protein is a clotting factor or a coagulation factor, e.g., Factor VII, Factor VIII (e.g., comprises a naturally occurring human Factor VIII amino acid sequence or a variant thereof) or Factor IX (e.g., comprises a naturally occurring human Factor IX amino acid sequence or a variant thereof).

In some embodiments, the transcription unit encodes a FVII protein, e.g., a human FVII protein, e.g., comprises, consists essentially of, or consists of SEQ ID NO:18.

In some embodiments, the transcription unit encodes a Factor VIII protein, e.g., a human Factor VIII protein. In some embodiments, the Factor VIII protein is a B-domain-deleted Factor VIII protein (FVIII-BDD). In an embodiment, the FVIII-BDD protein comprises, consists essentially of, or consists of SEQ ID NO:8.

In some embodiments, the transcription unit encodes a Factor IX protein, e.g., a human Factor IX (FIX) protein. In some embodiments, the FIX protein is a FIX-padua protein and comprises, consists essentially of, or consists of SEQ ID NO:16.

In some embodiments, the replacement therapy or replacement protein is an enzyme, e.g., alpha-galactosidase A (GLA), alpha-L-iduronidase (IDUA), glucocerebrosidase, or N-sulfoglucosamine sulfohydrolase (SGSH).

In an embodiment, the genetically modified cells have one or more of the following characteristics: (i) are not capable of producing insulin (e.g., insulin A-chain, insulin B-chain, or proinsulin) in an amount effective to treat diabetes or another disease or condition that may be treated with insulin; (ii) not capable of producing insulin in a glucose-responsive manner; or (iii) not derived from an induced pluripotent stem cell that was engineered or differentiated into insulin-producing pancreatic beta cells.

Devices

A genetically modified cell described herein, e.g., a genetically modified RPE cell, or a plurality of such cells may be incorporated into, e.g., encapsulated within, an implantable device for use in providing a polypeptide encoded by the inserted transcription unit to a subject.

Exemplary implantable devices comprise materials such as metals, metallic alloys, ceramics, polymers, fibers, inert materials, and combinations thereof. The device can have any configuration and shape appropriate for supporting the viability and productivity of the encapsulated cells after implant into the intended target location. In some embodiments, the device is a hydrogel capsule, e.g., a millicapsule or a microcapsule (e.g., a hydrogel millicapsule or a hydrogel microcapsule). The device (e.g., capsule, particle) may comprise (and optionally is configured to release) one or more exogenous agents that are not expressed by the engineered cells. Such exogenous agents may include, e.g., a nucleic acid (e.g., an RNA or DNA molecule), a protein (e.g., a hormone, an enzyme (e.g., glucose oxidase, kinase, phosphatase, oxygenase, hydrogenase, reductase), an antibody, an antibody fragment, an antigen, a small molecule, a lipid, a drug, vaccine, or any derivative thereof, a small-molecule, an active or inactive fragment of a protein or polypeptide. In some embodiments, the device comprises at least one means for mitigating the foreign body response (FBR), for example, mitigate the FBR when the device is implanted into or onto a subject.

A device described herein may be provided as a preparation or composition for implantation or administration to a subject, i.e., a device preparation or device composition. In some embodiments, a device preparation or device composition comprises at least 2, 4, 8, 16, 32, 64 or more devices, and at least 20%, 30%, 35%, 40%, 45%, 50%, 55%, 60%, 65%, 70%, 75%, 80%, 85%, 90%, 95% or 100% of the devices in the preparation or composition have a characteristic as described herein, e.g., mean capsule diameter, or number of cells in the cell-containing compartment.

A device, device preparation or device composition may be configured for implantation, or is implanted or disposed, into or onto any site or part of the body. In some embodiments, the implantable device or device preparation is configured for implantation into the peritoneal cavity (e.g., the lesser sac, also known as the omental bursa or bursalis omentum). A device, device preparation or device composition may be implanted in the peritoneal cavity (e.g., the omentum, e.g., the lesser sac) or disposed on a surface within the peritoneal cavity (e.g., omentum, e.g., lesser sac) via injection or catheter. Additional considerations for implantation or disposition of a device, device preparation or device composition into the omentum (e.g., the lesser sac) are provided in M. Pellicciaro et al. (2017) *CellR*4 5(3): e2410.

In some embodiments, the implantable device comprises at least one cell-containing compartment comprising a plurality of live genetically modified cells encapsulated by a polymer composition. In an embodiment, the device contains two, three, four or more cell-containing compartments, each of which comprises a plurality of live, engineered cells described herein. In an embodiment, the cells in at least one of the compartments are capable of expressing and secreting GLA or a blood clotting factor, e.g., an FVIII protein, when the device is implanted into a subject.

In some embodiments, the polymer composition in the cell-containing compartment(s) comprises a polysaccharide or other hydrogel-forming polymer (e.g., alginate, hyaluronate or chondroitin). In some embodiments, the polymer is an alginate, which is a polysaccharide made up of β-D-mannuronic acid (M) and α-L-guluronic acid (G). In some embodiments, the alginate has a low molecular weight (e.g., approximate molecular weight of <75 kD) and G:M ratio ≥1.5, (ii) a medium molecular weight alginate, e.g., has approximate molecular weight of 75-150 kDa and G:M ratio ≥1.5, (iii) a high molecular weight alginate, e.g., has an approximate MW of 150 kDa-250 kDa and G:M ratio ≥1.5, (iv) or a blend of two or more of these alginates.

In some embodiments, the cell-containing compartment(s) further comprises at least one cell-binding substance (CBS), e.g., a cell-binding peptide (CBP) or cell-binding polypeptide (CBPP). In an embodiment, the CBS comprises a CBP covalently attached to polymer molecules in the polymer composition via a linker ("CBP-polymer"). In an embodiment, the polymer in the CBP-polymer is a polysaccharide (e.g., an alginate) or other hydrogel-forming polymer. Various cell-binding peptides for use in the devices of the disclosure are described herein. In an embodiment, the cell-binding peptide is 25 amino acids or less (e.g., 20, 15, 10 or less) in length and comprises the cell binding sequence of a ligand for a cell-adhesion molecule (CAM). In an embodiment, the cell-binding peptide consists essentially of a cell binding sequence shown in Table 1 herein. In an embodiment, the cell binding sequence is RGD or RGDSP. In an embodiment, the amino terminus of the cell-binding peptide is covalently attached to the polymer via an amino acid linker. In an embodiment, the amino acid linker consists essentially of one to three glycine residues. In an embodiment, the cell-binding peptide consists essentially of RGD or RGDSP and the linker consists essentially of a single glycine residue.

In some embodiments, the device further comprises at least one means for mitigating the foreign body response (FBR), for example, mitigate the FBR when the device is implanted into or onto a subject. Various means for mitigating the FBR of the devices are described herein, but any biological, chemical or physical element that is capable of reducing the FBR to the device compared to a reference device is contemplated herein.

For example, the means for mitigating the FBR in devices disclosed herein can comprise surrounding the cells with a semi-permeable biocompatible membrane having a pore size that is selected to allow oxygen and other molecules important to cell survival and function to move through the semi-permeable membrane while preventing immune cells from traversing through the pores. In an embodiment, the semi-permeable membrane has a molecular weight cutoff of less than 1000 kD or between 50-700 kD, 70-300 kD, or between 70-150 kD, or between 70 and 130 kD.

Another FBR-mitigating means comprises completely surrounding the cell-containing compartment with a barrier compartment formed from a cell-free biocompatible material, such as the two or three layer capsules described in WO 2014/153127, WO 2016/019391 or the core-shell microcapsules described in Ma, M et al., *Adv. Healthc Mater.,* 2(5):667-672 (2012). Such a barrier compartment could be used with or without the semi-permeable membrane means. FBR-mitigating means can comprise disposing on or within the device an anti-inflammatory drug that is released from the implanted device to inhibit FBR, e.g., as described in U.S. Pat. No. 9,867,781. Other FBR-mitigating means employ a CSF-1R inhibitor that is disposed on the device surface or encapsulated within the device, as described in WO 2017/176792 and WO 2017/176804. Other FBR-mitigating means employ configuring the device in a spherical shape with a diameter of greater than 1 mm, as described in Veiseh, O., et al., Nature Materials 14:643-652 (2015).

In some embodiments, the means for mitigating the FBR comprises disposing an afibrotic compound on the exterior surface of the device and/or within a barrier compartment surrounding the cell-containing compartment. Exemplary afibrotic compounds include compounds of Formula (I) described herein below. In some embodiments, the device can comprise combinations of two or more of the above FBR-mitigating means.

In some embodiments, the device has two hydrogel compartments, in which the inner, cell-containing compartment is completely surrounded by the second, outer (e.g., barrier) compartment. In an embodiment, the inner boundary of the second compartment forms an interface with the outer boundary of the first compartment, e.g., as illustrated in FIG. 7.

In some embodiments, one or more compartments in a device comprises an afibrotic polymer, e.g., an afibrotic compound of Formula (I) (defined herein below) covalently attached to a polymer that is the same or different than the polymer in the CBP-polymer. In an embodiment, some or all the monomers in the afibrotic polymer are modified with the same compound of Formula (I). In some embodiments, some or all the monomers in the afibrotic polymer are modified with different compounds of Formula (I). In some embodiments in which the device is a two-compartment hydrogel capsule, the afibrotic polymer is present only in the outer, barrier compartment, including its outer surface.

One or more compartments in a device may comprise an unmodified polymer that is the same or different than the polymer in the CBP-polymer and in any afibrotic polymer that is present in the device. In an embodiment, the first compartment, second compartment or all compartments in the device comprises the unmodified polymer. In some embodiments, the unmodified polymer is an unmodified alginate. In an embodiment, the unmodified alginate has a molecular weight of 150 kDa-250 kDa and a G:M ratio of ≥1.5.

Compounds of Formula (I)

In some embodiments, the devices described herein comprise a compound of Formula (I):

(I)

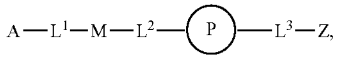

or a pharmaceutically acceptable salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)C(O)($C_1$-$C_6$-alkylene)-, —N($R^C$)C(O)($C_2$-$C_6$-alkenylene)-, —N($R^C$)N($R^D$)—, —NCN—, —C(=N($R^C$)($R^D$))O—, —S—, —S$(O)_x$—, —OS$(O)_x$—, —N($R^C$)S$(O)_x$—, —S$(O)_x$N($R^C$)—, —P$(R^F)_y$—, —Si$(OR^A)_2$—, —Si($R^G$)($OR^A$)—, —B($OR^A$)—, or a metal, each of which is optionally linked to an attachment group (e.g., an attachment group described herein) and is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is absent, cycloalkyl, heterocycyl, or heteroaryl, each of which is optionally substituted by one or more $R^4$;

Z is hydrogen, alkyl, alkenyl, alkynyl, heteroalkyl, —$OR^A$, —C(O)$R^A$, —C(O)$OR^A$, —C(O)N($R^C$)($R^D$), —N($R^C$)C(O)$R^A$ cycloalkyl, heterocyclyl, aryl, or heteroaryl, wherein each, alkyl, alkenyl, alkynyl, heteroalkyl, cycloalkyl, heterocyclyl, aryl, and heteroaryl is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, S$(O)_x R^{E1}$, —OS$(O)_x R^{E1}$, —N($R^{C1}$)S$(O)_x R^{E1}$, —S$(O)_x$N($R^{C1}$)($R^{D1}$), —P$(R^{F1})_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R_{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, the compound of Formula (I) is a compound of Formula (I-a):

(I-a)

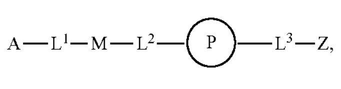

or a salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, —NCN—, —N($R^C$)C(O)($C_1$-$C_6$-alkylene)-, —N($R^C$)C(O)($C_2$-$C_6$-alkenylene)-, —C(=N($R^C$)($R^D$))O—, —S—, —S(O)$_x$—, —OS(O)$_x$—, —N($R^C$)S(O)$_x$—, —S(O)$_x$N($R^C$)—, —P($R^F$)$_y$—, —Si($OR^A$)$_2$—, —Si($R^G$)($OR^A$)—, —B($OR^A$)—, or a metal, each of which is optionally linked to an attachment group (e.g., an attachment group described herein) and optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is heteroaryl optionally substituted by one or more $R^4$;

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, S(O)$_x$$R^{E1}$, —OS(O)$_x$$R^{E1}$, —N($R^{C1}$)S(O)$_x$$R^{E1}$, —S(O)$_x$N($R^{C1}$)($R^{D1}$), cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, for Formulas (I) or (I-a), A is alkyl, alkenyl, alkynyl, heteroalkyl, cycloalkyl, heterocyclyl, aryl, heteroaryl, —O—, —C(O)O—, —C(O)—, —OC(O)—, —N($R^C$)C(O)—, —N($R^C$)C(O)($C_1$-$C_6$-alkylene)-, —N($R^C$)C(O)($C_2$-$C_6$-alkenylene)-, or —N($R^C$)—. In some embodiments, A is alkyl, alkenyl, alkynyl, heteroalkyl, cycloalkyl, heterocyclyl, aryl, heteroaryl, —O—, —C(O)O—, —C(O)—, —OC(O)—, or —N($R^C$)—. In some embodiments, A is alkyl, alkenyl, alkynyl, heteroalkyl, —O—, —C(O)O—, —C(O)—, —OC(O)—, or —N($R^C$)—. In some embodiments, A is alkyl, —O—, —C(O)O—, —C(O)—, —OC(O), or —N($R^C$)—. In some embodiments, A is —N($R^C$)C(O)—, —N($R^C$)C(O)($C_1$-$C_6$-alkylene)-, or —N($R^C$)C(O)($C_1$-$C_6$-alkenylene)-. In some embodiments, A is —N($R^C$)—. In some embodiments, A is —N($R^C$)—, and $R^C$ an $R^D$ is independently hydrogen or alkyl. In some embodiments, A is —NH—. In some embodiments, A is —N($R^C$)C(O)($C_1$-$C_6$-alkylene)-, wherein alkylene is substituted with $R^1$. In some embodiments, A is —N($R^C$)C(O)($C_1$-$C_6$-alkylene)-, and $R^1$ is alkyl (e.g., methyl). In some embodiments, A is —NHC(O)C($CH_3$)$_2$—. In some embodiments, A is —N($R^C$)C(O)(methylene)-, and $R^1$ is alkyl (e.g., methyl). In some embodiments, A is —NHC(O)CH($CH_3$)—. In some embodiments, A is —NHC(O)C($CH_3$)—.

In some embodiments, for Formulas (I) or (I-a), $L^1$ is a bond, alkyl, or heteroalkyl. In some embodiments, $L^1$ is a bond or alkyl. In some embodiments, $L^1$ is a bond. In some embodiments, $L^1$ is alkyl. In some embodiments, $L^1$ is $C_1$-$C_6$ alkyl. In some embodiments, $L^1$ is —$CH_2$—, —CH($CH_3$)—, —$CH_2CH_2CH_2$, or —$CH_2CH_2$—. In some embodiments, $L^1$ is —$CH_2$— or —$CH_2CH_2$—.

In some embodiments, for Formulas (I) or (I-a), $L^3$ is a bond, alkyl, or heteroalkyl. In some embodiments, $L^3$ is a bond. In some embodiments, $L^3$ is alkyl. In some embodiments, $L^3$ is $C_{12}$ alkyl. In some embodiments, $L^3$ is $C_1$-$C_6$ alkyl. In some embodiments, $L^3$ is —$CH_2$—. In some embodiments, $L^3$ is heteroalkyl. In some embodiments, $L^3$ is $C_1$-$C_{12}$ heteroalkyl, optionally substituted with one or more $R^2$ (e.g., oxo). In some embodiments, $L^3$ is $C_1$-$C_6$ heteroalkyl, optionally substituted with one or more $R^2$ (e.g., oxo). In some embodiments, $L^3$ is —C(O)$OCH_2$—, —$CH_2$($OCH_2CH_2$)$_2$—, —$CH_2$($OCH_2CH_2$)$_3$—, $CH_2CH_2O$—, or —$CH_2O$—. In some embodiments, $L^3$ is —$CH_2O$—.

In some embodiments, for Formulas (I) or (I-a), M is absent, alkyl, heteroalkyl, aryl, or heteroaryl. In some embodiments, M is heteroalkyl, aryl, or heteroaryl. In some embodiments, M is absent. In some embodiments, M is alkyl (e.g., $C_1$-$C_6$ alkyl). In some embodiments, M is —$CH_2$—. In some embodiments, M is heteroalkyl (e.g., $C_1$-$C_6$ heteroalkyl). In some embodiments, M is (—$OCH_2CH_2$—)z, wherein z is an integer selected from 1 to 10. In some embodiments, z is an integer selected from 1 to 5. In some embodiments, M is —$OCH_2CH_2$—, (—$OCH_2CH_2$—)$_2$, (—$OCH_2CH_2$—)$_3$, (—$OCH_2CH_2$—)$_4$, or (—$OCH_2CH_2$—)$_5$. In some embodiments, M is —$OCH_2CH_2$—, (—$OCH_2CH_2$—)$_2$, (—$OCH_2CH_2$—)$_3$, or (—$OCH_2CH_2$—)$_4$. In some embodiments, M is (—$OCH_2CH_2$—)$_3$. In some embodiments, M is aryl. In some embodiments, M is phenyl. In some embodiments, M is unsubstituted phenyl. In some embodiments, M is

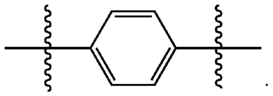 [SMILES: *c1ccc(*)cc1]

n some embodiments, M is phenyl substituted with $R^7$ (e.g., 1 $R^7$). In some embodiments, M is

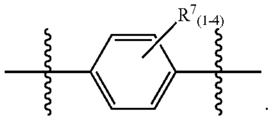

In some embodiments, $R^7$ is $CF_3$.

In some embodiments, for Formulas (I) or (I-a), P is absent, heterocyclyl, or heteroaryl. In some embodiments, P is absent. In some embodiments, for Formulas (I) and (I-a), P is a tricyclic, bicyclic, or monocyclic heteroaryl. In some embodiments, P is a monocyclic heteroaryl. In some embodiments, P is a nitrogen-containing heteroaryl. In some embodiments, P is a monocyclic, nitrogen-containing heteroaryl. In some embodiments, P is a 5-membered heteroaryl. In some embodiments, P is a 5-membered nitrogen-containing heteroaryl. In some embodiments, P is tetrazolyl, imidazolyl, pyrazolyl, or triazolyl, pyrrolyl, oxazolyl, or thiazolyl. In some embodiments, P is tetrazolyl, imidazolyl, pyrazolyl, or triazolyl, or pyrrolyl. In some embodiments, P is imidazolyl. In some embodiments, P is

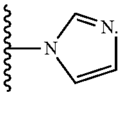 [SMILES: *n1ccnc1]

In some embodiments, P is triazolyl. In some embodiments, P is 1,2,3-triazolyl. In some embodiments, P is

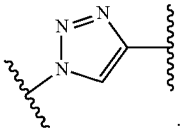 [SMILES: *c1cn(*)nn1]

In some embodiments, P is heterocyclyl. In some embodiments, P is a 5-membered heterocyclyl or a 6-membered heterocyclyl. In some embodiments, P is imidazolidinonyl. In some embodiments, P is

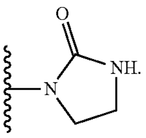 [SMILES: *N1CCNC1=O]

In some embodiments, P is thiomorpholinyl-1,1-dioxidyl. In some embodiments, P is

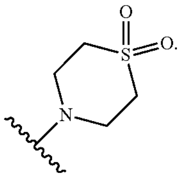 [SMILES: *N1CCS(=O)(=O)CC1]

In some embodiments, for Formulas (I) or (I-a), Z is alkyl, heteroalkyl, cycloalkyl, heterocyclyl, aryl, or heteroaryl. In some embodiments, Z is heterocyclyl. In some embodiments, Z is monocyclic or bicyclic heterocyclyl. In some embodiments, Z is an oxygen-containing heterocyclyl. In some embodiments, Z is a 4-membered heterocyclyl, 5-membered heterocyclyl, or 6-membered heterocyclyl. In some embodiments, Z is a 6-membered heterocyclyl. In some embodiments, Z is a 6-membered oxygen-containing heterocyclyl. In some embodiments, Z is tetrahydropyranyl. In some embodiments, Z is

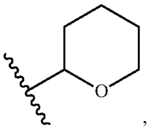
,
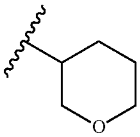
, or
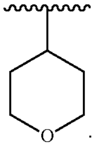
.

In some embodiments, Z is a 4-membered oxygen-containing heterocyclyl. In some embodiments, Z is

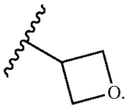 [SMILES: *C1COC1]

In some embodiments, Z is a bicyclic oxygen-containing heterocyclyl. In some embodiments, Z is phthalic anhydridyl. In some embodiments, Z is a sulfur-containing heterocyclyl. In some embodiments, Z is a 6-membered sulfur-containing heterocyclyl. n some embodiments, Z is a 6-membered heterocyclyl containing a nitrogen atom and a sulfur atom. In some embodiments, Z is thiomorpholinyl-1,1-dioxidyl. In some embodiments, Z is

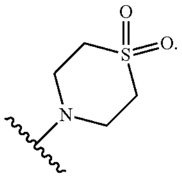 [SMILES: *N1CCS(=O)(=O)CC1]

In some embodiments, Z is a nitrogen-containing heterocyclyl. In some embodiments, Z is a 6-membered nitrogen-containing heterocyclyl. In some embodiments, Z is

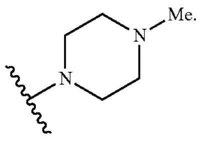 [SMILES: *N1CCN(C)CC1]

In some embodiments, Z is a bicyclic heterocyclyl. In some embodiments, Z is a bicyclic nitrogen-containing heterocyclyl, optionally substituted with one or more $R^5$. In some embodiments, Z is 2-oxa-7-azaspiro[3.5]nonanyl. In some embodiments, Z is

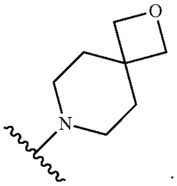 [SMILES: *N1CCC2(CC1)COC2]

In some embodiments, Z is 1-oxa-3,8-diazaspiro[4.5]decan-2-one. In some embodiments, Z is

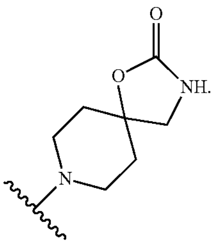 [SMILES: *N1CCC2(CC1)CNC(=O)O2]

In some embodiments, for Formulas (I) or (I-a), Z is aryl. In some embodiments, Z is monocyclic aryl. In some embodiments, Z is phenyl. In some embodiments, Z is monosubstituted phenyl (e.g., with 1 $R^5$). In some embodiments, Z is monosubstituted phenyl, wherein the 1 $R^5$ is a nitrogen-containing group. In some embodiments, Z is monosubstituted phenyl, wherein the 1 $R^5$ is $NH_2$. In some embodiments, Z is monosubstituted phenyl, wherein the 1 $R^5$ is an oxygen-containing group. In some embodiments, Z is monosubstituted phenyl, wherein the 1 $R^5$ is an oxygen-containing heteroalkyl. In some embodiments, Z is monosubstituted phenyl, wherein the 1 $R^5$ is $OCH_3$. In some embodiments, Z is monosubstituted phenyl, wherein the 1 $R^5$ is in the ortho position. In some embodiments, Z is monosubstituted phenyl, wherein the 1 $R^5$ is in the meta position. In some embodiments, Z is monosubstituted phenyl, wherein the 1 $R^5$ is in the para position.

In some embodiments, for Formulas (I) or (I-a), Z is alkyl. In some embodiments, Z is $C_1$-$C_{12}$ alkyl. In some embodiments, Z is $C_1$-$C_{10}$ alkyl. In some embodiments, Z is $C_1$-$C_8$ alkyl. In some embodiments, Z is $C_1$-$C_8$ alkyl substituted with 1-5 $R^5$. In some embodiments, Z is $C_1$-$C_8$ alkyl substituted with 1 $R^5$. In some embodiments, Z is $C_1$-$C_8$ alkyl substituted with 1 $R^5$, wherein $R^5$ is alkyl, heteroalkyl, halogen, oxo, —$OR^{A1}$, $C(O)OR^{A1}$, $C(O)R^{B1}$, —$OC(O)R^{B1}$, or —$N(R^{C1})(R^{D1})$. In some embodiments, Z is $C_1$-$C_8$ alkyl substituted with 1 $R^5$, wherein $R^5$ is —$OR^{A1}$ or —$C(O)OR^{A1}$. In some embodiments, Z is $C_1$-$C_8$ alkyl substituted with 1 $R^5$, wherein $R^5$ is —$OR^{A1}$ or —C(O)OH. In some embodiments, Z is —$CH_3$.

In some embodiments, for Formulas (I) or (I-a), Z is heteroalkyl. In some embodiments, Z is $C_1$-$C_{12}$ heteroalkyl. In some embodiments, Z is $C_1$-$C_{10}$ heteroalkyl. In some embodiments, Z is $C_1$-$C_8$ heteroalkyl. In some embodiments, Z is $C_1$-$C_6$ heteroalkyl. In some embodiments, Z is a nitrogen-containing heteroalkyl optionally substituted with one or more $R^5$. In some embodiments, Z is a nitrogen and sulfur-containing heteroalkyl substituted with 1-5 $R^5$. In some embodiments, Z is N-methyl-2-(methyl sulfonyl) ethan-1-aminyl.

In some embodiments, Z is —$OR^A$ or —$C(O)OR^A$. In some embodiments, Z is —$OR^A$ (e.g., —OH or —$OCH_3$). In some embodiments, Z is —$OCH_3$. In some embodiments, Z is —$C(O)OR^A$ (e.g., —C(O)OH).

In some embodiments, Z is hydrogen.

In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound of Formula (I) is a compound of Formula (I-b):

(I-b)

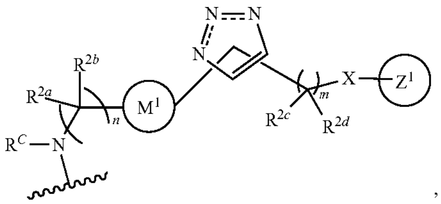

, or a salt thereof, wherein Ring $M^1$ is cycloalkyl, heterocyclyl, aryl, or heteroaryl, each of which is optionally substituted with 1-5 $R^3$; Ring $Z^1$ is cycloalkyl, heterocyclyl, aryl or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl, or each of $R^{2a}$ and $R^{2b}$ or $R^{2c}$ and $R^{2d}$ is taken together to form an oxo group; X is absent,) $N(R^{10})$, O, or S; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, $N(R^{C1})C(O)R^{B1}$, —$C(O)N(R^{C1})$, $SR^{E1}$, cycloalkyl, heterocyclyl, aryl, or heteroaryl; $R^{10}$ is hydrogen, alkyl, alkenyl, alkynyl, heteroalkyl, —$C(O)OR^{A1}$, —$C(O)R^{B1}$, —$OC(O)R^{B1}$, —$C(O)N(R^{C1})$, cycloalkyl, heterocyclyl, aryl, or heteroaryl; each $R^{A1}$, $R^{B1}$, $R^{C1}$, $R^{D1}$ and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 1, 2, 3, 4, 5, or 6; and " ~~~ " refers to a connection to an attachment group or a polymer described herein. In some embodiments, for each $R^3$ and $R^5$, each alkyl, alkenyl, alkynyl, heteroalkyl, cycloalkyl, heterocyclyl, aryl, or heteroaryl is optionally and independently substituted with halogen, oxo, cyano, cycloalkyl, or heterocyclyl.

In some embodiments, the compound of Formula (I-b) is a compound of Formula (I-b-i):

(I-b-i)

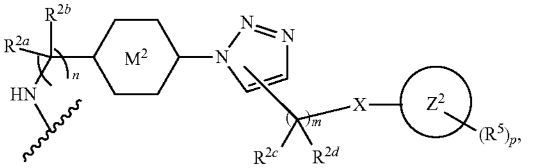

or a pharmaceutically acceptable salt thereof, wherein Ring $M^2$ is aryl or heteroaryl optionally substituted with one or more $R^3$; Ring $Z^2$ is cycloalkyl, heterocyclyl, aryl, or heteroaryl; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; X is absent, O, or S; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; or two $R^5$ are taken together to form a 5-6 membered ring fused to Ring $Z^2$; each $R^{A1}$ and $R^{B1}$ is independently hydrogen, alkyl, or heteroalkyl; m and n are each independently 1, 2, 3, 4, 5, or 6; p is 0, 1, 2, 3, 4, 5, or 6; and "∿∿" refers to a connection to an attachment group or a polymer described herein.

In some embodiments, the compound of Formula (I-b-i) is a compound of Formula (I-b-ii):

(I-b-ii)

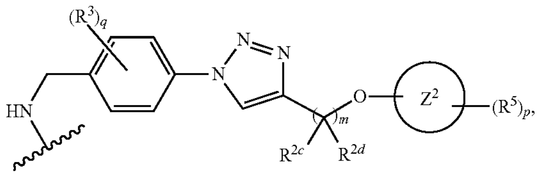

or a pharmaceutically acceptable salt thereof, wherein Ring $Z^2$ is cycloalkyl, heterocyclyl, aryl or heteroaryl; each of $R^{2c}$ and $R^{2d}$ is independently hydrogen, alkyl, or heteroalkyl, or $R^{2c}$ and $R^{2d}$ and taken together to form an oxo group; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; each of p and q is independently 0, 1, 2, 3, 4, 5, or 6; and "∿∿" refers to a connection to an attachment group or a polymer described herein.

In some embodiments, the compound of Formula (I) is a compound of Formula (I-c):

(I-c)

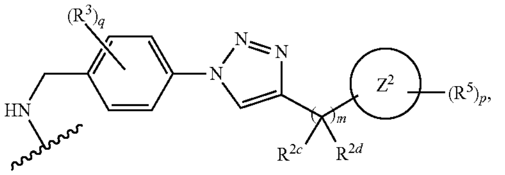

or a pharmaceutically acceptable salt thereof, wherein Ring $Z^2$ is cycloalkyl, heterocyclyl, aryl or heteroaryl; each of $R^{2c}$ and $R^{2d}$ is independently hydrogen, alkyl, or heteroalkyl, or $R^{2c}$ and $R^{2d}$ is taken together to form an oxo group; each $R^3$ and $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; m is 1, 2, 3, 4, 5, or 6; each of p and q is independently 0, 1, 2, 3, 4, 5, or 6; and "∿∿" refers to a connection to an attachment group or a polymer described herein.

In some embodiments, the compound of Formula (I) is a compound of Formula (I-d):

(I-d)

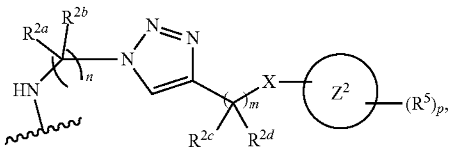

or a pharmaceutically acceptable salt thereof, wherein Ring $Z^2$ is cycloalkyl, heterocyclyl, aryl or heteroaryl; X is absent, O, or S; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2a}$ and $R^{2d}$ is taken together to form an oxo group; each $R^5$ is independently alkyl, heteroalkyl, halogen, oxo, —$OR^{A1}$, —$C(O)OR^{A1}$, or —$C(O)R^{B1}$, wherein each alkyl and heteroalkyl is optionally substituted with halogen; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and "∿∿" refers to a connection to an attachment group or a polymer described herein.

In some embodiments, the compound of Formula (I) is a compound of Formula (I-e):

(I-e)

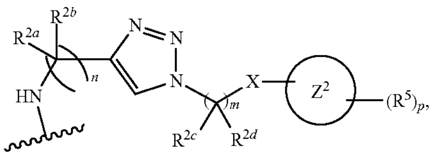

or a pharmaceutically acceptable salt thereof, wherein Ring $Z^2$ is cycloalkyl, heterocyclyl, aryl or heteroaryl; X is absent, O, or S; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and "∿∿" refers to a connection to an attachment group or a polymer described herein.

In some embodiments, the compound of Formula (I) is a compound of Formula (I-f):

(I-f)

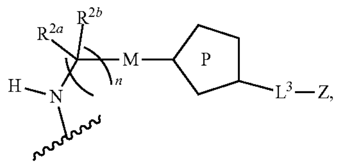

or a pharmaceutically acceptable salt thereof, wherein M is alkyl optionally substituted with one or more $R^3$; Ring P is heteroaryl optionally substituted with one or more $R^4$; $L^3$ is alkyl or heteroalkyl optionally substituted with one or more $R^2$; Z is alkyl, heteroalkyl, cycloalkyl, heterocyclyl, aryl, or heteroaryl, each of which is optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, $R^4$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and " ∿∿∿ " refers to a connection to an attachment group or a polymer described herein.

In some embodiments, the compound of Formula (I) is a compound of Formula (II):

(II)

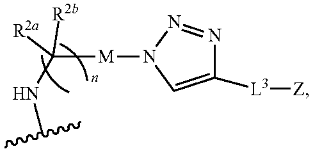

or a pharmaceutically acceptable salt thereof, wherein M is a bond, alkyl or aryl, wherein alkyl and aryl is optionally substituted with one or more $R^3$; $L^3$ is alkyl or heteroalkyl optionally substituted with one or more $R^2$; Z is hydrogen, alkyl, heteroalkyl, cycloalkyl, heterocyclyl, aryl, heteroaryl or —$OR^A$, wherein alkyl, heteroalkyl, cycloalkyl, heterocyclyl, aryl, and heteroaryl is optionally substituted with one or more $R^5$; $R^A$ is hydrogen; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and " ∿∿∿ " refers to a connection to an attachment group or a polymer described herein.

In some embodiments, the compound of Formula (II) is a compound of Formula (II-a):

(II-a)

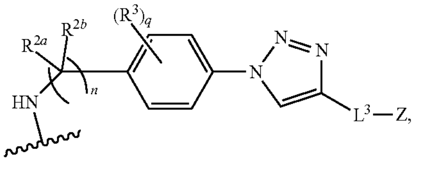

or a pharmaceutically acceptable salt thereof, wherein $L^3$ is alkyl or heteroalkyl, each of which is optionally substituted with one or more $R^2$; Z is hydrogen, alkyl, heteroalkyl, or —$OR^A$, wherein alkyl and heteroalkyl are optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; $R^A$ is hydrogen; each $R^{A1}$ and $R^{B1}$ is independently hydrogen, alkyl, or heteroalkyl; n is independently 1, 2, 3, 4, 5, or 6; and " ∿∿∿ " refers to a connection to an attachment group or a polymer described herein.

In some embodiments, the compound of Formula (I) is a compound of Formula (III):

(III)

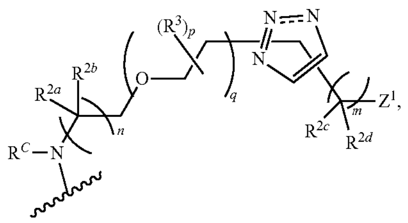

or a pharmaceutically acceptable salt thereof, wherein $Z^1$ is alkyl, alkenyl, alkynyl, heteroalkyl, cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ is hydrogen, alkyl, alkenyl, alkynyl, or heteroalkyl, wherein each of alkyl, alkenyl, alkynyl, or heteroalkyl is optionally substituted with 1-6 $R^6$; each of $R^3$, $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; q is an integer from 0 to 25; and " ∿∿∿ " refers to a connection to an attachment group or a polymer described herein.

In some embodiments, the compound of Formula (III) is a compound of Formula (III-a):

(III-a)

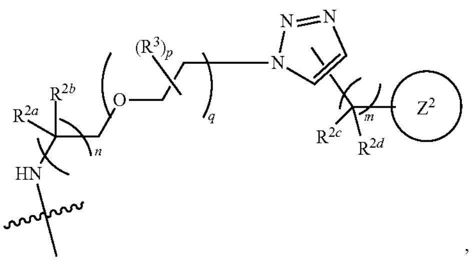

, or a pharmaceutically acceptable salt thereof, wherein Ring $Z^2$ is cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; o and p are each independently 0, 1, 2, 3, 4, or 5; q is an integer from 0 to 25; and "~~~" refers to a connection to an attachment group or a polymer described herein.

In some embodiments, the compound of Formula (III-a) is a compound of Formula (III-b):

(III-b)

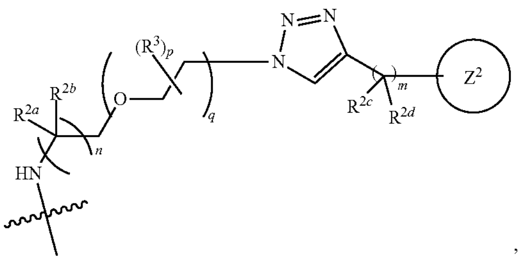

, or a pharmaceutically acceptable salt thereof, wherein Ring $Z^2$ is cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; o and p are each independently 0, 1, 2, 3, 4, or 5; q is an integer from 0 to 25; and "~~~" refers to a connection to an attachment group or a polymer described herein.

In some embodiments, the compound of Formula (III-a) is a compound of Formula (III-c):

(III-c)

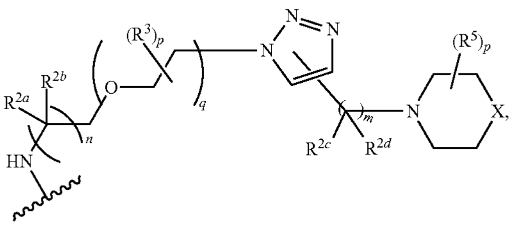

or a pharmaceutically acceptable salt thereof, wherein X is C(R')(R"), N(R'), or $S(O)_x$; each of R' and R" is independently hydrogen, alkyl, halogen, or cycloalkyl; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; p is 0, 1, 2, 3, 4, or 5; q is an integer from 0 to 25; x is 0, 1, or 2; and "~~~" refers to a connection to an attachment group or a polymer described herein.

In some embodiments, the compound of Formula (III-c) is a compound of Formula (III-d):

(III-d)

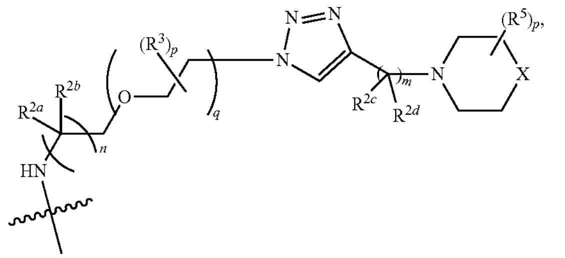

or a pharmaceutically acceptable salt thereof, wherein X is C(R')(R"), N(R'), or $S(O)_x$; each of R' and R" is independently hydrogen, alkyl, halogen, or cycloalkyl; each of $R^{2a}$, $R^{2b}$, $R^{2c}$ and $R^{2d}$ is independently hydrogen, alkyl, heteroalkyl, or halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; p is 0, 1, 2, 3, 4, or 5; q is an integer from 0 to 25; x is 0, 1, or 2; and "~~~" refers to a connection to an attachment group or a polymer described herein.

In some embodiments, the compound is a compound of Formula (I). In some embodiments, $L^2$ is a bond and P and $L^3$ are independently absent.

In some embodiments, the compound is a compound of Formula (I-a). In some embodiments of Formula (II-a), $L^2$ is a bond, P is heteroaryl, $L^3$ is a bond, and Z is hydrogen. In some embodiments, P is heteroaryl, $L^3$ is heteroalkyl, and Z is alkyl. In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound is a compound of Formula (I-b). In some embodiments, P is absent, $L^1$ is —$NHCH_2$, $L^2$ is a bond, M is aryl (e.g., phenyl), $L^3$ is —$CH_2O$, and Z is heterocyclyl (e.g., a nitrogen-containing heterocyclyl, e.g., thiomorpholinyl-1,1-dioxide). In some embodiments, the compound of Formula (I-b) is Compound 116.

In some embodiments of Formula (I-b), P is absent, $L^1$ is —$NHCH_2$, $L^2$ is a bond, M is absent, $L^3$ is a bond, and Z is heterocyclyl (e.g., an oxygen-containing heterocyclyl, e.g., tetrahydropyranyl, tetrahydrofuranyl, oxetanyl, or oxiranyl). In some embodiments, the compound of Formula (I-b) is Compound 105.

In some embodiments, the compound is a compound of Formula (I-b-i). In some embodiments of Formula (I-b-i), each of $R^{2a}$ and $R^{2b}$ is independently hydrogen or $CH_3$, each of $R^{2c}$ and $R^{2d}$ is independently hydrogen, m is 1 or 2, n is 1, X is O, p is 0, $M^2$ is phenyl optionally substituted with one or more $R^3$, $R^3$ is —$CF_3$, and $Z^2$ is heterocyclyl (e.g., an oxygen-containing heterocyclyl, e.g., tetrahydropyranyl, tetrahydrofuranyl, oxetanyl, or oxiranyl). In some embodiments, the compound of Formula (I-b-i) is Compound 100, Compound 106, Compound 107, Compound 108, Compound 109, or Compound 111.

In some embodiments, the compound is a compound of Formula (I-b-ii). In some embodiments of Formula (I-b-ii), each of $R^{2a}$, $R^{2b}$, $R^{2c}$, and $R^{2d}$ is independently hydrogen, q is 0, p is 0, m is 1, and $Z^2$ is heterocyclyl (e.g., an oxygen-containing heterocyclyl, e.g., tetrahydropyranyl). In some embodiments, the compound of Formula (I-b-ii) is Compound 100.

In some embodiments, the compound is a compound of Formula (I-c). In some embodiments of Formula (I-c), each of $R^{2c}$ and $R^{2d}$ is independently hydrogen, m is 1, p is 1, q is 0, $R^5$ is —$CH_3$, and Z is heterocyclyl (e.g., a nitrogen-containing heterocyclyl, e.g., piperazinyl). In some embodiments, the compound of Formula (I-c) is Compound 113.

In some embodiments, the compound is a compound of Formula (I-d). In some embodiments of Formula (I-d), each of $R^{2a}$, $R^{2b}$, $R^{2c}$, and $R^{2d}$ is independently hydrogen, m is 1, n is 3, X is O, p is 0, and Z is heterocyclyl (e.g., an oxygen-containing heterocyclyl, e.g., tetrahydropyranyl, tetrahydrofuranyl, oxetanyl, or oxiranyl). n some embodiments, the compound of Formula (I-d) is Compound 110 or Compound 114.

In some embodiments, the compound is a compound of Formula (I-f). In some embodiments of Formula (I-f), each of $R^{2a}$ and $R^{2b}$ is independently hydrogen, n is 1, M is —$CH_2$—, P is a nitrogen-containing heteroaryl (e.g., imidazolyl), $L^3$ is —C(O)O$CH_2$—, and Z is $CH_3$. In some embodiments, the compound of Formula (I-f) is Compound 115.

In some embodiments, the compound is a compound of Formula (II-a). In some embodiments of Formula (II-a), each of $R^{2a}$ and $R^{2b}$ is independently hydrogen, n is 1, q is 0, $L^3$ is —$CH_2(OCH_2CH_2)_2$, and Z is —$OCH_3$. In some embodiments, the compound of Formula (II-a) is Compound 112.

In some embodiments of Formula (II-a), each of $R^{2a}$ and $R^{2b}$ is independently hydrogen, n is 1, $L^3$ is a bond or —$CH_2$, and Z is hydrogen or —OH. In some embodiments, the compound of Formula (II-a) is Compound 103 or Compound 104.

In some embodiments, the compound is a compound of Formula (III). In some embodiments of Formula (III), each of $R^{2a}$ and $R^{2d}$ is independently hydrogen, m is 1, n, $R^{2b}$, is 2, q is 3, p is 0, $R^C$ is hydrogen, and $Z^1$ is heteroalkyl optionally substituted with $R^5$ (e.g., —$N(CH_3)(CH_2CH_2)S(O)_2CH_3$). In some embodiments, the compound of Formula (III) is Compound 120.

In some embodiments, the compound is a compound of Formula (III-b). In some embodiments of Formula (III-b), each of $R^{2a}$, $R_{2b}$, $R_{2c}$, and $R_{2d}$ is independently hydrogen, m is 0, n is 2, q is 3, p is 0, and $Z^2$ is aryl (e.g., phenyl) substituted with 1 $R^5$ (e.g., —$NH_2$). In some embodiments, the compound of Formula (III-b) is Compound 102.

In some embodiments, the compound is a compound of Formula (III-b). In some embodiments of Formula (III-b), each of $R^{2a}$, $R^{2b}$, $R^{2c}$, and $R^{2d}$ is independently hydrogen, m is 1, n is 2, q is 3, p is 0, $R^C$ is hydrogen, and $Z^2$ is heterocyclyl (e.g., an nitrogen-containing heterocyclyl, e.g., a nitrogen-containing spiro heterocyclyl, e.g., 2-oxa-7-azaspiro[3.5]nonanyl). In some embodiments, the compound of Formula (III-a) is Compound 121.

In some embodiments, the compound is a compound of Formula (III-d). In some embodiments of Formula (III-d), each of $R^{2a}$, $R^{2b}$, $R^{2c}$, and $R^{2d}$ is independently hydrogen, m is 1, n is 2, q is 1, 2, 3, or 4, p is 0, and X is $S(O)_2$. In some embodiments of Formula (III-d), each of $R^{2a}$ and $R^{2b}$ is independently hydrogen, m is 1, n is 2, q is 1, 2, 3, or 4, p is 0, and X is $S(O)_2$. In some embodiments, the compound of Formula (III-d) is Compound 101, Compound 117, Compound 118, or Compound 119.

In some embodiments, the compound is a compound of Formula (I-b), (I-d), or (I-e). In some embodiments, the compound is a compound of Formula (I-b), (I-d), or (II). In some embodiments, the compound is a compound of Formula (I-b), (I-d), or (I-f). In some embodiments, the compound is a compound of Formula (I-b), (I-d), or (III).

Exemplary compounds of Formula (I) may be prepared as described in WO 2019/169333 or any other method known to those skilled in the art.

In some embodiments, the compound of Formula (I) is not a compound disclosed in WO 2012/112982, WO 2012/167223, WO 2014/153126, WO 2016/019391, WO 2017/075630, US 2012-0213708, US 2016-0030359 or US2016-0030360.

In some embodiments, the compound of Formula (I) comprises a compound shown in Table 3, or a pharmaceutically acceptable salt thereof. In some embodiments, a device described herein comprises a compound shown in Table 3, or a pharmaceutically acceptable salt thereof.

TABLE 3

Exemplary compounds of Formula (I)

| Compound No. | Structure |
| --- | --- |
| 100 | 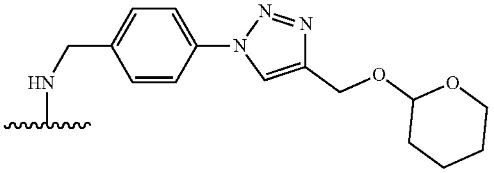 [SMILES: *NCc1ccc(-n2cc(COC3CCCCO3)nn2)cc1] |
| 101 | 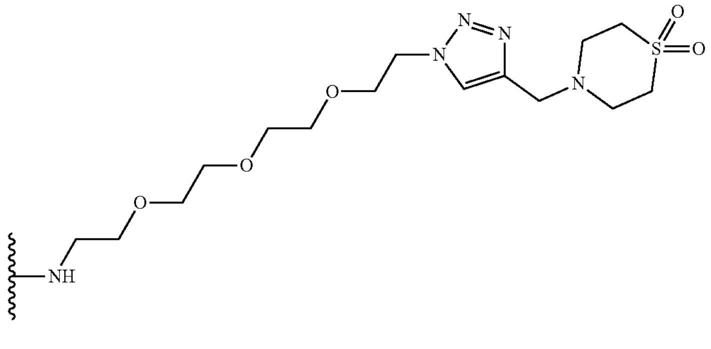 [SMILES: *NCCOCCOCCOCCn1cc(CN2CCS(=O)(=O)CC2)nn1] |

TABLE 3-continued
| Exemplary compounds of Formula (I) | |
|---|---|
| Compound No. | Structure |
| 102 | 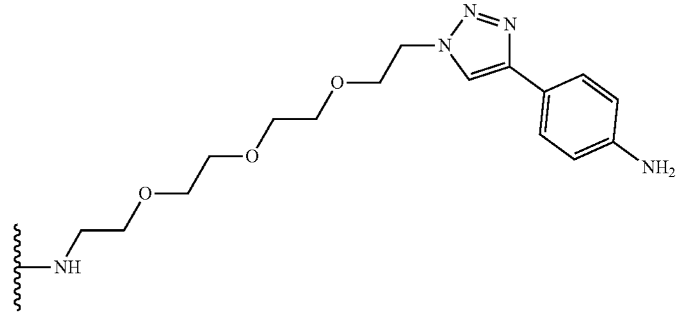 [SMILES: *NCCOCCOCCOCCn1cc(-c2ccc(N)cc2)nn1] |
| 103 | 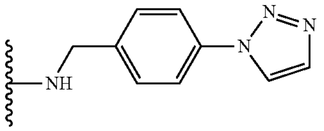 [SMILES: *NCc1ccc(-n2ccnn2)cc1] |
| 104 | 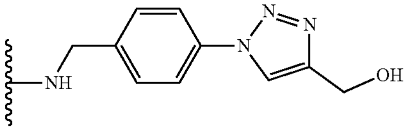 [SMILES: *NCc1ccc(-n2cc(CO)nn2)cc1] |
| 105 | 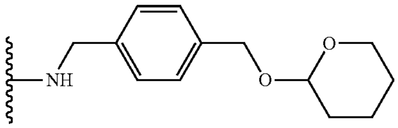 [SMILES: *NCc1ccc(COC2CCCCO2)cc1] |
| 106 | 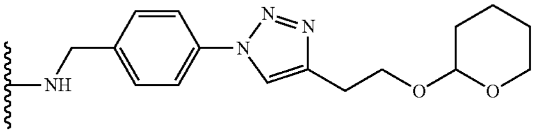 [SMILES: *NCc1ccc(-n2cc(CCOC3CCCCO3)nn2)cc1] |
| 107 | 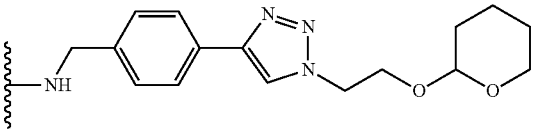 [SMILES: *NCc1ccc(-c2cn(CCOC3CCCCO3)nn2)cc1] |
| 108 | 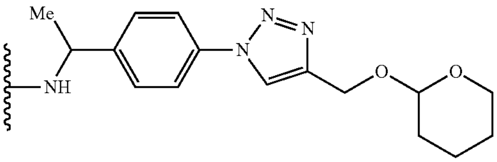 [SMILES: *NC(C)c1ccc(-n2cc(COC3CCCCO3)nn2)cc1] |
| 109 | 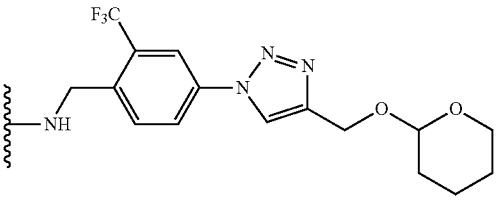 [SMILES: *NCc1ccc(-n2cc(COC3CCCCO3)nn2)cc1C(F)(F)F] |

TABLE 3-continued
| Exemplary compounds of Formula (I) | |
|---|---|
| Compound No. | Structure |
| 110 | 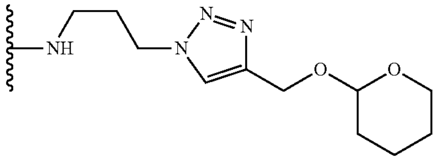 [SMILES: *NCCCn1cc(COC2CCCCO2)nn1] |
| 111 | 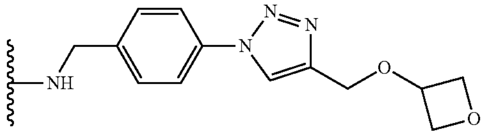 [SMILES: *NCc1ccc(-n2cc(COC3COC3)nn2)cc1] |
| 112 | 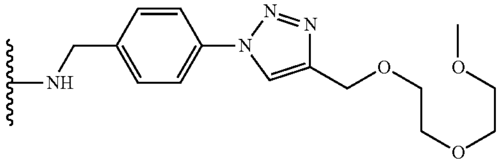 [SMILES: *NCc1ccc(-n2cc(COCCOCCOC)nn2)cc1] |
| 113 | 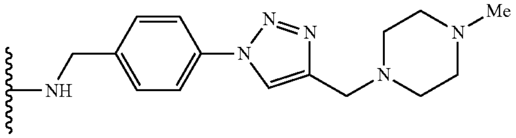 [SMILES: *NCc1ccc(-n2cc(CN3CCN(C)CC3)nn2)cc1] |
| 114 | 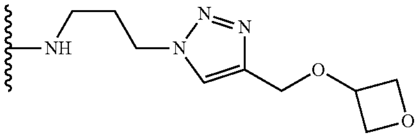 [SMILES: *NCCCn1cc(COC2COC2)nn1] |
| 115 | 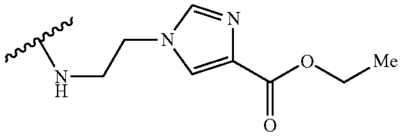 [SMILES: *NCCn1cnc(C(=O)OCC)c1] |
| 116 | 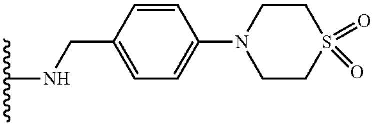 [SMILES: *NCc1ccc(N2CCS(=O)(=O)CC2)cc1] |
| 117 | 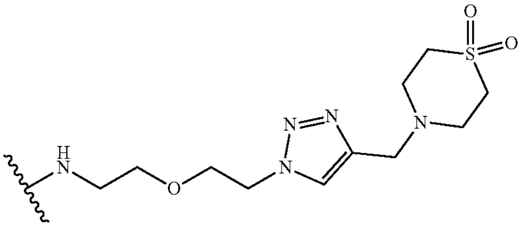 [SMILES: *NCCOCCn1cc(CN2CCS(=O)(=O)CC2)nn1] |
| 118 | 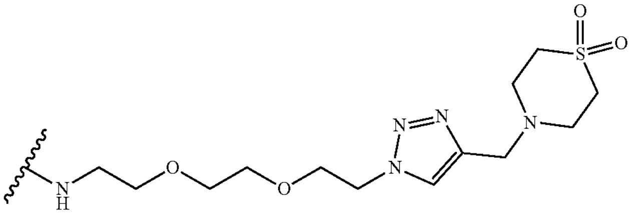 [SMILES: *NCCOCCOCCn1cc(CN2CCS(=O)(=O)CC2)nn1] |

TABLE 3-continued

| Exemplary compounds of Formula (I) | |
|---|---|
| Compound No. | Structure |
| 119 | 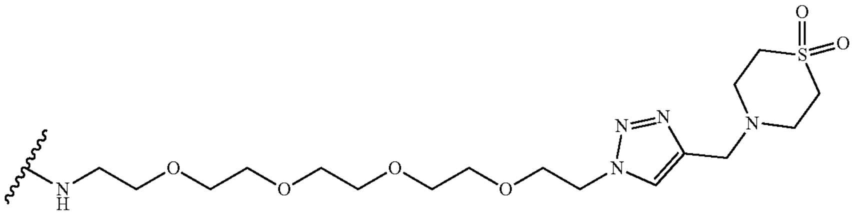 [SMILES: *NCCOCCOCCOCCOCCn1cc(CN2CCS(=O)(=O)CC2)nn1] |
| 120 | 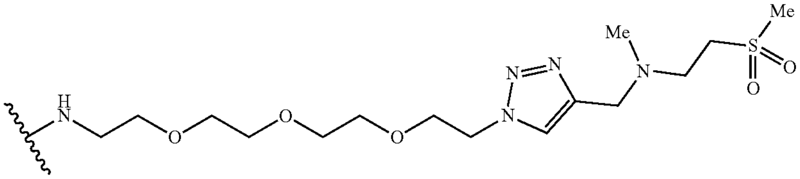 [SMILES: *NCCOCCOCCOCCn1cc(CN(C)CCS(C)(=O)=O)nn1] |
| 121 | 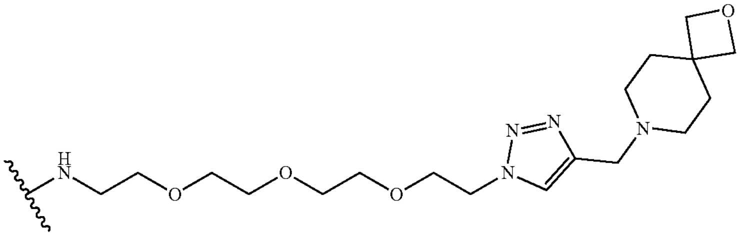 [SMILES: *NCCOCCOCCOCCn1cc(CN2CCC3(CC2)COC3)nn1] |

In some embodiments, the compound is a compound of Formula (I) (e.g., Formulas (I-a), (I-b), (I-c), (I-d), (I-e), (I-f), (II), (II-a), (III), (III-a), (III-b), (III-c), or (III-d)), or a pharmaceutically acceptable salt thereof, and is selected from:

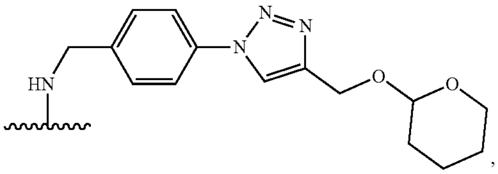

,

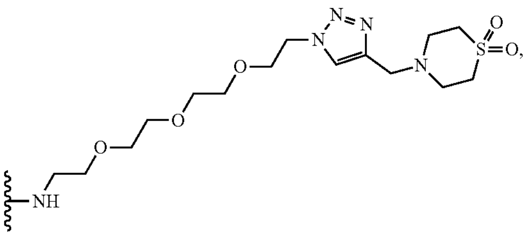

and

-continued

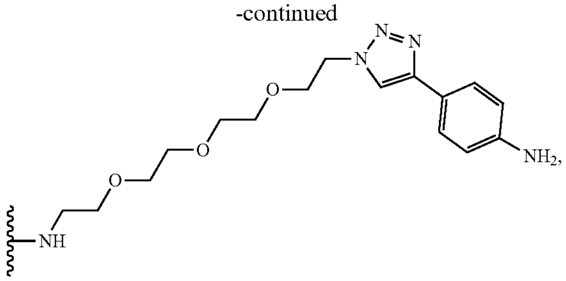

or a pharmaceutically acceptable salt thereof.

In some embodiments, the device described herein comprises the compound of

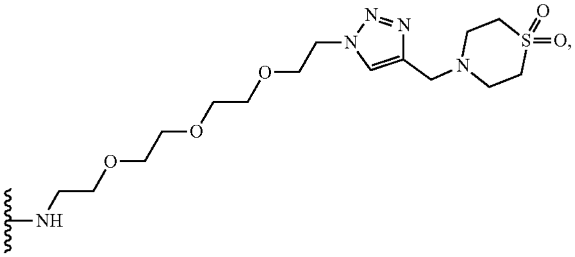

-continued

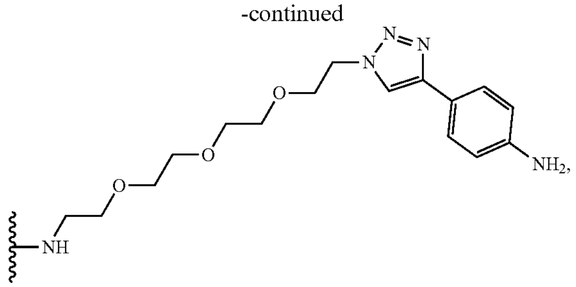

or a pharmaceutically acceptable salt thereof.

In an embodiment, a device described herein comprises a compound of Formula (I) (e.g., a compound shown in Table 3) covalently bound to an alginate polymer. The alginate polymer can be chemically modified with a compound of Formula (I) using any suitable method known in the art, e.g., as described in WO 2019/195055.

Methods of Treatment

Described herein are methods for preventing or treating a disease, disorder, or condition in a subject by administering to the subject a plurality of genetically modified cells described herein that produce a therapeutic agent that treats the disease, disorder or condition. The cells may be administered by implanting into the subject a device containing the cells as described herein, or a preparation of such devices. In an embodiment, the device or preparation is implanted (e.g., via laparoscopy) into the intraperitoneal space, e.g., the greater sac of the peritoneal cavity. In an embodiment, the genetically modified cells are engineered RPE cells, and the method comprises administering (e.g., implanting) an effective amount of a composition of two-compartment alginate hydrogel capsules which comprise the engineered RPE cells and a cell-binding polymer described herein in the inner compartment and comprise a Compound of Formula (I), e.g., Compound 101, on the outer capsule surface. In some embodiments, the method of treatment directly or indirectly reduces or alleviates at least one symptom of the disease, disorder, or condition and/or the method prevents or slows the onset of the disease, disorder, or condition. In some embodiments, the subject is a human.

In some embodiments, the disease, disorder, or condition affects a system of the body, e.g. the nervous system (e.g., peripheral nervous system (PNS) or central nervous system (CNS)), vascular system, skeletal system, respiratory system, endocrine system, lymph system, reproductive system, or gastrointestinal tract. In some embodiments, the disease, disorder, or condition affects a part of the body, e.g., blood, eye, brain, skin, lung, stomach, mouth, ear, leg, foot, hand, liver, heart, kidney, bone, pancreas, spleen, large intestine, small intestine, spinal cord, muscle, ovary, uterus, vagina, or penis.

In some embodiments, the disease, disorder or condition is a neurodegenerative disease, diabetes, a heart disease, an autoimmune disease, a cancer, a liver disease, a lysosomal storage disease, a blood clotting disorder or a coagulation disorder, an orthopedic condition, an amino acid metabolism disorder.

In some embodiments, the disease, disorder or condition is a neurodegenerative disease. Exemplary neurodegenerative diseases include Alzheimer[S] disease, Huntington [S] disease, Parkinson[S] disease (PD) amyotrophic lateral sclerosis (ALS), multiple sclerosis (MS) and cerebral palsy (CP), dentatorubro-pallidoluysian atrophy (DRPLA), neuronal intranuclear hyaline inclusion disease (NIHID), dementia with Lewy bodies, Down[S] syndrome, Hallervorden-Spatz disease, prion diseases, argyrophilic grain dementia, cortocobasal degeneration, dementia pugilistica, diffuse neurofibrillary tangles, Gerstmann-Straussler-Scheinker disease, Jakob-Creutzfeldt disease, Niemann-Pick disease type 3, progressive supranuclear palsy, subacute sclerosing panencephalitis, spinocerebellar ataxias, Pick [S] disease, and dentatorubral-pallidoluysian atrophy.

In some embodiments, the disease, disorder, or condition is an autoimmune disease, e.g., scleroderma, multiple sclerosis, lupus, or allergies.

In some embodiments, the disease is a liver disease, e.g., hepatitis B, hepatitis C, cirrhosis, NASH.

In some embodiments, the disease, disorder, or condition is cancer. Exemplary cancers include leukemia, lymphoma, melanoma, lung cancer, brain cancer (e.g., glioblastoma), sarcoma, pancreatic cancer, renal cancer, liver cancer, testicular cancer, prostate cancer, or uterine cancer.

In some embodiments, the disease, disorder, or condition is an orthopedic condition. Exemplary orthopedic conditions include osteoporosis, osteonecrosis, Paget's disease, or a fracture.

In some embodiments, the disease, disorder or condition is a lysosomal storage disease. Exemplary lysosomal storage diseases include Gaucher disease (e.g., Type I, Type II, Type III), Tay-Sachs disease, Fabry disease, Farber disease, Hurler syndrome (also known as mucopolysaccharidosis type I (MPS I)), Hunter syndrome, lysosomal acid lipase deficiency, Niemann-Pick disease, Salla disease, Sanfilippo syndrome (also known as mucopolysaccharidosis type IIIA (MPS3A)), multiple sulfatase deficiency, Maroteaux-Lamy syndrome, metachromatic leukodystrophy, Krabbe disease, Scheie syndrome, Hurler-Scheie syndrome, Sly syndrome, hyaluronidase deficiency, Pompe disease, Danon disease, gangliosidosis, or Morquio syndrome.

In some embodiments, the disease, disorder, or condition is a blood clotting disorder or a coagulation disorder. Exemplary blood clotting disorders or coagulation disorders include hemophilia (e.g., hemophilia A or hemophilia B), Von Willebrand disease, thrombocytopenia, uremia, Bernard-Soulier syndrome, Factor XII deficiency, vitamin K deficiency, or congenital afibrinogenimia.

In some embodiments, the disease, disorder, or condition is an amino acid metabolism disorder, e.g., phenylketonuria, tyrosinemia (e.g., Type 1 or Type 2), alkaptonuria, homocystinuria, hyperhomocysteinemia, maple syrup urine disease.

In some embodiments, the disease, disorder, or condition is a fatty acid metabolism disorder, e.g., hyperlipidemia, hypercholesterolemia, galactosemia.

In some embodiments, the disease, disorder, or condition is a purine or pyrimidine metabolism disorder, e.g., Lesch-Nyhan syndrome.

In some embodiments, the disease, disorder, or condition is diabetes (e.g., Type I or Type II diabetes). In some embodiments, the disease, disorder or condition is not Type I diabetes. In some embodiments, the disease, disorder or condition is not Type II diabetes.

ENUMERATED EXEMPLARY EMBODIMENTS

1. A genetically modified cell comprising at least one exogenous transcription unit inserted into at least one genomic open chromatin region (OCR), wherein the cell is derived from a human cell and the OCR is selected from the group consisting of:

a. a first OCR on Chromosome 2 (Chr 2) and located between nucleotide positions corresponding to positions 100817157 and 100818556 in the human hg19 reference genome (hg19) sequence for Chr 2;

b. a first OCR on Chr 2 which comprises SEQ ID NO:1 or a nucleotide sequence that is at least 90%, 95%, 98%, or 99% identical to SEQ ID NO:1;

c. a second OCR on Chromosome 5 (Chr 5) and located between nucleotide positions corresponding to 53853682 and 53854987 of the hg19 sequence for Chr 5;

d. a second OCR on Chr 5 which comprises SEQ ID NO:2 or a nucleotide sequence that is at least 90%, 95%, 98%, or 99% identical to SEQ ID NO:2;

e. a third OCR on Chromosome 12 (Chr 12) and located between nucleotide positions corresponding to 122186354 and 122187572 in the hg19 sequence for Chr 12;

f. a third OCR on Chr 12 which comprises SEQ ID NO:3 or a nucleotide sequence that is at least 90%, 95%, 98%, or 99% identical to SEQ ID NO:3;

g. a fourth OCR on Chromosome 8 (Chr 8) and located between nucleotide positions corresponding to 30,105,939 and 30,105,944 in the human hg38 reference genome sequence for Chr 8; and h. a fourth OCR on Chr 12 which comprises SEQ ID NO:26 or a nucleotide sequence that is at least 90%, 95%, 98%, or 99% identical to SEQ ID NO:26.

2. The genetically modified cell of embodiment 1, wherein the exogenous transcription unit is inserted into any two of the first, second and third OCRs.

3. The genetically modified cell of embodiment 1, wherein the exogenous transcription unit is inserted into each of the first, second and third OCRs.

4. The genetically modified cell of any one of embodiments 1 to 3, wherein the exogenous transcription unit in the first OCR is inserted at a site located between two nucleotide positions corresponding to positions $x_1$ and $y_1$ in SEQ ID NO:1, wherein:

a. $x_1$ and $y_1$ are 10 and 1200;

b. $x_1$ and $y_1$ are 25 and 900;

c. $x_1$ and $y_1$ are 50 and 600;

d. $x_1$ and $y_1$ are 100 and 300; or e. $x_1$ and $y_1$ are 200 and 250.

5. The genetically modified cell of any one of embodiments 1 to 4, wherein the exogenous transcription unit in the first OCR is inserted at a site located between two nucleotide positions corresponding to:

a. positions 211 and 218 in SEQ ID NO:1 or b. positions 100,817,368 and 100,817,374 in the hg19 sequence for Chr 2.

6. The genetically modified cell of any one of embodiments 1 to 5, wherein the transcription unit in the second OCR is inserted at a site located between two nucleotide positions corresponding to positions $x_2$ and $y_2$ in SEQ ID NO:2, wherein:

a. $x_2$ and $y_2$ are 10 and 1100;

b. $x_2$ and $y_2$ are 20 and 800;

c. $x_2$ and $y_2$ are 30 and 500;

d. $x_2$ and $y_2$ are 40 and 200; or e. $x_2$ and $y_2$ are 50 and 100.

7. The genetically modified cell of embodiment 6, wherein the transcription unit in the second OCR is inserted at a site located between two nucleotide positions corresponding to:

a. positions 59 and 60 in SEQ ID NO:2 or b. positions 53,853,740 and 53,853,741 in the hg19 sequence for Chr 5.

8. The genetically modified cell of any one of embodiments 1 to 7, wherein the transcription unit in the third OCR is inserted at a site located between two positions corresponding to positions $x_3$ and $y_3$ in SEQ ID NO:3, wherein:

a. $x_3$ and $y_3$ are 50 and 1200;

b. $x_3$ and $y_3$ are 100 and 1000;

c. $x_3$ and $y_3$ are 200 and 800;

d. $x_3$ and $y_3$ are 400 and 600; or e. $x_3$ and $y_3$ are 500 and 550.

9. The genetically modified cell of embodiment 8, wherein the transcription unit in the third OCR is inserted at a site located between two nucleotide positions corresponding to:

a. positions 518 and 525 in SEQ ID NO:3 or b. positions 122,186,872 and 122,186,877 in the hg19 sequence for Chr 12.

10. The genetically modified cell of any one of embodiments 1 to 9, wherein the transcription unit in the fourth OCR is inserted at a site located between two positions corresponding to positions $x_4$ and $y_4$ in SEQ ID NO:26, wherein:

a. $x_4$ and $y_4$ are 50 and 950;

b. $x_4$ and $y_4$ are 150 and 850;

c. $x_4$ and $y_4$ are 300 and 700;

d. $x_4$ and $y_4$ are 400 and 600; or e. $x_4$ and $y_4$ are 425 and 475.

11. The genetically modified cell of embodiment 10, wherein the transcription unit in the fourth OCR is inserted at a site located between two nucleotide positions corresponding to:

a. positions 440 and 445 in SEQ ID NO:26 or b. positions 30,105,939 and 30,105,944 in the human hg38 reference genome sequence for Chr 8.

12. The genetically modified cell of any one of embodiments 1 to 11, which is derived from a human immortalized cell.

13. The genetically modified cell of any one of embodiments 1 to 12, which is derived from a human retinal epithelial cell line.

14. The genetically modified epithelial cell of embodiment 13, wherein the human retinal epithelial cell line is the ARPE-19 cell line.

15. The genetically modified cell of any one of embodiments 1 to 14, wherein the exogenous transcription unit comprises a promoter sequence operably linked to a coding sequence for a polypeptide.

16. The genetically modified cell of embodiment 15, wherein the promoter sequence consists essentially of or consists of SEQ ID NO:4 or SEQ ID NO:5.

17. The genetically modified cell of embodiment 15 or 16, wherein the coding sequence is operably linked to a polyA signal sequence which consists essentially of, or consists of, SEQ ID NO:6.

18. The genetically modified cell of any one of embodiments 15 to 17, wherein the exogenous transcription unit comprises, consists of, or consists essentially of SEQ ID NO:7 and the coding sequence is inserted between nucleotides 2099 and 2100 of SEQ ID NO:7.

19. The genetically modified cell of any one of embodiments 15 to 18, which is derived from a human RPE cell and the coding sequence is codon-optimized for expression in the genetically modified cell.

20. The genetically modified cell of any one of embodiments 15 to 19, wherein the coding sequence is for a polypeptide selected from the group consisting of: an FVII protein, an FVIII protein, a FIX protein, and a GLA protein.

21. The genetically modified cell of embodiment 20, which is derived from the ARPE-19 cell line and the coding sequence is for a FVIII-BDD protein which comprises an amino acid sequence selected from the group consisting of SEQ ID NO:8, SEQ ID NO:10, SEQ ID NO:12, SEQ ID NO:13, SEQ ID NO:14 and SEQ ID NO:15.

22. The genetically modified cell of embodiment 21, wherein the amino acid sequence is SEQ ID NO:8 and the coding sequence is SEQ ID NO:9.

23. The genetically modified cell of embodiment 21, wherein the amino acid sequence is SEQ ID NO:10 and the coding sequence is SEQ ID NO:11.

24. The genetically modified cell of embodiment 20, which is derived from the ARPE-19 cell line and the coding sequence is for a Factor IX protein which comprises the amino acid sequence of SEQ ID NO:16.

25. The genetically modified cell of embodiment 24, wherein the coding sequence is SEQ ID NO:17.

26. The genetically modified cell of embodiment 20, which is derived from the ARPE-19 cell line and the coding sequence is for a Factor VII protein which comprises SEQ ID NO:18 and the coding sequence is SEQ ID NO:19 or SEQ ID NO:20.

27. The genetically modified cell of embodiment 20, which is derived from the ARPE-19 cell line and the coding sequence is for a GLA protein which comprises an amino acid sequence selected from the group consisting of SEQ ID NO:21, SEQ ID NO:24 and SEQ ID NO:25.

28. The genetically modified cell of embodiment 26, wherein the amino acid sequence is SEQ ID NO:21 and the coding sequence is SEQ ID NO:22 or SEQ ID NO:23.

29. A composition comprising a plurality of genetically modified cells, wherein each cell in the plurality is a genetically modified cell as defined by any one of embodiments 1 to 28.

30. The composition of embodiment 29, wherein the plurality of cells is obtained by culturing a monoclonal cell line.

31. The composition of embodiment 29 or 30, wherein the cells are suspended in a storage medium.

32. A device comprising the composition of any one of embodiments 29 to 31.

33. An implantable device which comprises at least one cell-containing compartment comprising a genetically modified cell or a plurality of the genetically modified cell and at least one means for mitigating the foreign body response (FBR) when the device is implanted into the subject, wherein the genetically modified cell or each cell in the plurality is a genetically modified cell as defined by any one of embodiments 1 to 28.

34. The device of embodiment 33, wherein the at least one cell-containing compartment comprises a polymer composition which encapsulates the plurality of engineered RPE cells, and optionally comprises at least one cell-binding substance (CBS).

35. The device of embodiment 33 or 34, wherein the cell-containing compartment comprises an alginate hydrogel and is surrounded by a barrier compartment, which comprises an alginate hydrogel and optionally comprises a compound of Formula (I), e.g., Compound 101, disposed on the outer surface of the barrier compartment.

36. The device of embodiment 35, wherein the barrier compartment comprises an alginate chemically modified with Compound 101.

37. The device of any one of embodiments 34 to 36, wherein the polymer composition comprises an alginate covalently modified with a peptide, wherein the peptide consists essentially of or consists of GRGDSP, GGRGDSP or GGGRGDSP.

38. The device of any one of embodiments 32 to 37, which is a hydrogel capsule of about 0.75 mm to about 2 mm in diameter, wherein the hydrogel capsule comprises an inner compartment surrounded by an outer compartment, wherein the genetically modified cells are contained in the inner compartment and the outer compartment is substantially free of the cells.

39. A preparation of devices, wherein each device in the preparation is a device as defined in any one of embodiments 32 to 38.

40. A method of treating a subject for hemophilia A, comprising:

- providing a preparation of devices which contain a plurality of genetically modified cells expressing a Factor VIII protein; and
- disposing the preparation in the body of the subject;
- wherein each cell in the plurality is the genetically modified cell of any one of embodiments 21 to 23.

41. The method of embodiment 40, wherein the disposing step comprises placing the preparation into the intraperitoneal space.

42. The method of embodiment 40 or 41, wherein the disposing step comprises placing the preparation into the greater sac of the peritoneal cavity.

43. The genetically modified cell of any one of embodiments 1 to 28, which comprises a first transcription unit and a second transcription unit inserted in tandem in one or more of the OCRs, wherein the promoter sequence in the first transcription unit is different than the promoter sequence in the second transcription unit.

44. The genetically modified cell of embodiment 43, wherein the promoter sequences in the first and second transcription units comprise SEQ ID NO:4 and SEQ ID NO:5, respectively, or the promoter sequences in the first and second transcription units comprise SEQ ID NO:5 and SEQ ID NO:4, respectively.

EXAMPLES

In order that the disclosure described herein may be more fully understood, the following examples are set forth. The examples described in this application are offered to illustrate the genetically modified cells, compositions and implantable devices and methods provided herein, and are not to be construed in any way as limiting their scope.

Example 1: Generation and Evaluation of Clones Expressing a FVIII-BDD Protein ARPE-19 cells were engineered to express a FVIII-BDD protein using the PiggyBac transposon system, which is capable of mediating transfer of a transcription unit between a plasmid vector and TTAA chromosomal sites through a "cut and paste" mechanism. ARPE-19 cells were split and seeded at 400,000 cells per 6-well culture plate and then co-transfected with varying amounts of two plasmids: (1) a transposon vector comprising a transcription unit encoding SEQ ID NO:8 inserted between inverted terminal repeat (ITR) elements recognized by a PiggyBac transposase and (2) a helper plasmid that expresses a piggyBac transposase enzyme and a fluorescent reporter protein (FRP). The transcription unit consisted of the FVIII-BDD coding sequence (SEQ ID NO:9) inserted between nucleotides 2099 and 2100 of SEQ ID NO:7.

At 24 hours post transfection, the cells were sorted via fluorescence activated cell sorting (FACS) and FRP-expressing cells were collected into three pools: one pool for each of three different transfection conditions. Selected clones from each pool were cultured in 6-well plates until they reached 75% confluency (2-3 days), the culture media was replaced with fresh media, cell supernatants were collected 24 hours later and assayed for FVIII protein concentration using ELISA. The number of genomic copies of the exogenous FVIII-BDD transcription unit was estimated using digital droplet PCR (ddPCR).

The pool with the highest FVIII-BDD supernatant levels was selected for clone isolation and screening for FVIII-BDD expression and genomic copy number. A total of 1030 clones were screened: 66 of these clones were identified as being genetically modified with 1 to 8 copies of the FVIII-BDD transcription unit, with the majority of clones having 1 copy. Most of the 66 genetically modified clones failed to divide to sufficient numbers necessary for cell banking. ELISA measurement of FVIII-BDD expression was performed on culture supernatants of the 16 clones that expanded out of wells in a 96-well plate and varying amounts of FVIII-BDD levels were observed (data not shown). Six of the 16 clones failed to expand for final banking. FVIII-BDD expression analysis was repeated on test thaws of clones that expanded to a final bank to ensure that FVIII-BDD expression remained constant. Table 4 below shows the growth characteristics and FVIII-BDD production by eight of the higher expressing clones measured at two time points seven days apart.

TABLE 4

Characteristics of certain FVIII-BDD expressing clonal cell lines

| | FVIII-BDD Production Picograms per cell per day | | |
|---|---|---|---|
| Clone No. | Time point 1 | Time point 2 | Doubling Time |
| 1 | 7.37 | 7.49 | 48 to 70 hours |
| 2 | 4.73 | 4.35 | >72 hours |
| 3 | 2.13 | 3.12 | >72 hours |
| 4 | 2.10 | 1.03 | 24 to 48 hours |
| 5 | 2.55 | 4.60 | 24 to 48 hours |
| 6 | 5.31 | 2.67 | >72 hours |
| 7 | 2.37 | 1.56 | 24 to 48 hours |
| 8 | 7.10 | 5.87 | 24 to 48 hours |

Clone No. 1 had the highest and most consistent FVIII-BDD production, with good growth characteristics. The genome of this clone was analyzed to determine the number and location of inserted transcription units, with the results showing insertion of a single transcription unit at each of three sites, which correspond to positions 100,817,368 and 100,817,374 in the hg19 sequence for Chr 2; positions 53,853,740 and 53,853,741 in the hg19 sequence for Chr 5; positions 122,186,872 and 122,186,877 in the hg19 sequence for Chr 12. A second analysis was performed on this clone, which confirmed the insertions sites on chromosome 2, 5 and 12, and identified a fourth insertion site on chromosome 8, which corresponds to positions 30,105,939 and 30,105,944 in the hg38 sequence for Chr 8.

Example 2: Culturing of Exemplary Genetically-Modified ARPE-19 Cells for Encapsulation Genetically modified ARPE-19 cells comprising a stably integrated exogenous transcription unit as described herein may be cultured to produce a composition of cells suitable for encapsulation in two compartment hydrogel capsules. Cells are grown in complete growth medium (DMEM:F12 with 10% FBS) in 150 $cm^2$ cell culture flasks or Cell-STACK® Culture Chambers (Corning Inc., Corning, NY). To passage cells, the medium in the culture flask are aspirated, and the cell layer is briefly rinsed with phosphate buffered saline (pH 7.4, 137 mM NaCl, 2.7 mM KCl, 8 mM $Na_2HPO_4$, and 2 mM $KH_2PO_4$, Gibco). 5-10 mL of 0.05% (w/v) trypsin/0.53 mM EDTA solution ("TrypsinEDTA") is added to the flask, and the cells are observed under an inverted microscope until the cell layer is dispersed, usually between 3-5 minutes. To avoid clumping, cells are handled with care and hitting or shaking the flask during the dispersion period is minimized. If the cells do not detach, the flasks are placed at 37° C. to facilitate dispersal. Once the cells disperse, 10 mL complete growth medium is added and the cells are aspirated by gentle pipetting. The cell suspension is transferred to a centrifuge tube and spun down at approximately 125×g for 5-10 minutes to remove TrypsinEDTA. The supernatant is discarded, and the cells are resuspended in fresh growth medium. Appropriate aliquots of cell suspension are added to new culture vessels, which are incubated at 37° C. The medium is renewed weekly.

Example 3: Preparation of Exemplary Modified Polymers

Chemically-modified Polymer. A polymeric material may be chemically modified with a compound of Formula (I) (or pharmaceutically acceptable salt thereof) prior to formation of a device described herein (e.g., a hydrogel capsule). For example, in the case of alginate, the alginate carboxylic acid is activated for coupling to one or more amine-functionalized compounds to achieve an alginate modified with an afibrotic compound, e.g., a compound of Formula (I). The alginate polymer is dissolved in water (30 mL/gram polymer) and treated with 2-chloro-4,6-dimethoxy-1,3,5-triazine (0.5 eq) and N-methylmorpholine (1 eq). To this mixture is added a solution of the compound of interest (e.g., Compound 101 shown in Table 3) in acetonitrile (0.3M).

The amounts of the compound and coupling reagent added depends on the desired concentration of the compound bound to the alginate, e.g., conjugation density. A medium conjugation density of Compound 101 typically ranges from 2% to 5% N, while a high conjugation density of Compound 101 typically ranges from 5.1% to 8% N. To prepare a solution of low molecular weight alginate, chemically modified with a medium conjugation density of Compound 101 (CM-LMW-Alg-101-Medium polymer), the dissolved unmodified low molecular weight alginate (approximate MW <75 kDa, G:M ratio ≥1.5) is treated with 2-chloro-4,6-dimethoxy-1,3,5-triazine (5.1 mmol/g alginate) and N-methylmorpholine (10.2 mmol/g alginate) and Compound 101 (5.4 mmol/g alginate). To prepare a solution of low molecular weight alginate, chemically modified with a high conjugation density of Compound 101 (CM-LMW-Alg-101-High polymer), the dissolved unmodified low-molecular weight alginate (approximate MW <75 kDa, G:M ratio ≥1.5) is treated with 2-chloro-4,6-dimethoxy-1,3,5-triazine (5.1 mmol/g alginate) and N-methylmorpholine (10.2 mmol/g alginate) and Compound 101 (10.5 mmol/g alginate).

The reaction is warmed to 55° C. for 16h, then cooled to room temperature and gently concentrated via rotary evaporation, then the residue is dissolved in water. The mixture is filtered through a bed of cyano-modified silica gel (Silicycle) and the filter cake is washed with water. The resulting solution is then extensively dialyzed (10,000 MWCO membrane) and the alginate solution is concentrated via lyophilization to provide the desired chemically-modified alginate as a solid or is concentrated using any technique suitable to produce a chemically modified alginate solution with a viscosity of 25 cP to 35 cP.

The conjugation density of a chemically modified alginate is measured by combustion analysis for percent nitrogen. The sample is prepared by dialyzing a solution of the chemically modified alginate against water (10,000 MWCO membrane) for 24 hours, replacing the water twice followed by lyophilization to a constant weight.

CBP-Alginates. A polymeric material may be covalently modified with a cell-binding peptide prior to formation of a device described herein (e.g., a hydrogel capsule described herein) using methods known in the art, see, e.g., Jeon 0, et al., *Tissue Eng Part A*. 16:2915-2925 (2010) and Rowley, J. A. et al., *Biomaterials* 20:45-53 (1999).

For example, in the case of alginate, an alginate solution (1%, w/v) is prepared with 50 mM of 2-(N-morpholino)-ethanesulfonic acid hydrate buffer solution containing 0.5M NaCl at pH 6.5, and sequentially mixed with N-hydroxysuccinimide and 1-ethyl-3-[3-(dimethylamino)propyl] carbodiimide (EDC). The molar ratio of N-hydroxysuccinimide to EDC is 0.5:1.0. The peptide of interest is added to the alginate solution. The amounts of peptide and coupling reagent added depends on the desired concentration of the peptide bound to the alginate, e.g., peptide conjugation density. By increasing the amount of peptide and coupling reagent, higher conjugation density can be obtained. After reacting for 24 h, the reaction is purified by dialysis against ultrapure deionized water (diH2O) (MWCO 3500) for 3 days, treated with activated charcoal for 30 min, filtered (0.22 mm filter), and concentrated to the desired viscosity.

The conjugation density of a peptide-modified alginate is measured by combustion analysis for percent nitrogen. The sample is prepared by dialyzing a solution of the chemically modified alginate against water (10,000 MWCO membrane) for 24 hours, replacing the water twice followed by lyophilization to a constant weight.

Example 4: Preparation of Exemplary Alginate Solutions for Making Hydrogel Capsules 70:30 mixture of chemically-modified and unmodified alginate. A low molecular weight alginate (PRONOVA™ VLVG alginate, NovaMatrix, Sandvika, Norway, cat. #4200506, approximate molecular weight <75 kDa; G:M ratio ≥1.5) is chemically modified with Compound 101 to produce chemically modified low molecular weight alginate (CM-LMW-Alg-101) solution with a viscosity of 25 cp to 35 cP and a conjugation density of 5.1% to 8% N, as determined by combustion analysis for percent nitrogen. A solution of high molecular weight unmodified alginate (U-HMW-Alg) is prepared by dissolving unmodified alginate (PRONOVA™ SLG100, NovaMatrix, Sandvika, Norway, cat. #4202106, approximate molecular weight of 150 kDa-250 kDa) at 3% weight to volume in 0.9% saline. The CM-LMW-Alg solution is blended with the U-HMW-Alg solution at a volume ratio of 70% CM-LMW-Alg to 30% U-HMW-Alg (referred to herein as a70:30 CM-Alg:UM-Alg solution).

Unmodified alginate solution. An unmodified medium molecular weight alginate (SLG20, NovaMatrix, Sandvika, Norway, cat. #4202006, approximate molecular weight of 75-150 kDa), is dissolved at 1.4% weight to volume in 0.9% saline to prepare a U-MMW-Alg solution.

Unmodified alginate solution. An unmodified medium molecular weight alginate (SLG20, NovaMatrix, Sandvika, Norway, cat. #4202006, approximate molecular weight of 75-150 kDa), is dissolved at 1.4% weight to volume in 0.9% saline to prepare a U-MMW-Alg solution.

Alginate Solution Comprising Cell Binding Sites. A solution of SLG20 alginate is modified with a peptide consisting of GRGDSP as described above and concentrated to a viscosity of about 100 cP. The amount of the peptide and coupling reagent used are selected to achieve a target peptide conjugation density of about 0.2 to 0.3, as measured by combustion analysis.

Example 5: Formation of Exemplary Two-Compartment Hydrogel Capsules

Suspensions of genetically modified cells as single cells are encapsulated in two-compartment hydrogel capsules according to the protocols described below.

Immediately before encapsulation, a desired volume of a composition comprising the cells (e.g., from a culture of the cells as described in Example 1) are centrifuged at 1,400 r.p.m. for 1 min and washed with calcium-free Krebs-Henseleit (KH) Buffer (4.7 mM KCl, 25 mM HEPES, 1.2 mM $KH_2PO_4$, 1.2 mM $MgSO_4 \times 7H_2O$, 135 mM NaCl, pH ≈7.4, ≈290 mOsm). After washing, the cells are centrifuged again and all of the supernatant is aspirated. The cell pellet is resuspended in the GRGDSP-modified alginate solution described in Example 3 at a desired cell density (e.g., about 50 to 150 million suspended single cells per ml alginate solution).

Prior to fabricating hydrogel capsules, buffers and alginate solutions are sterilized by filtration through a0.2-μm filter using aseptic processes.

To prepare two-compartment hydrogel millicapsules of about 1.5 mm diameter, an electrostatic droplet generator is set up as follows: an ES series 0-100-kV, 20-watt high-voltage power generator (EQ series, Matsusada, NC, USA) is connected to the top and bottom of a coaxial needle (inner lumen of 22G, outer lumen of 18G, Ramé-Hart Instrument Co., Succasunna, NJ, USA). The inner lumen is attached to a first 5-ml Luer-lock syringe (BD, NJ, USA), which is connected to a syringe pump (Pump 11 Pico Plus, Harvard Apparatus, Holliston, MA, USA) that is oriented vertically. The outer lumen is connected via a luer coupling to a second 5-ml Luer-lock syringe which is connected to a second syringe pump (Pump 11 Pico Plus) that is oriented horizontally. A first alginate solution containing the genetically modified cells (as single cells) suspended in a GRGDSP-modified alginate solution is placed in the first syringe and a cell-free alginate solution comprising a mixture of a chemically-modified alginate and unmodified alginate is placed in the second syringe. The two syringe pumps move the first and second alginate solutions from the syringes through both lumens of the coaxial needle and single droplets containing both alginate solutions are extruded from the needle into a glass dish containing a cross-linking solution. The settings of each Pico Plus syringe pump are 12.06 mm diameter and the flow rates of each pump are adjusted to achieve a flow rate ratio of 1:1 for the two alginate solutions. Thus, with the total flow rate set at 10 ml/h, the flow rate for each alginate solution was about 5 mL/h. Control (empty) capsules are prepared in the same manner except that the alginate solution used for the inner compartment is a cell-free solution.

After extrusion of the desired volumes of alginate solutions, the alginate droplets are crosslinked for five minutes in a cross-linking solution which contained 25 mM HEPES buffer, 20 mM $BaCl_2$, 0.2M mannitol and 0.01% of poloxamer 188. Capsules that fall to the bottom of the crosslinking vessel are collected by pipetting into a conical tube. After the capsules settle in the tube, the crosslinking buffer is removed, and capsules are washed four times in HEPES buffer, two times in 0.9% saline, and two times in culture media and stored in an incubator at 37° C.

EQUIVALENTS AND SCOPE

This application refers to various issued patents, published patent applications, journal articles, and other publications, all of which are incorporated herein by reference in their entirety. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, Figures, or Examples but rather is as set forth in the appended claims. Those of ordinary skill in the art will appreciate that various changes and modifications to this description may be made without departing from the spirit or scope of the present disclosure, as defined in the following claims.

The invention claimed is:

1. A genetically modified cell comprising at least one exogenous transcription unit inserted into at least one genomic open chromatin region (OCR), wherein the cell is derived from a human cell and the OCR is selected from the group consisting of:

a. a first OCR on Chromosome 2 (Chr 2) and located between nucleotide positions corresponding to positions 100817157 and 100818556 in the human hg19 reference genome (hg19) sequence for Chr 2;

b. a first OCR on Chr 2 which comprises SEQ ID NO:1 or a nucleotide sequence that is at least 90%, 95%, 98%, or 99% identical to SEQ ID NO:1;

c. a second OCR on Chromosome 5 (Chr 5) and located between nucleotide positions corresponding to 53853682 and 53854987 of the hg19 sequence for Chr 5;

d. a second OCR on Chr 5 which comprises SEQ ID NO:2 or a nucleotide sequence that is at least 90%, 95%, 98%, or 99% identical to SEQ ID NO:2;

e. a third OCR on Chromosome 12 (Chr 12) and located between nucleotide positions corresponding to 122186354 and 122187572 in the hg19 sequence for Chr 12;

f. a third OCR on Chr 12 which comprises SEQ ID NO:3 or a nucleotide sequence that is at least 90%, 95%, 98%, or 99% identical to SEQ ID NO:3;

g. a fourth OCR on Chromosome 8 (Chr 8) and located between nucleotide positions corresponding to 30,105,939 and 30,105,944 in the human hg38 reference genome sequence for Chr 8; and h. a fourth OCR on Chr 12 which comprises SEQ ID NO:26 or a nucleotide sequence that is at least 90%, 95%, 98%, or 99% identical to SEQ ID NO:26.

2. The genetically modified cell of claim 1, wherein the exogenous transcription unit is inserted into any two of the first, second and third OCRs or into any two of the first, second, third and fourth OCRs.

3. The genetically modified cell of claim 1, wherein the exogenous transcription unit is inserted into each of the first, second and third OCRs or into each of the first, second, third and fourth OCRs.

4. The genetically modified cell of claim 1, wherein the exogenous transcription unit in the first OCR is inserted at a site located between two nucleotide positions corresponding to positions $x_1$ and $y_1$ in SEQ ID NO:1, wherein:

a. $x_1$ and $y_1$ are 10 and 1200;

b. $x_1$ and $y_1$ are 25 and 900;

c. $x_1$ and $y_1$ are 50 and 600;

d. $x_1$ and $y_1$ are 100 and 300; or e. $x_1$ and $y_1$ are 200 and 250.

5. The genetically modified cell of claim 1, wherein the exogenous transcription unit in the first OCR is inserted at a site located between two nucleotide positions corresponding to:

a. positions 211 and 218 in SEQ ID NO:1 or b. positions 100,817,368 and 100,817,374 in the hg19 sequence for Chr 2.

6. The genetically modified cell of claim 1, wherein the transcription unit in the second OCR is inserted at a site located between two nucleotide positions corresponding to positions $x_2$ and $y_2$ in SEQ ID NO:2, wherein:

a. $x_2$ and $y_2$ are 10 and 1100;

b. $x_2$ and $y_2$ are 20 and 800;

c. $x_2$ and $y_2$ are 30 and 500;

d. $x_2$ and $y_2$ are 40 and 200; or e. $x_2$ and $y_2$ are 50 and 100.

7. The genetically modified cell of claim 6, wherein the transcription unit in the second OCR is inserted at a site located between two nucleotide positions corresponding to:

a. positions 59 and 60 in SEQ ID NO:2 or b. positions 53,853,740 and 53,853,741 in the hg19 sequence for Chr 5.

8. The genetically modified cell of claim 1, wherein the transcription unit in the third OCR is inserted at a site located between two positions corresponding to positions $x_3$ and $y_3$ in SEQ ID NO:3, wherein:

a. $x_3$ and $y_3$ are 50 and 1200;

b. $x_3$ and $y_3$ are 100 and 1000;

c. $x_3$ and $y_3$ are 200 and 800;

d. $x_3$ and $y_3$ are 400 and 600; or e. $x_3$ and $y_3$ are 500 and 550.

9. The genetically modified cell of claim 8, wherein the transcription unit in the third OCR is inserted at a site located between two nucleotide positions corresponding to:

a. positions 518 and 525 in SEQ ID NO:3 or b. positions 122,186,872 and 122,186,877 in the hg19 sequence for Chr 12.

10. The genetically modified cell of claim 1, wherein the transcription unit in the fourth OCR is inserted at a site located between two positions corresponding to positions $x_4$ and $y_4$ in SEQ ID NO:26, wherein:

a. $x_4$ and $y_4$ are 50 and 950;

b. $x_4$ and $y_4$ are 150 and 850;

c. $x_4$ and $y_4$ are 300 and 700;

d. $x_4$ and $y_4$ are 400 and 600; or e. $x_4$ and $y_4$ are 425 and 475.

11. The genetically modified cell of claim 10, wherein the transcription unit in the fourth OCR is inserted at a site located between two nucleotide positions corresponding to:

a. positions 440 and 445 in SEQ ID NO:26 or b. positions 30,105,939 and 30,105,944 in the human hg38 reference genome sequence for Chr 8.

12. The genetically modified cell of claim 1, which is derived from a retinal epithelial cell line.

13. The genetically modified cell of claim 12, wherein the retinal epithelial cell line is the ARPE-19 cell line.

14. The genetically modified cell of claim 1, wherein the exogenous transcription unit comprises a promoter sequence operably linked to a coding sequence for a polypeptide.

15. The genetically modified cell of claim 14, wherein the polypeptide is selected from the group consisting of: an FVII protein, an FVIII protein, a FIX protein, and a GLA protein.

16. The genetically modified cell of claim 15, wherein the cell is derived from the ARPE-19 cell line and the coding sequence is for a FVIII-BDD protein which comprises SEQ ID NO:8.

17. A composition comprising a plurality of genetically modified epithelial cells, wherein each cell in the plurality is a genetically modified cell as according to claim 1.

* * * * *